(12) United States Patent
Simonnet et al.

(10) Patent No.: US 10,561,596 B2
(45) Date of Patent: *Feb. 18, 2020

(54) COMPOSITIONS AND DISPERSIONS CONTAINING PARTICLES COMPRISING A POLYMER

(71) Applicant: L'OREAL, Paris (FR)

(72) Inventors: Jean-Thierry Simonnet, New York, NY (US); Bradford Joseph Pistorio, Clark, NJ (US); Charles Michael Sanford Shaw, Madison, NJ (US); Jim Mitchell Singer, South Orange, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/251,373

(22) Filed: Apr. 11, 2014

(65) Prior Publication Data

US 2015/0290109 A1    Oct. 15, 2015

(51) Int. Cl.
*A61K 8/81* (2006.01)
*A61K 8/02* (2006.01)
(Continued)

(52) U.S. Cl.
CPC .............. *A61K 8/8117* (2013.01); *A45D 7/06* (2013.01); *A61K 8/025* (2013.01); *A61K 8/0241* (2013.01); *A61K 8/044* (2013.01); *A61K 8/375* (2013.01); *A61K 8/42* (2013.01); *A61K 8/92* (2013.01); *A61K 8/927* (2013.01); *A61Q 5/06* (2013.01)

(58) Field of Classification Search
None
See application file for complete search history.

(56) References Cited

U.S. PATENT DOCUMENTS 2,463,264 A    3/1949  Graenacher et al.
3,869,454 A    3/1975  Lang et al.
(Continued)

FOREIGN PATENT DOCUMENTS

CA    2420675 A1    8/2003
DE    2810130 A1    9/1979
(Continued)

OTHER PUBLICATIONS

International Search Report dated Mar. 10, 2015.
(Continued)

*Primary Examiner* — Nicole P Babson
(74) *Attorney, Agent, or Firm* — The Marbury Law Group, PLLC

(57) ABSTRACT

The present invention is directed to a composition containing: an aqueous dispersion comprising (a) particles having a volume-basis particle size distribution with peaks in the range of equal to or greater than 1 μm up to about 100 μm wherein the particles comprise an oil gellant comprising a styrenic block copolymer, and a fatty substance selected from a wax having a melting point of greater than 35° C., an oil, and mixtures thereof; (b) a surfactant mixture comprising a nonionic surfactant and an ionic surfactant; and (c) water; and a carrier. The composition and aqueous dispersion are capable of delivering benefits to various substrates, for example, keratinous substrates such as skin and hair.

72 Claims, 2 Drawing Sheets

(51) Int. Cl.
*A61K 8/37* (2006.01)
*A61K 8/42* (2006.01)
*A61K 8/92* (2006.01)
*A61Q 5/06* (2006.01)
*A45D 7/06* (2006.01)
*A61K 8/04* (2006.01)

(56) References Cited

U.S. PATENT DOCUMENTS

| | | | |
|---|---|---|---|
| 3,955,918 A | 5/1976 | Lang | |
| 3,985,499 A | 10/1976 | Lang et al. | |
| 4,025,301 A | 5/1977 | Lang | |
| 4,151,162 A | 4/1979 | Lang et al. | |
| 4,861,583 A | 8/1989 | Sramek | |
| 5,053,221 A | 10/1991 | Robertson et al. | |
| 5,166,355 A | 11/1992 | Leistner et al. | |
| 5,237,071 A | 8/1993 | Leistner et al. | |
| 5,585,091 A | 12/1996 | Pelzer et al. | |
| 5,618,523 A | 4/1997 | Zysman et al. | |
| 5,708,151 A | 1/1998 | Mockli | |
| 5,773,611 A | 6/1998 | Zysman et al. | |
| 5,858,338 A | 1/1999 | Piot et al. | |
| 5,874,072 A | 2/1999 | Alwattari et al. | |
| 5,925,337 A | 7/1999 | Arraudeau et al. | |
| 6,024,948 A * | 2/2000 | Samain et al. | 424/70.16 |
| 6,066,315 A | 5/2000 | Melby et al. | |
| 6,066,316 A | 5/2000 | Shiojima et al. | |
| 6,093,385 A | 7/2000 | Habeck et al. | |
| 6,120,778 A | 9/2000 | Simonnet | |
| 6,126,929 A | 10/2000 | Mougin | |
| 6,132,745 A | 10/2000 | Marchi-Lemann et al. | |
| 6,159,455 A | 12/2000 | Habeck et al. | |
| 6,165,457 A | 12/2000 | Midha et al. | |
| 6,191,301 B1 | 2/2001 | Habeck et al. | |
| 6,235,271 B1 | 5/2001 | Luther et al. | |
| 6,238,649 B1 | 5/2001 | Habeck et al. | |
| 6,248,336 B1 | 6/2001 | McDermott | |
| 6,274,131 B1 | 8/2001 | Piot et al. | |
| 6,316,011 B1 | 11/2001 | Ron et al. | |
| 6,326,013 B1 | 12/2001 | Lemann et al. | |
| 6,372,201 B1 | 4/2002 | Leuridan et al. | |
| 6,436,373 B1 | 8/2002 | Habeck et al. | |
| 6,464,990 B2 | 10/2002 | Simonnet et al. | |
| 6,503,495 B1 | 1/2003 | Alwattari et al. | |
| 6,514,485 B1 | 2/2003 | Malpede et al. | |
| 6,605,311 B2 | 8/2003 | Villagran et al. | |
| 6,645,476 B1 | 11/2003 | Morschhauser et al. | |
| 6,689,855 B2 | 2/2004 | Smith et al. | |
| 6,689,856 B2 | 2/2004 | L'Alloret | |
| 6,755,202 B1 | 6/2004 | Scholey et al. | |
| 6,793,940 B2 | 9/2004 | Tournilhac et al. | |
| 6,830,670 B1 | 12/2004 | Viovy et al. | |
| 6,838,514 B2 | 1/2005 | Yeung et al. | |
| 6,870,012 B2 | 3/2005 | Cohn et al. | |
| 6,878,754 B2 | 4/2005 | L'Alloret | |
| 6,946,123 B2 | 9/2005 | De La Poterie et al. | |
| 6,995,209 B2 | 2/2006 | Olivieri et al. | |
| 7,008,628 B2 | 3/2006 | Ron et al. | |
| 7,029,662 B2 | 4/2006 | Auguste et al. | |
| 7,115,255 B2 | 10/2006 | L'Alloret | |
| 7,138,110 B2 | 11/2006 | Auguste et al. | |
| 7,189,388 B2 | 3/2007 | Auguste et al. | |
| 7,211,244 B2 | 5/2007 | Auguste et al. | |
| 7,217,752 B2 | 5/2007 | Schmucker-Castner et al. | |
| 7,288,575 B2 | 10/2007 | Lannibois-Drean et al. | |
| 7,311,736 B2 | 12/2007 | Burguad et al. | |
| 7,335,348 B2 | 2/2008 | Giroud et al. | |
| 7,339,013 B2 | 3/2008 | Pagnoux et al. | |
| 7,399,320 B2 | 7/2008 | Burgaud et al. | |
| 7,431,919 B2 | 10/2008 | Travkina et al. | |
| 7,482,419 B2 | 1/2009 | Caprasse et al. | |
| 7,722,859 B2 | 5/2010 | L'Alloret | |
| 7,772,214 B2 | 8/2010 | Vatter et al. | |
| 7,871,600 B2 | 1/2011 | Hiraishi et al. | |
| 7,883,690 B2 | 2/2011 | Collin et al. | |
| 7,883,692 B2 | 2/2011 | L'Alloret | |
| 7,998,465 B2 | 8/2011 | De La Poterie et al. | |
| 8,211,415 B2 | 7/2012 | Pays et al. | |
| 8,388,940 B2 | 3/2013 | Pastor et al. | |
| 8,685,375 B2 | 4/2014 | Arditty et al. | |
| 8,920,787 B2 | 12/2014 | Li et al. | |
| 2001/0003586 A1 | 6/2001 | Vatter et al. | |
| 2002/0001570 A1 | 1/2002 | Heidenfelder et al. | |
| 2002/0016310 A1 | 2/2002 | Habeck et al. | |
| 2002/0085986 A1 | 7/2002 | De La Poterie et al. | |
| 2002/0098217 A1 | 7/2002 | Piot et al. | |
| 2002/0198328 A1 | 12/2002 | L'Alloret | |
| 2003/0026815 A1 | 2/2003 | Scott et al. | |
| 2003/0031640 A9 | 2/2003 | De La Poterie et al. | |
| 2003/0039671 A1 | 2/2003 | Tournilhac et al. | |
| 2003/0059377 A1 | 3/2003 | Riley | |
| 2003/0059388 A1 | 3/2003 | Auguste et al. | |
| 2003/0059389 A1 | 3/2003 | Tournilhac et al. | |
| 2003/0060559 A1 | 3/2003 | Oliviere et al. | |
| 2003/0064045 A1 | 4/2003 | Tournilhac et al. | |
| 2003/0092776 A1 | 5/2003 | Ron et al. | |
| 2003/0099709 A1 | 5/2003 | Shah et al. | |
| 2003/0103915 A1 | 6/2003 | Quintini | |
| 2003/0138465 A9 | 7/2003 | Douin et al. | |
| 2003/0143168 A1 | 7/2003 | Geffroy | |
| 2003/0143180 A1 | 7/2003 | Giroud et al. | |
| 2003/0147832 A1 | 8/2003 | L'Alloret | |
| 2003/0204014 A1 | 10/2003 | Yeung et al. | |
| 2004/0022752 A1 | 2/2004 | De La Poterie | |
| 2004/0054076 A1 | 3/2004 | Lannibois-Drean et al. | |
| 2004/0091447 A1 | 5/2004 | Pays et al. | |
| 2004/0172061 A1 | 9/2004 | Yoshioka et al. | |
| 2004/0198904 A1 | 10/2004 | Braun et al. | |
| 2004/0214913 A1 | 10/2004 | L'Alloret | |
| 2005/0002887 A1 | 1/2005 | Rollat-Corvol et al. | |
| 2005/0013782 A1 | 1/2005 | Goppel et al. | |
| 2005/0028300 A1 | 2/2005 | Burgaud et al. | |
| 2005/0031656 A1 | 2/2005 | Pays et al. | |
| 2005/0053567 A1 | 3/2005 | Liu | |
| 2005/0112080 A1 | 5/2005 | Cao et al. | |
| 2005/0169949 A1 | 8/2005 | De La Poterie et al. | |
| 2005/0175573 A1 | 8/2005 | Pagnoux et al. | |
| 2005/0191251 A1 | 9/2005 | Kravtchenko et al. | |
| 2005/0191258 A1 | 9/2005 | De La Poterie et al. | |
| 2005/0228126 A1 | 10/2005 | Lannibois-Drean et al. | |
| 2006/0030655 A1 | 2/2006 | L'Alloret et al. | |
| 2006/0111518 A1 | 5/2006 | L'Alloret | |
| 2006/0130248 A1* | 6/2006 | Pays | A61K 8/8152 8/406 |
| 2006/0156479 A1 | 7/2006 | Hercouet et al. | |
| 2006/0189485 A1 | 8/2006 | Hirokawa et al. | |
| 2006/0263438 A1 | 11/2006 | Biatry et al. | |
| 2006/0292095 A1 | 12/2006 | Biatry et al. | |
| 2007/0106020 A1 | 5/2007 | Braun et al. | |
| 2007/0149703 A1 | 6/2007 | Caprasse et al. | |
| 2007/0196299 A1 | 8/2007 | Constantinides et al. | |
| 2007/0275020 A1 | 11/2007 | Lendlein et al. | |
| 2008/0014164 A1 | 1/2008 | Jacquier | |
| 2008/0081024 A1 | 4/2008 | Beasley et al. | |
| 2008/0092307 A1 | 4/2008 | Burgaud et al. | |
| 2008/0138300 A2 | 6/2008 | Yu et al. | |
| 2008/0311050 A1 | 12/2008 | Lendlein et al. | |
| 2009/0061004 A1 | 3/2009 | Birkel et al. | |
| 2009/0136439 A1 | 5/2009 | Feng et al. | |
| 2009/0142289 A1 | 6/2009 | Arditty et al. | |
| 2009/0241980 A1 | 10/2009 | Wyatt et al. | |
| 2009/0282623 A1 | 11/2009 | Goget et al. | |
| 2009/0298971 A1 | 12/2009 | Leotsakos et al. | |
| 2010/0143424 A1 | 6/2010 | Kanazawa | |
| 2010/0150858 A1 | 6/2010 | Runglertkriangkrai | |
| 2010/0172853 A1 | 7/2010 | Pavel et al. | |
| 2010/0190870 A1 | 7/2010 | L'Alloret | |
| 2010/0242984 A1 | 9/2010 | Arditty et al. | |
| 2010/0247470 A1 | 9/2010 | Friel et al. | |
| 2010/0278770 A1 | 11/2010 | Arditty et al. | |
| 2011/0073128 A1 | 3/2011 | Ogawa et al. | |
| 2011/0123472 A1 | 5/2011 | Atis | |
| 2011/0146702 A1 | 6/2011 | Raineau | |
| 2011/0150807 A1 | 6/2011 | Bui et al. | |

(56) References Cited

U.S. PATENT DOCUMENTS

| | | |
|---|---|---|
| 2011/0182839 A1 | 7/2011 | Numata |
| 2011/0236342 A1 | 9/2011 | Dop |
| 2011/0269839 A1 | 11/2011 | Dolatkhani et al. |
| 2012/0070391 A1 | 3/2012 | Schultze et al. |
| 2012/0093560 A1 | 4/2012 | Arditty |
| 2012/0129095 A1 | 5/2012 | Levanon et al. |
| 2013/0112220 A1 | 5/2013 | Kergosien |
| 2014/0013521 A1 | 1/2014 | Goget et al. |
| 2014/0102467 A1 | 4/2014 | Pistorio et al. |
| 2014/0102468 A1 | 4/2014 | Pistorio et al. |
| 2014/0105845 A1 | 4/2014 | Bui et al. |
| 2014/0105942 A1 | 4/2014 | Pistorio et al. |
| 2014/0105943 A1 | 4/2014 | Pistorio et al. |
| 2014/0105944 A1 | 4/2014 | Pistorio et al. |
| 2014/0105945 A1 | 4/2014 | Bui et al. |

FOREIGN PATENT DOCUMENTS

| | | |
|---|---|---|
| DE | 19726184 A1 | 12/1998 |
| DE | 19746654 A1 | 6/1999 |
| DE | 19755649 A1 | 6/1999 |
| DE | 19855649 A1 | 6/2000 |
| DE | 10150726 A1 | 4/2003 |
| DE | 10162844 A1 | 7/2003 |
| EP | 0133981 A2 | 5/1985 |
| EP | 0583814 A1 | 2/1994 |
| EP | 0629649 A1 | 12/1994 |
| EP | 0669323 A1 | 8/1995 |
| EP | 0692506 A2 | 1/1996 |
| EP | 0714954 A2 | 6/1996 |
| EP | 0832642 A2 | 4/1998 |
| EP | 0893119 A1 | 1/1999 |
| EP | 0966946 A1 | 12/1999 |
| EP | 0967200 A1 | 12/1999 |
| EP | 1008586 A1 | 6/2000 |
| EP | 1027883 A2 | 8/2000 |
| EP | 1112735 A1 | 7/2001 |
| EP | 1133980 A2 | 9/2001 |
| EP | 1133981 A2 | 9/2001 |
| EP | 1174113 A1 | 1/2002 |
| EP | 1269974 A1 | 1/2003 |
| EP | 1300137 A2 | 4/2003 |
| EP | 1378544 A2 | 1/2004 |
| EP | 1407791 A1 | 4/2004 |
| EP | 1466588 A1 | 10/2004 |
| EP | 1674073 A1 | 6/2006 |
| EP | 2008644 A2 | 12/2008 |
| FR | 2140205 A1 | 1/1973 |
| FR | 2189006 A1 | 1/1974 |
| FR | 2285851 A1 | 4/1976 |
| FR | 2673179 A1 | 8/1992 |
| FR | 2694939 A1 | 2/1994 |
| FR | 2788008 A1 | 7/2000 |
| FR | 2811886 A1 | 1/2002 |
| FR | 2820976 A1 | 8/2002 |
| FR | 2840907 A1 | 12/2003 |
| FR | 2844190 A1 | 3/2004 |
| FR | 2856923 A1 | 1/2005 |
| FR | 2940062 A1 | 6/2010 |
| FR | 2961396 A1 | 12/2011 |
| FR | 2975293 A1 | 11/2012 |
| GB | 2206339 A | 1/1989 |
| GB | 23003549 A | 2/1997 |
| GB | 2408510 A | 1/2005 |
| JP | 2003-012478 A | 1/2003 |
| JP | 2003012478 A | 1/2003 |
| WO | 8901771 A1 | 3/1989 |
| WO | 8904653 A1 | 6/1989 |
| WO | 9112793 A1 | 9/1991 |
| WO | 93/04665 A1 | 3/1993 |
| WO | 95/01772 A1 | 1/1995 |
| WO | 95/15144 A1 | 6/1995 |
| WO | 97/00275 A2 | 1/1997 |
| WO | 98/06438 A2 | 2/1998 |
| WO | 98/29487 A1 | 7/1998 |
| WO | 98/48768 A1 | 11/1998 |
| WO | 98/50005 A1 | 11/1998 |
| WO | 00/00222 A1 | 1/2000 |
| WO | 00/7603 A2 | 2/2000 |
| WO | 00/35961 A1 | 6/2000 |
| WO | 00/38851 A1 | 7/2000 |
| WO | 01/41735 A2 | 6/2001 |
| WO | 02/09064 A1 | 1/2002 |
| WO | 02/15873 A2 | 2/2002 |
| WO | 02/15875 A2 | 2/2002 |
| WO | 02/32560 A2 | 4/2002 |
| WO | 02/076392 A2 | 10/2002 |
| WO | 03/008462 A1 | 1/2003 |
| WO | 03/032930 A1 | 4/2003 |
| WO | 03032930 A1 | 4/2003 |
| WO | 03/106536 A2 | 12/2003 |
| WO | 2004/006872 A1 | 1/2004 |
| WO | 2005100444 A1 | 10/2005 |
| WO | 2009/026113 A2 | 2/2009 |
| WO | 2011103080 A1 | 8/2011 |
| WO | 2011/111084 A1 | 9/2011 |
| WO | 2011/125086 A1 | 10/2011 |
| WO | 2012/028456 A2 | 3/2012 |
| WO | 2012/037502 A2 | 3/2012 |
| WO | 2013/131575 A1 | 9/2013 |
| WO | 2013190136 A2 | 12/2013 |
| WO | 2014060405 A2 | 4/2014 |

OTHER PUBLICATIONS

MicroEase Technical Data Sheet: http://www.mpipersonalcare.com/Files/TDS/MICROEASE.pdf.

Ajinomoto Product List: http://www.ajichem.com/en/products/product-list.aspx.

Reiger, Martin M. (2000). Harry's Cosmeticology, vols. I-II (8th Edition). Chemical Publishing Company Inc. Online version available at: http://app.knovel.com/hotlink/toc/id:kpHCVIIIEH/harrys-cosmeticology.

International Search Report and Written Opinion for counterpart Application No. PCT/US2013/060338, dated Dec. 23, 2013.

International Preliminary Report on Patentability for PCT/EP2013/071516, dated Apr. 30, 2015.

International Preliminary Report on Patentability for PCT/EP2013/071518, dated Apr. 30, 2015.

English language Abstract for DE 19726184A1 (Dec. 24, 1998).

English language Abstract for EP 0133981A2 (May 13, 1985).

English language Abstract for EP 2008644A2 (Dec. 31, 2008).

European Patent No. 0583814 Abstract for FR 2694939A1 (Feb. 25, 1994).

English language Abstract for FR 2820976A1 (Aug. 23, 2002).

English language Abstract for FR 2940062A1 (Jun. 25, 2010).

Office Action for counterpart European Application No. 13776511.1, dated Jun. 2, 2017.

Office Action for counterpart U.S. Appl. No. 13/651,732, dated Mar. 25, 2015.

Final Office Action for counterpart U.S. Appl. No. 13/651,732, dated Nov. 18, 2015.

Office Action for counterpart U.S. Appl. No. 13/651,732, dated Apr. 7, 2016.

Office Action for counterpart U.S. Appl. No. 13/651,768, dated Oct. 6, 2015.

Final Office Action for counterpart U.S. Appl. No. 13/651,768, dated Mar. 24, 2016.

Office Action for counterpart U.S. Appl. No. 14/809,321, dated Nov. 9, 2016.

Final Office Action for counterpart U.S. Appl. No. 14/809,321, dated Jun. 6, 2017.

Office Action for counterpart U.S. Appl. No. 14/809,321, dated Oct. 30, 2017.

Examiner's Answer to Appeal Brief for counterpart U.S. Appl. No. 13/651,768, dated Mar. 30, 2017.

Appeal Docketing Notice for counterpart U.S. Appl. No. 13/651,768, mailed Jun. 8, 2017.

(56) References Cited

OTHER PUBLICATIONS

Final Office Action for copending U.S. Appl. No. 14/809,321, dated Aug. 2, 2018.
Notice of Allowance for co-pending U.S. Appl. No. 13/651,732, dated May 22, 2019.
Andreas Lendlein and Robert Langer "Biodegradable, Elastic Shape-Memory Polymers for Potential Biomedical Applications"—Sciencemag, May 31, 2002, p. 1673-1676, vol. 296.
Andreas Lendlein, Hongyan Jiang, Oliver Juner, and Robert Langer "Light-induced shape-memory polymers"—Nature Publishing Group, Apr. 14, 2005, p. 879-882, vol. 434.
Marc Behl and Andreas Lendlei "Shape memory polymers"—Materials today, Apr. 2007, p. 20-28, vol. 10, No. 4.
P.W. Wertz, D.C. Swartzendruber, W. Abraham, K. Madison, D.T. Downing "Essential Fatty Acids and Epidermal Integrity"—Arch Dermatol, p. 1381-1384, vol. 123 Oct. 1987.
K. Robsonm, M.E. Stewart, S. Michesen, N.D. Lazo, D.T. Downing "6-Hydroxy-4-sphingenine in human epidermal ceramides"—Journal of Lipid Research, p. 2060-2068, vol. 35, 1994.
McCutcheon's Emulsifiers & Detergents, North American Edition (1986), published by McCutcheon's Division, Mc Publishing Co., 175 Rock Rd, Glen Rock, NJ 07452, USA.
McCutcheon's Volume 2: Functional Material, North American Edition (1992), published by McCutcheon's Division, The Manufacturing Confectioner Publishing Co., 175 Rock Rd, Glen Rock, NJ 07452, USA.
Non-Final Office Action for co-pending U.S. Appl. No. 14/809,321, dated Sep. 30, 2019.

\* cited by examiner

COMPOSITIONS AND DISPERSIONS CONTAINING PARTICLES COMPRISING A POLYMER

FIELD OF THE INVENTION

The present invention relates to aqueous dispersions, compositions containing these dispersions and methods of using these dispersions and compositions on various substrates. More particularly, the aqueous dispersion comprises a particle, a surfactant mixture comprising a nonionic surfactant and an ionic surfactant, and water.

BACKGROUND OF THE INVENTION

Consumer products such as cosmetics, personal care, and household products, as well as pharmaceutical and industrial products, employ ingredients that allow these products to form a film or coating on various substrates such as keratinous substrates (e.g., hair and skin), hard surfaces (e.g., wood and metal), and other non-keratinous substrates, (e.g., fabrics and articles). Those ingredients which help form a film or coating on the surface of a substrate may be chosen from a variety of raw materials such as waxes, polymers, resins and oils. At the same time, products which employ these ingredients are designed to impart certain desirable properties such as shine, water resistance, transfer resistance, scratch resistance, color and a glazed appearance to a surface.

In particular, waxes and oils are highly desirable in cosmetics and personal care products as well as in household/industrial products in order to provide properties such as shine, smoothness, and slipperiness to various types of surfaces, as well as a protective coating against external factors such as exposure to water or moisture and physical rubbing. In the area of cosmetics, hair styling products which contain one or more of the abovementioned ingredients can be used to impart shape or style to the hair and/or to help maintain a particular hair style. Makeup cosmetic products which employ these ingredients are used to enhance the appearance of the skin, lips and eyelashes. For example, mascara products employ waxes and polymers, such as film forming polymers, which help shape or curl the eyelashes. Sunscreen products and other cosmetics can also use these ingredients to provide a water-resistant film or coating on the skin and hair, and also to help maintain the appearance and condition of skin and hair under extreme environmental conditions. In addition, these ingredients can provide structure and texture to the products and a certain feel and texture to a substrate.

Nevertheless, consumers continuously seek new products with improved performance and therefore, challenges still exist today in terms of optimizing or enhancing the performance of these ingredients in various products. Moreover, the formulation of waxes, polymers, resins and oils in various galenic forms such as sprays, foams, emulsions, gels, mousses, pastes and sticks may pose a challenge since some of these ingredients may not be easily introduced and/or dispersed into these galenic forms. In addition, the final formulas using these ingredients have to remain stable over time.

For example, waxes are traditionally employed in a paste or pomade but may not be easily formulated in a spray or foam product, particularly at a concentration that will be sufficient to impart the desirable attributes obtained from a wax ingredient. The type of wax may also affect the stability and dispersion of the wax particles in the formulation since wax particles could agglomerate. Certain waxes may also result in an undesirable rough texture and/or sticky and tacky feel of the product and/or to the treated substrate.

It is also necessary to find a means of thickening liquid compositions containing wax and oil ingredients. Compositions containing these ingredients very often conventionally display a tacky and/or undesirable pasty nature (lacking creaminess), which may be induced by insufficient gelling or by excessive thickening of the oils and waxes. Thus, it is desirable that the viscosity of the compositions is not too liquid (not too runny or watery) such that they easily drip or run off a substrate and not too thick such that they are difficult to apply and spread uniformly on a substrate. At the same time, it is desirable that the deposition onto a substrate such as skin and hair, does not give rise to a greasy sensation or a sensation of dryness or tautness.

In other words, formulating with waxes, polymers, resins and oils still poses a challenge with respect to optimizing the benefits that can be obtained from these ingredients themselves. Thus, there still exists a need to improve how such ingredients can be formulated into various galenic forms, and at the same time, optimize the benefits derived from these ingredients and enhance the performance of other ingredients such as cosmetic active ingredients, colorants, and sunscreen agents.

Thus, various technologies directed towards the use of waxes, polymers, resins and oils have been developed. For example, shape memory polymers (SMPs) have been found to have the ability to change shape and therefore, provide certain materials made of such polymers with the ability to change their shapes or revert back to their original shape upon deformation, particularly, when an external stimuli such as heat or light is applied; SMPs may be used in packaging films, fabrics and medical devices (Marc Biehl and Andreas Lendlein (2007). *Shape Memory Polymers, Materials Today*. 10 (4), pp. 20-28). In the area of cosmetics and hair care, US20080311050 and US20070275020 teach the use of shape memory polymers in hair treatment compositions. However, SMPs are typically complex polymer systems which may pose challenges in synthesis procedures and formulation in terms of the choice of solvents and delivery/galenic form.

Other teachings, such as DE2810130, disclose applying a polyamide powder onto hair and heating the hair to bond the hair in a particular style; however, this reference does not teach that the hair can be re-styled or re-positioned and appears to be directed to wigs. WO8904653 and WO8901771 disclose the use of heat-activated hair styling compositions containing water-soluble polyethylene oxide polymers. EP1174113, U.S. Pat. No. 7,998,465 and US20120070391 are directed to the use of specific polymers, including thermofusible polymers, heat-expandable particles comprising certain polymers, and polysiloxanes and silanes. However, the use of polymers may still result in sticky formulas, may be difficult to formulate into a stable dispersion as a result of compatibility issues with surfactants, and do not necessarily provide a long lasting effect on the hair or the ability to easily re-style or re-position the hair without reapplying a product, for example.

U.S. Pat. No. 7,871,600, U.S. Pat. No. 6,066,316, JP2003012478, US20060292095 and US20060263438 teach the preparation of wax and oil dispersions in hair cosmetic compositions. For instance, U.S. Pat. No. 7,871,600 teaches the use of a wax dispersion in a hair styling composition. However, said composition additionally requires a styling polymer and a relatively high amount of wax of from 30% to 45% by weight of the composition. U.S.

Pat. No. 6,066,316 discloses fine wax dispersions containing wax, an amphoteric surfactant and a nonionic surfactant where the size of the wax particles is about 30 nm and the nonionic surfactant is directed towards a specific class, i.e., polyoxypropylene alkyl ethers. JP2003012478 teaches a hair composition with hair-remodelling properties comprising an oil soluble material, a nonionic surfactant and water; the oil soluble material contains fatty acid, higher alcohol and wax. US20060292095 and US20060263438 disclose dispersions of oil particles of mean sizes that are 20 microns or less and for use in sunscreen and skin care compositions. Nevertheless, the preparation of wax and oil particle dispersions and formulating with these dispersions in various galenic forms may still pose challenges, particularly since there are a number of factors to consider when working with wax and oil particles such as size, shape, hardness and melting point. Another consideration is the challenge of finding a convenient and easy way of optimizing the benefits provided by certain ingredients or raw materials.

For example, the ability to provide hair styling/shaping products to help maintain the shape of hair or to re-position/re-style the hair without reapplication of product, to provide humidity resistance and impart other desirable properties to hair such as shine, conditioning, softness and combability as well while having good aesthetic features remain as additional areas for improvement, particularly in connection with the use of waxes and oils in such products.

Thus, it is an object of the present invention to provide a composition containing a dispersion material comprising particles having certain physical properties. It is also an object of the present invention to provide a novel way of imparting certain desirable properties to the surface of a substrate, in particular, keratinous substrates, using the dispersion material and/or compositions containing the dispersion material.

BRIEF SUMMARY OF THE INVENTION

The present invention relates to an aqueous dispersion containing:
  (a) particles having a volume-basis particle size distribution with peaks in the range of equal to or greater than 1 μm up to about 100 μm and comprising:
    (i) an oil gellant comprising at least one styrenic block copolymer;
    (ii) a fatty substance selected from at least one wax having a melting point of greater than 35° C., at least one oil, and mixtures thereof; and
    (iii) optionally, at least one additional ingredient selected from an oil gellant other than a)(i), colorants, sunscreen agents, a wax having a melting point of 35° C. or less, fragrance oils, emulsifying polymers, silicas, talc, clays, and mixtures thereof;
  (b) a surfactant mixture comprising:
    (i) at least one nonionic surfactant; and
    (ii) at least one ionic surfactant; and
  (c) water.

The present invention also relates to a composition containing:
A. an aqueous dispersion comprising:
  (a) particles having a volume-basis particle size distribution with peaks in the range of equal to or greater than 1 μm up to about 100 μm and comprising:
    (i) an oil gellant comprising at least one styrenic block copolymer;
    (ii) a fatty substance selected from at least one wax having a melting point of greater than 35° C., at least one oil, and mixtures thereof; and
    (iii) optionally, at least one additional ingredient selected from an oil gellant other than a)(i), colorants, sunscreen agents, a wax having a melting point of 35° C. or less, fragrance oils, emulsifying polymers, silicas, talc, clays, and mixtures thereof;
  (b) a surfactant mixture comprising:
    (i) at least one nonionic surfactant; and
    (ii) at least one ionic surfactant; and
  (c) water; and
B. a carrier comprising water, volatile organic solvents, non-volatile organic solvents, silicones, non-silicone oils, and mixtures thereof.

The above-composition can further comprise at least one auxiliary ingredient selected from selected from liquid lipids/oils, waxes, film forming polymers, rheology modifiers, humectants and moisturizing agents, emulsifying agents, structuring agents, propellants, surfactants, shine agents, conditioning agents, cosmetically, dermatologically and pharmaceutically active agents, vitamins, plant extracts, and mixtures thereof.

Furthermore, the present invention also relates to methods of coating a substrate, such as keratinous substrates, said methods involving applying onto the substrate the above-described aqueous dispersion or composition containing the aqueous dispersion and carrier, and optionally, applying heat to the substrate. In particular, the present invention relates to a method of styling hair involving applying to the hair the above-described dispersion or composition containing the aqueous dispersion and carrier, and applying heat to the hair.

DETAILED DESCRIPTION OF THE INVENTION

Figure 1:
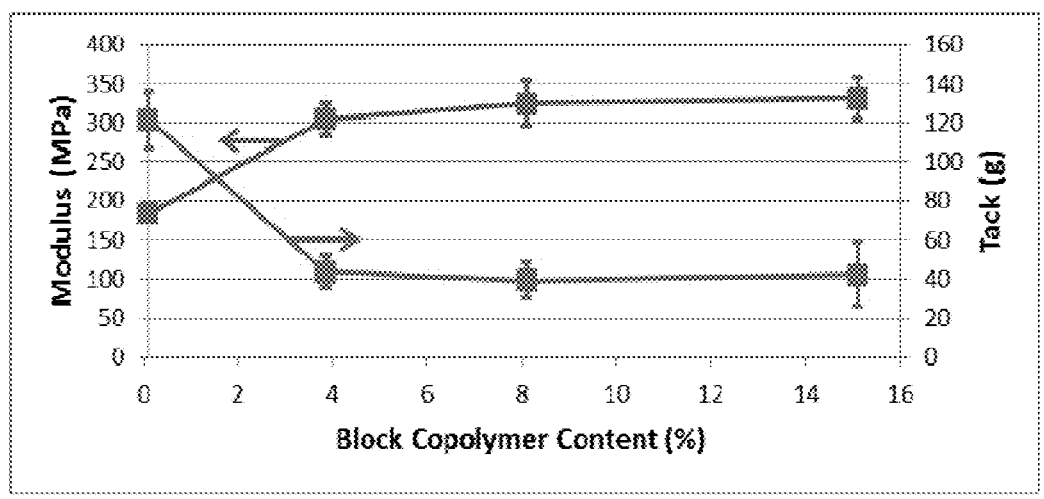
FIG. 1 represents a chart showing tack and modulus measurements made for a wax-styrenic block copolymer mixture and a wax.

As used herein, the expression "at least one" means one or more and thus includes individual components as well as mixtures/combinations.

It is also to be understood that, as used herein the terms "the," "a," or "an," mean "at least one," are understood to encompass the plural as well as the singular and should not be limited to "only one" unless explicitly indicated to the contrary. Thus, for example, the use of "a surfactant" is intended to mean at least one surfactant.

The term "comprising" (and its grammatical variations) as used herein is used in the inclusive sense of "having" or "including" and not in the exclusive sense of "consisting only of".

"Keratinous substrates" as used herein, include, but are not limited to skin, lips, scalp, and keratinous fibers such as hair and eyelashes.

"Wax" as used herein means a hydrocarbon material, natural or synthetic, and having a melting point in the ranges disclosed below. Polymers and copolymers are included in this definition. Wax as used herein may also include a material composed of several components, including wax esters such as those derived from carboxylic acids and fatty alcohols, wax alcohols, and hydrocarbons.

The terms "gelation" or "gelling" or variations of these terms mean structuring or, more generally, thickening of the medium, which may lead according to the invention to a fluid or creamy or even solid consistency.

"Film former" or "film forming agent" as used herein means a polymer or resin that leaves a film on the substrate to which it is applied, for example, after a solvent accompanying the film former has evaporated, absorbed into and/or dissipated on the substrate. These terms may also refer to a polymer capable, by itself or in the presence of an auxiliary film-forming agent, of forming a continuous or a discontinuous film that adheres to a support and especially to keratin substrates.

"Volatile", as used herein, means having a flash point of less than about 100° C.

"Non-volatile", as used herein, means having a flash point of greater than about 100° C.

"Substituted" as used herein, means comprising at least one substituent. Non-limiting examples of substituents include atoms, such as oxygen atoms and nitrogen atoms, as well as functional groups, such as acyloxyalky groups, carboxylic acid groups, amine or amino groups, acylamino groups, amide groups, halogen containing groups, ester groups, thiol groups, sulphonate groups, thiosulphate groups, siloxane groups, and polysiloxane groups. The substituent(s) may be further substituted.

As used herein, the phrase "salts and derivatives thereof" is intended to mean all salts and derivatives comprising the same functional structure as the compound they are referring to, and that have similar properties.

The terms "organic compound" and "having an organic structure" mean compounds containing carbon atoms and hydrogen atoms and optionally heteroatoms such as S, O, N or P, alone or in combination.

As used herein, the term "applying a composition onto a substrate" and variations of this phrase are intended to mean contacting the substrate, for example, a keratinous substrate such as skin or hair, with at least one of the compositions of the invention, in any manner.

As used herein, "formed from," means obtained from chemical reaction of, wherein "chemical reaction," includes spontaneous chemical reactions and induced chemical reactions. As used herein, the phrase "formed from," is open ended and does not limit the components of the composition to those listed.

The term "stable" as used herein means that the composition does not exhibit phase separation and/or crystallization.

The term "treat" (and its grammatical variations) as used herein refers to the application of the aqueous dispersion and compositions containing the dispersion onto the surface of a substrate.

The term "shaping" (and its grammatical variations) as used herein includes styling or placing a keratinous fiber such as hair, in a particular arrangement, form or configuration; or altering the curvature of a keratinous fiber or other substrate; or re-positioning a keratinous fiber or other substrate to a different arrangement, form or configuration.

The compositions and methods of the present invention can comprise, consist of, or consist essentially of the essential elements and limitations of the invention described herein, as well as any additional or optional ingredients, components, or limitations described herein or otherwise useful.

In an embodiment, the present invention relates to a composition containing:

A. an aqueous dispersion comprising:
  (a) particles having a volume-basis particle size distribution with peaks in the range of about 20 μm up to about 70 μm and comprising:
    (i) from about 0.1% to about 15% by weight of an oil gellant comprising at least one styrenic block copolymer selected from a styrene-ethylene/butylene diblock copolymer, a styrene-ethylene/butylene-styrene triblock copolymer, and mixtures thereof;
    (ii) from about 10% to about 60% by weight of a fatty substance comprising at least one wax having a melting point of greater than 35° C.; and
    (iii) optionally, at least one additional ingredient selected from an oil gellant other than a)(i), colorants, sunscreen agents, a wax having a melting point of 35° C. or less, fragrance oils, emulsifying polymers, silicas, talc, clays, and mixtures thereof.
  (b) a surfactant mixture comprising:
    (i) at least one nonionic surfactant; and
    (ii) at least one ionic surfactant; and
  (c) water;
all weights being based on the total weight of the aqueous dispersion;
B. a carrier comprising water, volatile organic solvents, non-volatile organic solvents, silicones, non-silicone oils, and mixtures thereof; and
C. optionally, at least one auxiliary ingredient selected from liquid lipids/oils, waxes, film forming polymers, rheology modifiers, humectants and moisturizing agents, emulsifying agents, structuring agents, propellants, surfactants, shine agents, conditioning agents, cosmetically, dermatologically and pharmaceutically active agents, vitamins, plant extracts, and mixtures thereof.

In an embodiment, the present invention relates to a composition containing:

A. an aqueous dispersion comprising:
  (a) particles having a volume-basis particle size distribution with peaks in the range of about 20 μm up to about 70 μm and comprising:
    (i) from about 0.1% to about 15% by weight of an oil gellant comprising at least one styrenic block copolymer selected from a styrene-ethylene/butylene diblock copolymer, a styrene-ethylene/butylene-styrene triblock copolymer, and mixtures thereof;
    (ii) a fatty substance comprising at least one oil; and
    (iii) optionally, at least one additional ingredient selected from an oil gellant other than a)(i), colorants, sunscreen agents, a wax having a melting point of 35° C. or less, fragrance oils, emulsifying polymers, silicas, talc, clays, and mixtures thereof.
  (b) a surfactant mixture comprising:
    (i) at least one nonionic surfactant; and
    (ii) at least one ionic surfactant; and
  (c) water;
all weights being based on the total weight of the aqueous dispersion;
B. a carrier comprising water, volatile organic solvents, non-volatile organic solvents, silicones, non-silicone oils, and mixtures thereof; and
C. optionally, at least one auxiliary ingredient selected from liquid lipids/oils, waxes, film forming polymers, rheology modifiers, humectants and moisturizing agents, emulsifying agents, structuring agents, propellants, surfactants, shine agents, conditioning agents, cosmetically, dermatologically and pharmaceutically active agents, vitamins, plant extracts, and mixtures thereof.

In an embodiment, the present invention relates to a composition containing:

A. an aqueous dispersion comprising:
  (a) particles having a volume-basis particle size distribution with peaks in the range of about 20 µm up to about 70 µm and comprising:
    (i) from about 0.1% to about 15% by weight of an oil gellant comprising at least one styrenic block copolymer selected from a styrene-ethylene/butylene diblock copolymer, a styrene-ethylene/butylene-styrene triblock copolymer, and mixtures thereof;
    (ii) a fatty substance comprising at least one wax having a melting point of greater than 35° C. and at least one oil; and
    (iii) optionally, at least one additional ingredient selected from an oil gellant other than a)(i), colorants, sunscreen agents, a wax having a melting point of 35° C. or less, fragrance oils, emulsifying polymers, silicas, talc, clays, and mixtures thereof;
  (b) a surfactant mixture comprising:
    (i) at least one nonionic surfactant; and
    (ii) at least one ionic surfactant; and
  (c) water;
all weights being based on the total weight of the aqueous dispersion;

B. a carrier comprising water, volatile organic solvents, non-volatile organic solvents, silicones, non-silicone oils, and mixtures thereof; and C. optionally, at least one auxiliary ingredient selected from liquid lipids/oils, waxes, film forming polymers, rheology modifiers, humectants and moisturizing agents, emulsifying agents, structuring agents, propellants, surfactants, shine agents, conditioning agents, cosmetically, dermatologically and pharmaceutically active agents, vitamins, plant extracts, and mixtures thereof.

In one embodiment, the present invention relates to an aqueous dispersion comprising:
  (a) particles having a volume-basis particle size distribution with peaks in the range of about 20 µm up to about 70 µm and comprising:
    (i) from about 0.1% to about 15% by weight of an oil gellant comprising at least one styrenic block copolymer selected from a styrene-ethylene/butylene diblock copolymer, a styrene-ethylene/butylene-styrene triblock copolymer, and mixtures thereof;
    (ii) from about 10% to about 60% by weight of a fatty substance selected from at least one wax having a melting point of greater than 35° C. selected from beeswax, hydrogenated myristyl olive esters, hydrogenated stearyl olive esters, VP/eicosene copolymer, ditrimethyloylpropane tetrastearate, and C30-45 alkyldimethylsilyl propylsilsesquioxane, and mixtures thereof; and
    (iii) optionally, at least one additional ingredient selected from an oil gellant other thant a)(i), colorants, sunscreen agents, a wax having a melting point of 35° C. or less, emulsifying polymers, fragrance oils, silicas, talc, clays, and mixtures thereof;
  (b) from about 1% to about 5% by weight of a surfactant mixture comprising:
    (i) at least one nonionic surfactant selected from PEG-30 glyceryl stearate, sorbitan palmitate, Cetyl PEG/PPG-10/1 Dimethicone, Bis-PEG/PPG-16/16 PEG/PPG-16/16 Dimethicone, Bis-PEG/PPG-20/5 PEG/PPG-20/5 Dimethicone, PEG/PPG-25/4 Dimethicone, Bis-(Glyceryl/Lauryl) Glyceryl Lauryl Dimethicone, Bis-PEG/PPG-14/14 Dimethicone, and mixtures thereof; and
    (ii) at least one ionic surfactant; and
  (c) water;
all weights being based on the total weight of the aqueous dispersion.

In one embodiment, the ionic surfactant in the above described dispersion is an anionic surfactant selected from dipalmitoylethyl hydroxyethylmonium methosulfate, distearoylethyl hydroxyethylmonium methosulfate, disodium stearoyl glutamate and sodium stearoyl glutamate, and mixtures thereof.

In one embodiment, the ionic surfactant in the above described dispersion is a cationic surfactant selected from cetrimonium chloride, behentrimonium chloride, and mixtures thereof.

In an embodiment, the above-described compositions can optionally contain at least one auxiliary ingredient selected from selected from liquid lipids/oils, waxes, film forming polymers, rheology modifiers, humectants and moisturizing agents, emulsifying agents, structuring agents, propellants, surfactants, shine agents, conditioning agents, cosmetically, dermatologically and pharmaceutically active agents, vitamins, plant extracts, and mixtures thereof.

In certain embodiments, the above-described aqueous dispersions further comprises an oil gellant other than the oil gellant comprising at least one styrenic block copolymer chosen from semi-crystalline polymers, glutamide-based compounds, polyamides, and mixtures thereof.

The particles of the aqueous dispersions of the present invention may be heat-activated. Thus, the present invention also relates to methods of coating a substrate, such as keratinous substrates, said methods involving applying onto the substrate any one of the above-described aqueous dispersions or compositions containing the aqueous dispersions and carrier, and applying heat to the substrate.

In a preferred embodiment, the present invention relates to methods of shaping hair, said methods involving applying onto the hair any one of the above-described aqueous dispersions or compositions containing the aqueous dispersions and carrier, applying heat to the substrate, and optionally, using a means for shaping hair in order to shape the hair.

In one embodiment, the present invention relates to compositions for treating oily skin, hair or scalp and for making up or caring for the skin, hair or scalp.

In an embodiment, the present invention is also related to compositions containing any one of the above-described aqueous dispersions and the above-described carrier wherein the aqueous dispersion is obtained through any one of the processes or protocols described herein such that the particles comprising the aqueous dispersion have a volume-basis particle size distribution with peaks in the range of equal to or greater than 1 µm up to about 100 µm, such as from between about 10 µm up to about 80 µm, or from between about 20 µm up to about 80 µm, or from between about 40 µm up to about 65 µm, or from between about 45 µm up to about 65 µm, or from between equal to or greater than 1 µm up to about 20 µm.

It was surprisingly and unexpectedly discovered that the particles of the aqueous dispersion of the present disclosure can be prepared in a controlled or calibrated manner by using a surfactant mixture that employs a combination of a nonionic surfactant and an ionic surfactant and following an emulsification process. As a result, a fine dispersion of particles with minimal coalescence or agglomeration can be obtained. Moreover, the particles in the aqueous dispersion of the present disclosure can be homogeneous with respect to their shape.

It was surprisingly and unexpectedly discovered that the aqueous dispersions of the present disclosure had reduced or minimized stickiness or tackiness which are undesirable properties generally attributed to the presence of waxes and/or oils.

Furthermore, the aqueous dispersion of the present disclosure can be formulated into compositions of various galenic forms such as gels, mousses, lotions, creams, pastes, ointments, sprays and foams. It was found that when the aqueous dispersion of the present disclosure was added into one of these galenic forms, the particles remained homogeneously and finely dispersed in the composition and said composition is stable even during storage and exhibits no agglomeration or precipitation of the particles. It was also surprisingly and unexpectedly discovered that the compositions had reduced or minimized stickiness or tackiness which are undesirable product properties generally attributed to the presence of waxes and/or oils.

The aqueous dispersion of the present disclosure and compositions containing the aqueous dispersion can be applied onto various substrates to form a film or coating on the surface of the substrate. It was surprisingly and unexpectedly discovered that the film or coating on the surface of the substrate had no or minimal stickiness or tackiness; in addition, the film or coating was thin and uniform and was not brittle i.e., it did not easily break.

The aqueous dispersion of the present disclosure and compositions containing the aqueous dispersion also imparted a clean and natural feel on the substrate, despite the presence of wax and/or oil. For example, when the composition containing the aqueous dispersion of the present disclosure was applied onto a keratinous substrate such as hair, the film or coating formed on the hair was not brittle and did not undesirably stiffen the hair or cause the hair fibers to be glued or stuck together. Instead, it was found that there was a natural feel to the hair, i.e., the film or coating was not heavy and/or thick.

It was also surprisingly and unexpectedly found that when the substrate having the above-described film or coating is exposed to heat, additional benefits to the substrate are achieved such as better and longer-lasting adhesion (or durability) and re-shapeability in the case of a flexible or bendable substrate such as hair. It was also found that the coated substrate may undergo further re-shaping and re-positioning when it is re-heated without the need for reapplication of the aqueous dispersion or composition containing the aqueous dispersion of the present disclosure.

Moreover, while the aqueous dispersion and compositions containing the aqueous dispersion imparted a coating or film onto a substrate, said dispersion and compositions may easily be removed from the substrate by washing with water or with conventional cleansing agents.

Although not wishing to be bound by any particular theory, it is believed that upon applying the aqueous dispersion of the present invention onto a substrate in conjunction with heating the substrate the particles melt or soften, thereby allowing for the film or coating to be re-positioned on the substrate and/or to adhere better and longer to the substrate.

The aqueous dispersion and compositions of the present disclosure are also useful in cosmetic applications for skin, lips, nails, and eyelashes such as makeup, skin care and sun care products, particularly, in allowing beneficial ingredients in these products to remain longer on these substrates as a result of the film or coating formed on the substrates.

Aqueous Dispersion

The aqueous dispersion of the present disclosure contains particles comprising an oil gellant comprising at least one styrenic block copolymer and a fatty substance selected from at least one wax having a melting point greater than 35° C., at least one oil, and mixtures thereof.

The term "fatty substance" means an organic compound that is insoluble in water at ordinary temperature (25° C.) and at atmospheric pressure (760 mmHg) (solubility of less than 5%, preferably less than 1% and even more preferentially less than 0.1%). They exhibit, in their structure, at least one hydrocarbon chain comprising at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane. The fatty substances of the invention do not contain any salified or unsalified carboxylic acid groups (COOH or COO—).

As used in the present invention, the term "fatty phase" refers to an oil or a mixture of oils or a wax or mixture of wax(es) and oil(s).

Oil Gellant

The at least one oil gellant of the present invention comprises at least one styrenic block copolymer.

Styrenic Block Copolymer

For the purposes of the present invention, the term "polymer" is intended to denote compounds comprising at least two repeating units, preferably at least three repeating units and especially at least 10 repeating units.

The styrenic block copolymer of the invention is a hydrocarbon-based block copolymer which is preferably soluble or dispersible in a fatty phase or mixture containing fatty substances. In the present disclosure, the fatty substances are chosen from oils and waxes. The styrenic block copolymer is capable of thickening or gelling the fatty phase or mixture containing fatty substances.

Preferably, the styrenic block copolymer is an amorphous polymer, which means a polymer that does not have a crystalline form. Such a compound has film-forming properties, i.e. it is capable of forming a film when applied to the skin.

Preferably, the styrenic block copolymer is obtained from at least one styrene monomer.

The styrenic block copolymer may especially be a diblock, triblock, multiblock, radial or star copolymer, or mixtures thereof.

Such styrenic block copolymer are described in patent application US-A-2002/005 562 and in U.S. Pat. No. 5,221,534.

The copolymer may contain at least one block whose glass transition temperature is preferably less than 20° C., preferably less than or equal to 0° C., preferably less than or equal to −20° C. and more preferably less than or equal to −40° C. The glass transition temperature of the said block may be between −150° C. and 20° C. and especially between −100° C. and 0° C.

The styrenic block copolymer present in the composition according to the invention is an amorphous copolymer formed by polymerization of an olefin. The olefin may especially be an elastomeric ethylenically unsaturated monomer.

Examples of olefins that may be mentioned include ethylenic carbide monomers, especially containing one or two ethylenic unsaturations and containing from 2 to 5 carbon atoms, such as ethylene, propylene, butadiene, isoprene or pentadiene.

Advantageously, the styrenic block copolymer is an amorphous block copolymer of styrene and of olefin.

Block copolymers comprising at least one styrene block and at least one block comprising units chosen from butadiene, ethylene, propylene, butylene and isoprene or a mixture thereof are especially preferred. According to one preferred embodiment, the styrenic block copolymer is hydrogenated to reduce the residual ethylenic unsaturations after the polymerization of the monomers.

In particular, the styrenic block copolymer is a copolymer, optionally hydrogenated, containing styrene blocks and ethylene/C3-C4 alkylene blocks.

According to one preferred embodiment, the oil gellant comprising at least one styrenic block copolymer according to the invention comprises at least one diblock copolymer, which is preferably hydrogenated, preferably chosen from styrene-ethylene/propylene copolymers, styrene-ethylene butadiene copolymers and styrene-ethylene/butylene copolymers. The diblock polymers are especially sold under the name Kraton® GI 701 E by the company Kraton Polymers.

According to another preferred embodiment, the oil gellant comprising at least one styrenic block copolymer according to the invention comprises at least one triblock copolymer, which is preferably hydrogenated, preferably chosen from styrene-ethylene/propylene-styrene copolymers, styrene-ethylene/butadiene-styrene copolymers, styrene-isoprene-styrene copolymers and styrene-butadiene-styrene copolymers. Triblock polymers are especially sold under the names Kraton® G1650, Kraton® G1652, Kraton® G1657, Kraton® DI 101, Kraton® DI 102 and Kraton® DI 160 by the company Kraton Polymers.

According to one embodiment of the present invention, the at least one styrenic block copolymeris a diblock copolymer chosen from styrene-ethylene/butylene diblock copolymer, styrene-ethylene/propylene diblock copolymer, and mixtures thereof.

According to another embodiment of the present invention, the at least one styrenic block copolymer is a styrene-ethylene/butylene-styrene triblock copolymer.

According to one preferred embodiment of the invention, it is especially possible to use a mixture of a styrene-ethylene/butylene-styrene triblock copolymer and of a styrene-ethylene/butylene diblock copolymer, especially the products sold under the name Kraton® G1657M or Kraton® G1657MS by the company Kraton Polymers.

According to another preferred embodiment of the invention, it is possible to use a mixture of styrene-butylene/ethylene-styrene hydrogenated triblock copolymer and of ethylene-propylene-styrene hydrogenated star polymer, such a mixture possibly being especially in isododecane or in another oil. Such mixtures are sold, for example, by the company Penreco under the trade names Versagel® M5960 and Versagel® M5670.

In particularly preferred embodiments of the present invention, a mixture of styrene-ethylene/butylene-styrene triblock copolymer and styrene-ethylene/butylene diblock copolymer is used. Preferably, the percent amount of the triblock colpolymer is greater than the percent amount of the diblock polymer in the mixture, based on the total weight of the mixture. For example, the mixture can contain 70% by weight of the triblock copolymer and 30% by weight of the diblock copolymer. Such a mixture is available by the INCI name hydrogenated styrene/butadiene copolymer, sold under the tradename Kraton® G1657M or Kraton® G1657MS by the company Kraton Polymers.

The content of styrenic block copolymer in accordance with the invention may range from about 0.1% to about 15% by weight, preferably from about 0.5% to about 10% by weight, more preferably from about 1% to about 8% by weight, and even more preferably from about 1% to about 5% by weight based on the total weight of the aqueous dispersion, including all ranges and subranges therebetween.

The styrenic block copolymer is generally comprised of hard and soft domains. When blended with other materials, such as waxes and/or oils, to form the particles of the present disclosure, it was surprisingly and unexpectedly found that the compositions containing such particles provided the benefits of increased flexibility and toughness, while providing a clean and natural touch to the hair. In addition, improved shape memory, body, bounce and movement to hair compared to the use of wax alone can be obtained.

The at least one oil gellant of the present invention can also comprise at least one additional oil gellant other than the oil gellant comprising at least one styrenic block copolymer. The additional oil gellant may be chosen from semi-crystalline polymers, a glutamide-based compound, a polyamide, and mixtures thereof.

Semi-Crystalline Polymer

For the purposes of the invention, the term "semi-crystalline polymer" means polymers comprising a crystallizable portion and an amorphous portion and having a first-order reversible change of phase temperature, in particular of melting (solid-liquid transition). The crystallizable portion is either a side chain (or pendent chain) or a block in the backbone.

When the crystallizable portion of the semi-crystalline polymer is a block of the polymer backbone, this crystallizable block has a chemical nature different from that of the amorphous blocks; in this case, the semi-crystalline polymer is a block copolymer, for example of the diblock, triblock or multiblock type. When the crystallizable portion is a chain that is pendent on the backbone, the semi-crystalline polymer may be a homopolymer or a copolymer.

The semi-crystalline polymer(s) according to the invention are solid at room temperature (25° C.) and atmospheric pressure (760 mmHg).

Preferably, the semi-crystalline polymer has an organic structure and a melting point of greater than or equal to 30° C. and preferably less than 150° C. More preferably, the melting point of the semi-crystalline polymer is less than 100° C., such as less than 70° C.

The melting point values correspond to the melting point measured using a differential scanning calorimeter (DSC). (The melting point under consideration is the point corresponding to the temperature of the most endothermic peak of the thermogram).

The semi-crystalline polymer(s) according to the invention preferably have a melting point that is higher than the temperature of the keratinous support intended to be contacted with the aqueous dispersions and compositions of the present invention, in particular, the skin or the hair or the scalp.

According to the invention, the semi-crystalline polymers are advantageously soluble or dispersible in a fatty phase or mixture containing fatty substances as described above, especially to at least 1% by weight, at a temperature that is higher than their melting point.

Within the meaning of the invention, the expression "crystallizable chain or block" is understood to mean a chain or block which, if it were alone, would change from the amorphous state to the crystalline state reversibly, according to whether the temperature is above or below the melting point. Within the meaning of the invention, a "chain" is a group of atoms, which is pendent or lateral with respect to the backbone of the polymer. A block is a group of atoms belonging to the backbone, this group constituting one of the repeat units of the polymer.

Preferably, the polymer backbone of the semi-crystalline polymers is soluble in the fatty phase or mixture containing fatty substances at a temperature above their melting point.

Preferably, the crystallizable blocks or chains of the semi-crystalline polymers represent at least 30% of the total weight of each polymer and better still at least 40%. The semi-crystalline polymers containing crystallizable side chains are homopolymers or copolymers. The semi-crystalline polymers of the invention containing crystallizable blocks are block or multiblock copolymers. They may be obtained via polymerization of a monomer containing reactive double bonds (or ethylenic bonds) or via polycondensation. When the polymers of the invention are polymers having crystallizable side chains, these side chains are advantageously in random or statistical form.

Preferably, the semi-crystalline polymers of the invention are of synthetic origin.

According to one preferred embodiment, the semi-crystalline polymer is chosen from: homopolymers and copolymers comprising units resulting from the polymerization of one or more monomers bearing crystallizable hydrophobic side chain(s); polymers bearing in the backbone at least one crystallizable block; polycondensates of aliphatic or aromatic or aliphatic/aromatic polyester type; and copolymers of ethylene and propylene prepared via metallocene catalysis.

A) Semi-Crystalline Polymers Containing Crystallizable Side Chains

The polymers and copolymers are particularly preferably chosen from semi-crystalline polymers bearing crystallizable side chains. Mention may be made in particular of those defined in documents U.S. Pat. No. 5,156,911 and WO-A-01/19333.

They are homopolymers or copolymers comprising from 50% to 100% by weight of units resulting from the polymerization of one or more monomers bearing a crystallizable hydrophobic side chain.

These homopolymers or copolymers are of any nature, provided that they meet the conditions mentioned hereinbelow with, in particular, the characteristic of being soluble or dispersible in the fatty phase, by heating above their melting point (mp). They can result:
from the polymerization, in particular radical polymerization, of one or more monomers having reactive or ethylenic double bond(s) with respect to a polymerization, namely having a vinyl, (meth)acrylic or allylic group,
from the polycondensation of one or more monomers bearing co-reactive groups (carboxylic acid, sulfonic acid, alcohol, amine or isocyanate), for instance polyesters, polyurethanes, polyethers or polyureas.

In general, the crystallizable units (chains or blocks) of the semi-crystalline polymers according to the invention are derived from monomer(s) containing crystallizable block(s) or chain(s), used for manufacturing semi-crystalline polymers. These polymers are preferably chosen especially from homopolymers and copolymers resulting from the polymerization of at least one monomer containing crystallizable chain(s) that may be represented by formula X:

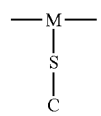

with M representing an atom of the polymer backbone, C representing a crystallizable group and S representing a spacer.

The "—S—C" crystallizable chains are optionally fluorinated or perfluorinated, hydrocarbon-based aliphatic or aromatic chains, comprising saturated or unsaturated C12-C40, preferably C12-C28 and preferably C14-C24 hydrocarbon-based alkyl chains.

"C" especially represents a group (CH2)n, which may be linear or branched or cyclic, with n being an integer ranging from 12 to 40. Preferably, "C" is a linear group. Preferably, "S" and "C" are different.

When the crystallizable chains are hydrocarbon-based aliphatic chains, they comprise hydrocarbon-based alkyl chains containing at least 12 carbon atoms and not more than 40 carbon atoms and better still not more than 24 carbon atoms. They are especially aliphatic chains or alkyl chains containing at least 12 carbon atoms, and they are preferably $C_{12}$-$C_{40}$, preferably $C_{12}$-$C_{28}$, preferably $C_{14}$-$C_{24}$ and preferably $C_{16}$-$C_{22}$ alkyl chains.

Preferably, the crystallizable chains are $C_{16}$-$C_{22}$ hydrocarbon-based aliphatic chains.

When they are fluoroalkyl or perfluoro alkyl chains, they comprise at least 11 carbon atoms, at least 6 of which carbon atoms are fluorinated.

Preferably, the semicrystalline polymers having a crystallizable side chain are alkyl (meth)acrylate or alkyl(meth) acrylamide homopolymers with an alkyl group as defined above, in particular a $C_{14}$-$C_{24}$ alkyl group, copolymers of these monomers with a hydrophilic monomer preferably different in nature from (meth)acrylic acid, such as N-vinylpyrrolidone or hydroxyethyl (meth)acrylate, and mixtures thereof.

Advantageously, the semi-crystalline polymer(s) containing a crystallizable side chain has (have) a weight-average molecular mass Mp ranging from 5000 to 1 000 000, preferably from 10 000 to 800 000, preferentially from 15 000 to 500 000 and more preferably from 100 000 to 200 000.

According to one particular embodiment of the invention, a polymer may be chosen from homopolymers and copolymers resulting from the polymerization of at least one monomer with a crystallizable side chain chosen from saturated $C_{10}$ to $C_{30}$ alkyl (meth)acrylates, which may be represented by the formula below:

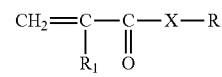

in which $R_1$ is H or $CH_3$, R represents a $C_{10}$ to $C_{30}$ alkyl group and X represents O.

According to a more particular embodiment of the invention, the polymer is derived from the polymerization of monomers bearing a crystallizable chain, chosen from saturated $C_{10}$ to $C_{30}$ alkyl (meth)acrylates.

As a particular example of a semi-crystalline polymer that may be used in the composition according to the invention, mention may be made of the Intelimer® products from the company Landec described in the brochure "Intelimer® polymers", Landec IP22 (Rev. 4-97). These polymers are in solid form at room temperature (25° C.). They bear crystallizable side chains and have the formula X above. They are poly($C_{10}$ to $C_{30}$)alkyl acrylates, which are particularly suitable as semi-crystalline polymers that may be included in a composition in accordance with the present invention.

The semi-crystalline polymers that may be used in the invention are in particular homopolymers or copolymers bearing at least one crystallizable side chain, such as those described in document U.S. Pat. No. 5,156,911, and mixtures thereof.

In preferred embodiments of the present invention, the semi-crystalline polymer is chosen from polystearyl acrylate, such as the product sold under the name Intelimer® IPA 13-1 from the company Air Products and Chemicals or Landec, and the polymer known under the INCI name Poly C10-30 alkyl acrylate and sold under the tradenamename Intelimer® IPA 13-6 from the company Air Products and Chemicals or Landec.

B) Polymers Having at Least One Crystallizable Block in the Polymer Backbone

These polymers are especially block copolymers consisting of at least two blocks of different chemical nature, one of which is crystallizable.

The polymer bearing at least one crystallizable block in the backbone may be chosen from block copolymers of olefin or of cycloolefin containing a crystallizable chain.

The polymer bearing at least one crystallizable block in the backbone may be chosen from copolymers containing at least one crystallizable block, the rest of the copolymer being amorphous (at room temperature). These copolymers can additionally exhibit two crystallizable blocks which are different in chemical nature.

C) Polycondensates of Aliphatic or Aromatic or Aliphatic/Aromatic Polyester Type The polyester polycondensates may be chosen from aliphatic polyesters. Their molecular mass is preferably greater than or equal to 200 and less than or equal to 10 000, and more preferably greater than or equal to 300 and less than or equal to 5000, preferably greater than or equal to 500 and greater than or equal to 2000 g/mol.

The polyester polycondensates are in particular chosen from polycaprolactones. In particular, the polycaprolactones may be chosen from e-caprolactone homopolymers. The homopolymerization may be initiated with a diol, especially a diol containing from 2 to 10 carbon atoms, such as diethylene glycol, 1,4-butanediol or neopentyl glycol.

Polycaprolactones may be used for example, especially those sold under the CAP A® tradename having varying melting points and molecular weights by the company Solvay, or PCL-300 and PCL-700 by the company Union Carbide. CAP A® 2125 (melting point is between 35 and 45° C. and molecular weight 1250) may be used in particular.

D) Copolymers of Ethylene and Propylene Prepared Via Metallocene Catalysis

The semi-crystalline polymer of the composition of the invention may also be a polymer obtained via metallocene catalysis, such as those described in patent US 2007/0031361.

These polymers are copolymers of ethylene and propylene prepared via metallocene catalysis, i.e. by polymerization at low pressure and in the presence of a metallocene catalyst.

The copolymers of ethylene and propylene prepared via metallocene catalysis may be unmodified or "polar"-modified (i.e. modified such that they contain polar groups).

In some embodiments, the polar-modified copolymers of ethylene and/or propylene prepared via metallocene catalysis are polymers modified such that they have hydrophilic properties. Examples that may be mentioned include ethylene and/or propylene homopolymers or copolymers modified by the presence of hydrophilic groups such as maleic anhydride, acrylate, methacrylate, polyvinylpyrrolidone (PVP), etc.

Examples that may be mentioned include: polypropylene polymers modified with maleic anhydride (PPMA) sold by the company Clariant, or polypropylene-ethylene-maleic anhydride copolymers, such as those sold by the company Clariant under the name LicoCare, for instance LicoCare PP207 LP3349, LicoCare CM401 LP3345, LicoCare CA301 LP3346 and LicoCare CA302 LP3347.

Glutamide-Based Compounds

The glutamide-based compounds of the present invention are known to comprise a type of organogelling agents. Preferably, the glutamide-based compounds of the present invention are non-polymeric.

According to the invention, an "organogelling agent" is defined as comprising an organic compound whose molecules may be capable of establishing, between themselves, at least one physical interaction leading to self-aggregation of the molecules with formation of a three-dimensional macromolecular network that may be responsible for the gelation of a liquid fatty phase or a mixture containing fatty substances.

Organogelling agents may also be called lipophilic gelling agents.

The glutamide-based compounds of the invention may be solid or liquid at room temperature (20° C.) and at atmospheric pressure.

Preferably, the glutamide-based compounds are non-polymeric and are chosen from: a low molecular weight dialkyl N-acylglutamide bearing a linear alkyl chain, chosen especially from di(C2-C6)alkyl N-acylglutamides in which the acyl group comprises a linear C8 to C22 alkyl chain, preferably such as lauroylglutamic acid dibutylamide (or dibutyl lauroyl glutamide), and/or a low molecular weight dialkyl N-acylglutamide bearing a branched alkyl chain, chosen especially from di(C2-C6)alkyl N-acylglutamides in which the acyl group comprises a branched Cg to C22 alkyl chain, preferably such as N-2-ethylhexanoylglutamic acid dibutylamide (or dibutyl ethylhexanoyl glutamide), and mixtures thereof.

Preferably, among the non-polymeric glutamide-based compounds that may be used are combinations of at least one low molecular weight dialkyl N-acylglutamide bearing a linear alkyl chain, chosen especially from (C2-C6)dialkyl N-acylglutamides in which the acyl group comprises a linear C8 to C22 alkyl chain such as lauroylglutamic acid dibutylamide (dibutyl lauroyl glutamide), with at least one low molecular weight dialkyl N-acylglutamide bearing a branched alkyl chain, chosen especially from (C2-C6)dialkyl N-acylglutamides in which the acyl group comprises a branched C8 to C22 alkyl chain such as N-2-ethylhexanoyl glutamic acid dibutylamide (dibutyl ethylhexanoyl glutamide) and preferably with a solvent that is capable of forming hydrogen bonds with these two glutamide-based compounds.

In preferred embodiments, the glutamide-based compound suitable for use in the present invention is Dibutyl Lauroyl Glutamide, known by the tradename GP-1 and sold by the company Ajinomoto.

Polyamides

The polyamides of the present invention may be chosen from hydrocarbon-based polyamides, silicone polyamides, and mixtures thereof.

For the purposes of the invention, the term "polyamide" means a compound containing at least two repeating amide units, preferably at least three repeating amide units and better still ten repeating amide units.

a) Hydrocarbon-Based Polyamide

The term "hydrocarbon-based polyamide" means a polyamide formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

For the purposes of the invention, the term "functionalized chains" means an alkyl chain comprising one or more functional groups or reagents chosen especially from hydroxyl, ether, esters, oxyalkylene and polyoxyalkylene groups.

Advantageously, the polyamide of the invention has a weight-average molecular mass of less than 100 000 g/mol (especially ranging from 1000 to 100 000 g/mol), in particular less than 50 000 g/mol (especially ranging from 1000 to 50 000 g/mol) and more particularly ranging from 1000 to 30 000 g/mol, preferably from 2000 to 20 000 g/mol and better still from 2000 to 10 000 g/mol.

This polyamide is insoluble in water, especially at 25° C.

According to a first embodiment of the invention, the polyamide used is a polyamide of formula (I):

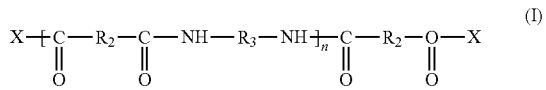

(I)

in which X represents a group —N(R$_1$)$_2$ or a group —OR$_1$ in which R$_1$ is a linear or branched C$_8$ to C$_{22}$ alkyl radical which may be identical or different, R$_2$ is a C$_{28}$-C$_{42}$ diacid dimer residue, R$_3$ is an ethylenediamine radical and n is between 2 and 5; and mixtures thereof;

According to a particular mode, the polyamide used is an amide-terminated polyamide of formula (Ia)

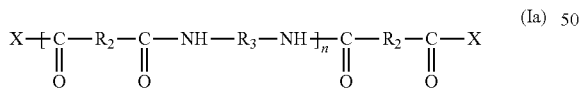

(Ia)

in which X represents a group —N(R$_1$)$_2$ in which ft is a linear or branched C$_8$ to C$_{22}$ alkyl radical which may be identical or different, R$_2$ is a C$_{28}$-C$_{42}$ diacid dimer residue, R$_3$ is an ethylenediamine radical and n is between 2 and 5; and mixtures thereof;

At least one additional polyamide of formula (Ib) may also be used:

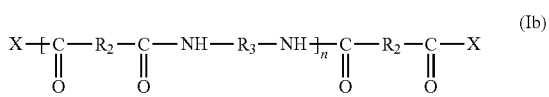

(Ib)

in which X represents a group —OR$_1$ in which R$_1$ is a linear or branched C$_8$ to C$_{22}$ and preferably C$_{16}$ to C$_{22}$ alkyl radical which may be identical or different, R$_2$ is a C$_{28}$-C$_{42}$ diacid dimer residue, R$_3$ is an ethylenediamine radical and n is between 2 and 5.

As examples of the polyamide compounds of formula (Ib), in which X represents a group —OR$_1$ in which R$_1$ is a linear or branched C$_8$ to C$_{22}$ and preferably C$_{16}$ to C$_{22}$ alkyl radical which may be identical or different, R$_2$ is a C$_{28}$-C$_{42}$ diacid dimer residue, R$_3$ is an ethylenediamine radical and n is between 2 and 5, mention may be made of the commercial products sold by the company Arizona Chemical under the names Uniclear 80 and Uniclear 100 or Uniclear 80 V, Uniclear 100 V and Uniclear 100 VG, the INCI name of which is Ethylenediamine/stearyl dimer dilinoleate copolymer. They are sold, respectively, in the form of a gel containing 80% active material in a mineral oil and at 100% active material. They have a softening point of from 88 to 94° C. These commercial products are a mixture of copolymers of a C$_{36}$ diacid coupled with ethylenediamine, having a weight-average molecular mass of about 6000 g/mol. The terminal ester groups result from the esterification of the remaining acid end groups with cetyl alcohol, stearyl alcohol or mixtures thereof (also known as cetylstearyl alcohol).

As examples of amide-terminated polyamide compounds such as those described in patent application US 2009/0280076, and in particular an amide-terminated polyamide of formula (Ia) in which X represents a group —N(R$_1$)$_2$ in which R$_1$ is a linear or branched C$_8$ to C$_{22}$, preferably C$_8$ to C$_{20}$, preferably C$_{14}$ to C$_{20}$ and more preferentially C$_{14}$ to C$_{18}$ and better still C$_{18}$ alkyl radical, which may be identical or different, R$_2$ is a C$_{28}$-C$_{42}$ diacid dimer residue, preferably a dilinoleic acid dimer residue, R$_3$ is an ethylenediamine radical, and n is between 2 and 5 and preferably between 3 and 4, mention may be made of the compound of formula (Ia) whose INCI name is bis-dioctadecylamide dimer dilinoleic acid/ethylenediamine copolymer.

As a specific example of an amide-terminated polyamide that may be used, mention may be made of the compound Haimalate PAM sold by the company Kokyu Alcohol Kogyo, which is in combination with diisostearyl malate and whose INCI name is diisostearyl malate (and) bis-dioctadecylamide dimer dilinoleic acid/ethylenediamine copolymer.

Other examples of hydrocarbon-based polyamides are polyakyleneoxy polyamide, amide terminated polyamide, and bis-stearyl ethylenediamine/neopentyl glycol/stearyl hydrogenated dimer dilinoleate copolymer.

b) Silicone Polyamide

The silicone polyamides of the invention are preferably solid at room temperature (25° C.) and atmospheric pressure (760 mmHg).

The silicone polyamides may be more particularly polymers comprising at least one unit of formula (III) or (IV):

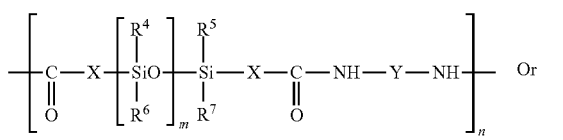

(III) Or

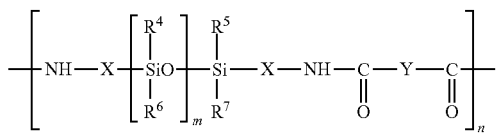

in which:
R⁴, R⁵, R⁶ and R⁷, which may be identical or different, represent a group chosen from:
  linear, branched or cyclic, saturated or unsaturated, $C_1$ to $C_{40}$ hydrocarbon-based groups, possibly containing in their chain one or more oxygen, sulfur and/or nitrogen atoms, and possibly being partially or totally substituted with fluorine atoms,
  $C_6$-$C_{10}$ aryl groups, optionally substituted with one or more $C_1$-$C_4$ alkyl groups,
  polyorganosiloxane chains possibly containing one or more oxygen, sulfur and/or nitrogen atoms,
the groups X, which may be identical or different, represent a linear or branched $C_1$ to $C_{30}$ alkylenediyl group, possibly containing in its chain one or more oxygen and/or nitrogen atoms;
Y is a saturated or unsaturated $C_1$ to $C_{50}$ linear or branched alkylene, arylene, cycloalkylene, alkylarylene or arylalkylene divalent group, which may comprise one or more oxygen, sulfur and/or nitrogen atoms, and/or may bear as substituent one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with one to three $C_1$ to $C_3$ alkyl, $C_1$ to $C_3$ hydroxyalkyl and $C_1$ to $C_6$ aminoalkyl groups, or
Y represents a group corresponding to the formula:

in which:
T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and
R⁸ represents a linear or branched $C_1$-$C_{50}$ alkyl group or a polyorganosiloxane chain, possibly comprising one or more ester, amide, urethane, thiocarbamate, urea, thiourea and/or sulfonamide groups, which may possibly be linked to another chain of the polymer;
  n is an integer ranging from 2 to 500 and preferably from 2 to 200, and m is an integer ranging from 1 to 1000, preferably from 1 to 700 and better still from 6 to 200.

The polymer may comprise identical or different units of formula (III) or (IV) of different lengths.

According to one embodiment variant of the invention, a copolymer comprising units of formula (III) or (IV) and hydrocarbon-based polyamide units may be used. In this case, the polyamide-silicone units may be located at the ends of the hydrocarbon-based polyamide.

As examples of such silicone polyamides, mention may be made of the compounds sold by the company Dow Corning under the names DC 2-8179 (DP 100) and DC 2-8178 (DP 15), the INCI name of which is Nylon-611/dimethicone copolymers.

According to a preferred embodiment, the polyamide of the present invention can be chosen from the compounds of the INCI names: polyakyleneoxy polyamide which is sold by Croda under the tradename OLEOCRAFT MP-30, amide terminated polyamide which is sold by Arizona Chemical under the tradename SYLVACLEAR A2614, bis-stearyl ethylenediamine/neopentyl glycol/stearyl hydrogenated dimer dilinoleate copolymer which is sold by Croda under the tradename OLEAOCRAFT LP-20, ethylenediamine/stearyl dimer dilinoleate copolymer sold by the Croda under the tradename Uniclear 100 VG or OLEOCRAFT LP-10-PA-(MV), and mixtures thereof.

In certain embodiments, the at least one additional oil gellant is chosen from poly C10-30 alkyl acrylates, a glutamide-based compound comprising dibutyl lauroyl glutamide, polyakyleneoxy polyamide, amide terminated polyamide, bis-stearyl ethylenediamine/neopentyl glycol/stearyl hydrogenated dimer dilinoleate copolymer, ethylenediamine/stearyl dimer dilinoleate copolymer, and mixtures thereof.

Wax

The at least one wax that can comprise the dispersion particles of the present disclosure has a melting point greater than 35° C., such as from between greater than 35° C. to about 250° C. or such as from between about 40° C. to bout 100° C. The at least one wax having a melting point greater than 35° C. is defined as having a reversible change of solid/liquid state. The melting point of a wax in solid form is the same as the freezing point of its liquid form, and depends on such factors as the purity of the substance and the surrounding pressure. The melting point is the temperature at which a solid and its liquid are in equilibrium at any fixed pressure. A solid wax begins to soften at a temperature close to the melting point of the wax. With increasing temperature, the wax continues to soften/melt until at a particular temperature, the wax completely becomes liquid at a standard atmospheric pressure. It is at this stage that an actual melting point value is given for the material under consideration. When heat is removed, the liquefied wax material begins to solidify until the material is back in solid form. By bringing the wax material to the liquid state (melting), it is possible to make it miscible with other materials such as oils, and to form a microscopically homogeneous mixture. However, when the temperature of the mixture is brought to room temperature, recrystallization of the wax with the other materials in the mixture may be obtained.

The melting points of the wax(e)s and the particles of the aqueous dispersion of the present disclosure may be determined according to known methods or apparatus such as by differential scanning calorimetry, Banc Koffler device, melting point apparatus, and slip melting point measurements.

The melting point of the wax(es) may also be defined as the temperature at which the peak endothermic heat flow occurs in a differential scanning calorimetry sweep.

The wax(es) which may comprise the particles of the present disclosure and have a melting point of greater than 35° C. is chosen from waxes that are solid or semisolid at room temperature.

The wax(es) which comprises the particles of the present disclosure may be chosen from waxes that have hardness values ranging from about 0.001 MPa (Mega Pa) to about 15 MPa, or such as from about 1 MPa to about 12 MPa, or such as from about 3 MPa to about 10 MPa.

The hardness of the wax may be determined by any known method or apparatus such as by needle penetration or using the durometer or texturometer.

Natural waxes include animal, vegetable/plant, mineral, or petroleum derived waxes. They are typically esters of fatty acids and long chain alcohols. Wax esters are derived from a variety of carboxylic acids and a variety of fatty alcohols. The waxes that may comprise the particle of the present disclosure may also be known as solid lipids.

Examples of waxes comprising the particles of the present disclosure include, but are not limited to, beeswax, hydrogentated alkyl olive esters (commercially available under the trade name phytowax olive), carnauba wax, candelilla wax, ouricoury wax, Japan wax, cork fibre wax or sugar cane wax, rice wax, montan wax, paraffin wax, lignite wax or microcrystalline wax, ceresin or ozokerite, palm kernel glycerides/hydrogenated palm glycerides and hydrogenated oils such as hydrogenated castor oil or jojoba oil, sugarcane, retamo, bayberry, rice bran, soy, castor, esparto, japan waxes, hydroxyoctacosanyl hydroxystearate, Chinese wax, cetyl palmitate, lanolin, shellac, and spermaceti; synthetic waxes such as those of the hydrocarbon type and polyethylene waxes obtained from the polymerization or copolymerization of ethylene, and Fischer-Tropsch® waxes, or else esters of fatty acids, such as octacosanyl stearate, glycerides which are solid at temperatures of above 35° C., silicone waxes, such as alkyl- or alkoxydimethicones having an alkyl or alkoxy chain ranging from 10 to 45 carbon atoms, poly(di)methylsiloxane esters which are solid at 30° C. and whose ester chain comprising at least 10 carbon atoms, or else di(1,1,1-trimethylolpropane) tetrastearate, which is sold or manufactured by Heterene under the name HEST® 2T-4S, and mixtures thereof.

Other examples of waxes or solid lipids include C20-40 di- and triglycerides, including those which contain unsaturated fatty acids, C20-40 fatty alcohols, C2-40 fatty amines and their compounds, and sterols.

The table below lists waxes whose melting points are greater than 35° C. and which are suitable for use in accordance with the present disclosure:

| INCI name and/or Trade name | Melting point (mp) |
|---|---|
| Paraffin wax | 57.3° C. |
| Stearic alcohol | 58.8° C. |
| Carnauba wax | 82.3° C. |
| Ozokerite | 66.8° C. |
| microcrystalline wax | 83.3° C. |
| polyethylene wax | 95.6° C.* |
| Hydrogenated Castor oil | 85.07° C. |
| synthetic beeswax | 51.2° C.* |
| wax AC 540 | 98.4° C.* |
| Beeswax | 62.6° C. |
| Candelilla wax | 64.3° C. |
| Hydroxyoctacosanyl Hydroxystearate | 76.8° C. |
| Hydrogenated Castor wax | 81.7° C. |
| wax AC 400 | 86.3° C. |
| PVP/Eicosene Copolymer | 37.8° C. |
| polyethylene wax | 83.9° C. |
| Hydrogenated Jojoba wax | 69.4° C. |
| palm butter | 58.4° C. |
| rice bran wax | 78.6° C.* |
| sumac wax | 48.3° C. |
| polyglycerol beeswax | 63.1° C. |
| Tricontanyl/PVP | 68.8° C.* |
| C20-40 Alkyl Stearate | 72.5° C. |
| siliconyl beeswax | 53.4° C. |
| Stearyl Stearate | 57.1° C. |
| polyethylene wax | 71.8° C. |
| polyethylene wax | 92.9° C. |
| ceresin wax | 60.1° C. |
| Ultrabee WD | 61.3° C. |
| Phytowax Olive 14 L 48 (hydrogenated myristyl olive esters) | 46.02° C. |
| Phytowax Olive 18 L 57 (hydrogenated stearyl olive esters) | 58.6° C. |
| Alcohol polyethylene wax | 95.7° C. |
| Koster wax K82P (anc.K80P) | 69.6° C. |
| Citrus Aurantium Dulcis (Orange) Peel Wax | 40.7° C. |
| Pentaerythritol Distearate | 48.5° C. |
| Theobroma Grandiflorum Seed Butter | 36.94° C. |
| DI 18/22 ADIPATE | 64.13° C. |
| DI 18/22 SEBACATE | 66.44° C. |
| DI 18/22 OCTANEDIOATE | 75.15° C. |
| Helianthus Annuus (Sunflower) Seed Wax | 75.46° C. |
| K82P-S | 67.97° C. |
| K82P-VS | 66.20° C. |
| Silicone resin wax (Dow Corning ® SW-8005) | 54.3-65.6° C. |
| Polymethylalkyl dimethylsiloxane | 67.8° C.* |
| Alcohol polyethylene wax | 76.2° C. |
| Pentaerythrityl tetrastearate | 63.0° C. |
| Tetracontanyl Stearate | 65.1° C. |
| fatty acid wax | 63.7° C. |
| Fischer-tropsch wax | 79.3° C.* |
| behenyl alcohol | 66.9° C. |
| alkyl dimethicone wax | 57.0° C. |
| Stearyl Benzoate | 40.6° C. |
| Berry wax | 47.5° C. |
| Chinese insect wax | 81.1° C.* |
| Shellac wax | 73.8° C.* |
| Behenyl fumarate | 74.5° C. |
| Koster BK-42 | 40.5° C.* |
| Koster KPC-56 | 58.5° C. |
| Koster KPC-60 | 61.7° C. |
| Koster KPC-63 | 65.2° C. |
| Koster KPC-80 | 55.6° C. |
| siliconyl candellila wax | 66.8° C. |
| Koster BK-37 | 38.0° C. |
| Ditrimethylolpropane tetrastearate | 46.5° C. |
| Synthetic Wax | 70.7° C. |
| Clariant Licowax KST 1 | 55.2° C. |
| Betawax RX-13750 | 72.0° C. |
| Dipentaerythrytol hexastearate | 67.7° C. |
| Ditrimethylolpropane tetrabehenate | 67.5° C. |
| Behenyl methacrylate grafted PDMS | 48.6° C. |
| Jojoba esters | 56.7° C. |
| Waxolive | 55.8° C. |
| Inholive | 40.3° C. |
| Phytowax Ricin 16 L 64 | 69.1° C.* |
| Phytowax Ricin 22 L 73 | 76.6° C. |
| Burco LB-02 | 45.1° C. |
| Hydrogenated Castor Oil Isostearate | 52.5° C. |
| Hydrogenated Castor Oil Isostearate | 54.0° C.* |
| Vegetable Wax | 81.0° C. |
| Hydrogenated Macadamia Seed Oil | 51.49° C. |
| Synthetic Wax | 51.4° C. |
| Dioctadecyl Carbonate | 56.7° C. |
| Montan Wax | 63.4° C. |
| Citrus Medica Limonum (Lemon) Peel Extract | 58.3° C. |

*with several melting point peaks

Particularly preferred waxes having a melting point of greater than 35° C. are beeswax, commercially available from various suppliers, hydrogenated stearyl olive ester, and commercially available from the supplier Sophim under the tradename, Phytowax Olive 18 L 57, hydrogenated myristyl olive ester, and commercially available from the supplier Sophim under the tradename, Phytowax Olive 14 L 48, VP/eicosene copolymer, commercially available from the supplier ISP under the tradenames, Antaron® V 220 or Ganex® V 220F, and ditrimethyloylpropane tetrastearate, commercially available from the supplier Heterene under the tradename, HEST 2T-4S.

Other particularly preferred waxes having a melting point of greater than 35° C. are silicone waxes, including silsesquioxane resin waxes such as C30-45 alkyldimethylsilyl propylsilsesquioxane, commercially available as DOW CORNING SW-8005 C30 Resin Wax, from the company Dow Corning and such as those described in WO2005/100444.

The wax(es) which may comprise the particles of the present disclosure have a melting point of greater than 35° C., or may range from about 40° C. to about 100° C., or such as from about 40° C. to about 80° C. The wax(es) which may comprise the particles of the present disclosure may be chosen from soft waxes and from hard waxes. Soft waxes may be defined as those waxes which have a melting point of below about 70° C., and preferably, a melting point of below about 60° C. Hard waxes may be defined as those waxes which have a melting point of equal to or greater than about 70° C., and preferably, a melting point of equal to or greater than about 60° C.

According to one embodiment, soft waxes according to the present disclosure include, but are not limited to, Paraffin wax, stearic alcohol, ozokerite, synthetic beeswax, beeswax, candelilla wax, PVP/eicosene copolymer, hydrogenated jojoba wax, palm butter, sumac wax, polyglyceryl beeswax, tricontanyl/PVP, siliconyl beeswax, stearyl stearate, ceresin wax, hydrogenated myristyl olive esters (e.g., phytowax olive 14 L 48), hydrogenated stearyl olive esters (e.g., phytowax olive 18 L 57), Koster K82P, orange peel wax, Pentaerythritol distearate, *Theobroma Grandiflorum* Seed Butter, silicone resin wax, Polymethylalkyl dim ethylsiloxane, Pentaerythrityl tetrastearate, Tetracontanyl Stearate, fatty acid wax, behenyl alcohol, alkyl dimethicone wax, Stearyl Benzoate, Berry wax, koster wax, siliconyl candelilla wax, Ditrimethylolpropane tetrastearate, Clariant Licowax KST 1, Dipentaerythrytol hexastearate, Ditrimethylolpropane tetrabehenate, Behenyl methacrylate gréffé PDMS, jojoba esters, waxolive, inholive, phytowax ricin 16 L 64, hydrogenated macadamia seed oil, synthetic wax, dooctadecyl carbonate, montan wax, lemon peel extract, ditrimethyloylpropane tetrastearate, and C30-45 alkyldimethylsilyl propylsilsesquioxane.

According to one embodiment, hard waxes according to the present disclosure, include, but are not limited to, carnauba wax, microcrystalline wax, polyethylene wax, hydrogenated castor oil, wax AC 540, Hydroxyoctacosanyl Hydroxystearate, hydrogenated castor wax, wax AC 400, rice bran wax, C20-40 alkyl stearate, Alcohol polyethylene wax, octanedioate, sunflower seed wax, fischer-tropsch wax, Chinese insect wax, shellac wax, benehyl fumarate, synthetic wax, betsawax RX-13750, phytowax ricin 22 L 73, and vegetable wax.

The wax having a melting point of greater than 35° C. and which may comprise the particles of the present disclosure may be employed in an amount ranging from about 10% to about 60% by weight, or preferably from about 15% to about 50% by weight, such as from about 20% to about 40% by weight, or such as from about 20% to about 30% by weight based on the total weight of the aqueous dispersion of the present disclosure, including all ranges and subranges therebetween.

Oil

The term "non-silicone o/V means an oil not containing any silicon atoms (Si) and the term "silicone o/V means an oil containing at least one silicon atom.

The oils of the present disclosure may be chosen from $C_6$-$C_{16}$ hydrocarbons, hydrocarbons containing more than 16 carbon atoms, particularly linear or branched hydrocarbons of mineral or synthetic origin having more than 16 carbon atoms, non-silicone oils of animal origin, plant oils of triglyceride type, synthetic triglycerides, fluoro oils, liquid fatty alcohols, liquid fatty acid and/or liquid fatty alcohol esters other than triglycerides and plant waxes, silicones oils, and mixtures thereof.

The fatty alcohols, esters and acids more particularly have at least one linear or branched, saturated or unsaturated hydrocarbon-based group comprising 6 to 30 and better still from 8 to 30 carbon atoms, which is optionally substituted, in particular with one or more hydroxyl groups (in particular 1 to 4). If they are unsaturated, these compounds may comprise one to three conjugated or unconjugated carbon-carbon double bonds.

As regards the $C_6$-$C_{16}$ hydrocarbons, they are linear, branched or optionally cyclic, and are preferably alkanes.

A hydrocarbon-based oil of animal origin that may be mentioned is perhydrosqualene.

The triglyceride oils of plant or synthetic origin are preferably chosen from liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stearineries Dubois or those sold under the names Miglyol® 810, 812 and 818 by the company Dynamit Nobel, jojoba oil and shea butter oil.

The linear or branched hydrocarbons of mineral or synthetic origin having more than 16 carbon atoms are preferably chosen from liquid paraffins, petroleum jelly, liquid petroleum jelly, polydecenes or hydrogenated polyisobutene, such as Parleam®. The fluoro oils that may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The liquid fatty alcohols which are suitable for the implementation of the invention are more particularly chosen from saturated or unsaturated, linear or branched alcohols comprising from 6 to 30 carbon atoms and preferably from 8 to 30 carbon atoms. Mention may be made, for example, of octyldodecanol, 2-butyloctanol, 2-hexyldecanol, 2-undecylpentadecanol, oleyl alcohol or linoleyl alcohol.

As regards the liquid fatty acids, mention may be made especially of saturated or unsaturated carboxylic acids comprising from 6 to 30 carbon atoms, and preferably from 9 to 30 carbon atoms, preferably chosen from oleic acid, linoleic acid, linolenic acid and isostearic acid. Theses acids are not under the form of salts, i.e. if present, the composition may not contain organic or mineral alkaline agents such as sodium hydroxide, potassium hydroxide, monoethanolamine, triethanolamine.

As regards the liquid esters of a fatty acid and/or of fatty alcohols, which are advantageously different from the triglycerides mentioned previously, mention may be made especially of liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total carbon number of the esters being greater than or equal to 6 and more advantageously greater than or equal to 10.

The esters according to this variant may also be chosen from mono-, di-, tri- and tetraesters, polyesters, and mixtures thereof.

These esters can, for example, be oleates, laurates, palmitates, myristates, behenates, cocoates, stearates, linoleates, linolenates, caprates, arachidonates or mixtures thereof, such as, in particular, oleate/palmitate, oleate/stearate or palmitate/stearate mixed esters.

Among the monoesters, mention may be made of; isocetyl stearate; isodecyl neopentanoate; isostearyl neopentanoate; 2-ethylhexyl isononanoate; ethyl and isopropyl palmitates, alkyl myristates such as isopropyl, ethyl, myristate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may be made especially of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as liquid fatty ester, sugar esters and diesters of $C6$-$C_{30}$ and preferably $C_{12}$-$C_{22}$ fatty acids. It is recalled that the term "sugar" means oxygen-bearing hydrocarbon-based compounds which have several alcohol functions, with or without aldehyde or ketone functions, and which comprise at least 4 carbon atoms. These sugars can be monosaccharides, oligosaccharides or polysaccharides.

The sugar esters of fatty acids may be chosen in particular from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

An example that may be mentioned is the product sold under the name Glucate® DO by the company Amerchol, which is a methylglucose dioleate.

The silicones oils that may be used in the powder composition of the present invention are volatile or non-volatile, cyclic, linear or branched silicones, which are unmodified or modified with organic groups, having a viscosity from $5\times10^{-6}$ to 2.5 $m^2/s$ at 25° C., and preferably $1\times10^{-5}$ to 1 $m^2/s$.

Preferably, the silicone is chosen from liquid polydialkylsiloxanes, especially polydimethylsiloxanes (PDMS), and liquid organomodified polysiloxanes comprising at least one functional group chosen from amino groups and alkoxy groups.

Organopolysiloxanes are defined in greater detail in Walter Noll's Chemistry and Technology of Silicones (1968), Academic Press. They may be volatile or nonvolatile.

When they are volatile, the silicones are more particularly chosen from those having a boiling point of between 60° C. and 260° C., and more particularly still from: (i) cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide.

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5\times10^{-6}$ $m2/s$ at 25° C. An example is decamethyltetrasiloxane sold in particular under the name SH 200 by the company Toray Silicone.

Use may be made of non-volatile polydialkylsiloxanes, among which mention may be made mainly of polydimethylsiloxanes having trimethylsilyl end groups. The viscosity of the silicones is measured at 25° C. according to ASTM standard 445 Appendix C.

Mention may be made, among these polydialkylsiloxanes, without implied limitation, of the following commercial products:

the Silbione® oils of the 47 and 70 047 series or the Mirasil® oils sold by Rhodia, such as, for example, the oil 70 047 V 500 000;

the oils of the Mirasil® series sold by Rhodia;

the oils of the 200 series from the company Dow Corning, such as DC200 with a viscosity of 60 000 mm2/s;

the Viscasil® oils from General Electric and certain oils of the SF series (SF 96, SF 18) from General Electric.

Mention may also be made of polydimethylsiloxanes bearing dimethylsilanol end groups known under the name dimethiconol (CTFA), such as the oils of series 48 from the company Rhodia.

The liquid fatty substances are advantageously chosen from liquid petroleum jelly, $C_6$-$C_{16}$ alkanes, polydecenes, non-silicone oils of plant, mineral or synthetic origin, liquid fatty alcohols, liquid fatty acids and liquid esters of a fatty acid and/or of a fatty alcohol, or mixtures thereof.

A preferred liquid fatty substance for use in the present invention is mineral oil (paraffin) which may be commercially available from the supplier Sonneborn under the tradename Kaydol® Heavy White Mineral Oil or from the supplier Exxonmobil Chemical under the tradename Primol™ 352 or from Sonneborn under the tradename Blandol, or from Armedsa under the tradename Aemoil M-302CG or from Exxonmobil Chemical under the tradename Marcol 82.

In certain embodiments, suitable oils that may comprise the particles of the invention are non-volatile oils, including, but not limited to, plant oils and natural oils (sweet almond oil, macadamia oil, grapeseed oil, olive oil, argan oil, tocopherol or vitamin E, shea butter oil, tocopherol or vitamine E oil); synthetic oils, for instance perhydrosqualene; fatty acids or fatty esters (for instance the $C_{12}$-$C_{15}$ alkyl benzoate sold under the trade name Finsolv® TN, commercially available from Innospec or Tegosoft® TN, commercially available from Evonik Goldschmidt, octyl palmitate, isopropyl lanolate; esters such as tocopheryl acetate; and triglycerides, including capric/caprylic acid triglycerides); oxyethylenated or oxypropylenated fatty esters and ethers; or fluoro oils, and polyalkylenes.

Other suitable oils include for example: silicone oils, or non-volatile polymethylsiloxanes (PDMS) with a linear or cyclic silicone chain, which are liquid or pasty at room temperature, especially cyclopolydimethylsiloxanes (cyclomethicones) such as cyclohexasiloxane; polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenyl-siloxanes, diphenyl dimethicones, diphenylmethyl-diphenyltrisiloxanes or 2-phenylethyl trimethylsiloxy silicates, and polymethylphenylsiloxanes; mixtures thereof. Other silicone oils include non-volatile silicones, for example, dimethicone fluids having viscosity values of equal to or greater than 300 cst, and pentaphenyldimethicone, also known as trimethyl pentaphenyl trisiloxane, commercially available from Dow Corning under the tradename Dow Corning® 555.

Other suitable oils include, but are not limited to, non-volatile hydrocarbon-based oils and esters such as those described above.

The oil suitable for use in the present invention may also be a mixture of any one of the above-described oils, particularly those oils that can impart a fragrance or perfume or pleasant-smelling odors. Such a mixture may be referred to as a fragrance oil or perfume oil or aroma oil.

The fragrance oils of the present invention may contain essential oils, components of aromas, such as for example, essential oils of sage, chamomile, clove, Melissa balm, mint, cinnamon tree leaves, lime blossom, juniper, vetiver, oilbanum, galbanum, labdanum, bergamot, citronellol, lemon, mandarin, orange, and lavandin.

In certain embodiments, the oil comprising the particles of the present disclosure is chosen from $C_6$-$C_{16}$ alkanes, non-silicone oils of plant, mineral or synthetic origin, liquid fatty alcohols, liquid fatty acids, liquid esters of a fatty acid, liquid esters of a fatty alcohol, silicone oils, fragrance oils, and mixtures thereof.

In other embodiments, the oil comprising the particles of the present disclosure is a fragrance oil or a mixture of fragrance oils.

In yet other embodiments, the oil(s) that may comprise the particle of the present disclosure is selected such that the melting point of the particles of the present disclosure is greater than 35° C.

The oil which may comprise the particles of the present disclosure may be employed in an amount ranging from about 85% to about 99.9% by weight, such as from about 85% to about 99% by weight, or such as from about 90% to about 98% by weight, based on the total weight of the oil gellant comprising at least one styrenic block copolymer and the at least one oil of the present disclosure, including all ranges and subranges therebetween.

Styrenic Block Copolymer/Wax/Oil Combinations

The particles of the present invention are comprised of an oil gellant comprising at least one styrenic block copolymer and a fatty substance selected from at least one wax having a melting point of greater than 35° C., at least one oil, and mixtures thereof.

In an embodiment of the present invention, the particles are comprised of an oil gellant comprising at least one styrenic block copolymer and a fatty substance selected from at least one wax having a melting point of greater than 35° C.

Preferably, the weight ratio of the at least one wax having a melting point of greater than 35° C. to the at least one styrenic block copolymer ranges from about 100:1 to about 1:100, such as from about 20:1 to about 1:20, or such as from about 10:1 to about 1:10.

In an embodiment, the oil gellant comprising at least one styrenic block copolymer is present in an amount of from about 5% to about 15% by weight and the at least one wax is present in an amount of from about 85% to about 95% by weight, all weights based on the total weight of the oil gellant and the wax.

In particularly preferred embodiments, the weight ratio of the at least one wax having a melting point of greater than 35° C. to the at least one styrenic block copolymer is about 11.5:1.

In another embodiment, the particles are comprised of an oil gellant comprising at least one styrenic block copolymer and a fatty substance selected from at least one oil.

In one embodiment, the weight ratio of the at least one oil to the at least one styrenic block copolymer ranges from about 100:1 to about 1:100, such as from about 20:1 to about 1:20, or such as from about 10:1 to about 1:10.

In another embodiment, the weight ratio of the at least one oil to the at least one styrenic block copolymer ranges from about 5:1 to about 1000:1 wherein the at least one oil is present in an amount of from about 85% to about 99.9% by weight, based on the total weight of the styrenic block copolymer and the at least one oil.

In yet another embodiment of the present invention, the particles are comprised of an oil gellant comprising at least one styrenic block copolymer and a fatty substance comprising at least one wax having a melting point of greater than 35° C. and at least one oil.

In certain embodiments, the at least one wax having a melting point of greater than 35° C., the at least one oil, and the at least one styrenic block copolymer are each present in an amount of from about 0.1% to about 99.8% by weight, including all ranges and subranges therebetween all weights being based on the total weight of the styrenic block copolymer, the wax and the oil.

In a particular embodiment, the amount of the at least one wax having a melting point of greater than 35° C. is equal to or greater ban the total amount of the at least one oil and the amount of the at least one styrenic block copolymer.

In one embodiment, when the at least one oil comprises a non-volatile oil, the weight ratio of the at least one wax having a melting point of greater than 35° C., to the at least one oil, and to the at least one styrenic block copolymer is 11.5:1:0.5.

In another embodiment, when the at least one oil comprises fragrance oils, the weight ratio of the at least one wax having a melting point of greater than 35° C., to the at least one oil, and to the at least one styrenic block copolymer is 11.5:1:1.5.

Particles

The particles of the aqueous dispersion have a volume-basis particle size distribution with peaks in the range of equal to or greater than 1 μm up to about 100 μm.

In certain preferred embodiments, the particles have a volume-basis particle size distribution with peaks in the range of about 30 μm up to about 70 μm, or such as about 40 μm up to about 65 μm, or such as about 45 μm up to about 65 μm, or such as equal to or greater than 1 μm up to about 20 μm.

In preferred embodiments, the particles comprising the aqueous dispersion have a volume-basis particle size distribution with peaks in the range of from between about 20 μm up to about 70 μm.

In particularly preferred embodiments, the particles comprising the aqueous dispersion have a volume-basis particle size distribution with peaks in the range of from between about 45 μm up to about 65 μm, preferably, from between about 45 μm up to about 55 μm. In some embodiments, the particles comprising the aqueous dispersion have a volume-basis particle size distribution with a peak at about 50 μm.

In other embodiments, the particles comprising the aqueous dispersion have a volume-basis particle size distribution with peaks in the range of equal to or greater than 1 μm up to about 20 μm.

The term "volume-basis particle size distribution" as used herein refers to the particle size distribution of a dispersion where population percentages are determined based on the volume of particles at the indicated diameter. Such distributions are measured by laser diffraction or similar methods.

The term "peak" as used herein with respect to the volume-basis particle size distribution refers to the particle diameter at which the greatest volume of particles exists.

Thus, the volume-basis particle size distribution in the aqueous dispersion of the present disclosure may range from equal to or greater than 1 μm up to about 500 μm, or from equal to or greater than 1 μm up to about 250 μm, or from equal to or greater than 1 μm up to about 150 μm, with the peaks of the volume-basis particle size distribution ranging from equal to or greater than 1 μm up to about 100 μm.

The particles of the present disclosure are preferably in solid form or semi-solid form.

The particles in the aqueous dispersion of the present disclosure can be substantially homogeneous with respect to their shape. The term "substantially" as used in this context means that 50% or more of the particles in an aqueous dispersion of the present disclosure are of the same spherical, ellipsoidal or oval shape and of the same particle size. The term "substantially" as used in the context of the shape of a spherical particle may also mean that the particle is of substantially isotropic shape, i.e., it has a relatively regular morphology.

Thus, the ratio of the lengths of the longest to the shortest perpendicular axes of the particle cross section can be at about 1:1 or at about 1.5:1 or at about 2:1 or at about 3:1. Moreover, a line of symmetry is not required when the particle has a spherical shape. Further, the particle may have surface texturing, such as lines or indentations or protuberances that are small in scale when compared to the overall size of the particle and still be substantially spherical or ellipsoidal or oval.

The particle size, particle size distribution, and shape of the particles of the present disclosure may be evaluated by any known method such as those described in US patent application number 2006/0292095, for example, laser diffraction, ultrasonic extinction (acoustic spectroscopy), photo cross-correlation spectroscopy, granulometry, and image analysis (optical microscopy).

The particles of the present disclosure have a melting point greater than 35° C., such as from between greater than 35° C. to about 250° C., or such as from between greater than 35° C. to about 130° C., or such as from between greater than 35° C. to about 120° C., or such as from between about 40° C. to about 100° C., orsuch as from between about 40° C. to about 65° C.

The particles of the present disclosure may have different properties with respect to hardness and/or melting point and/or shape and/or size.

Additional Ingredients

The particles can further comprise additional ingredients such as the above-described oil gellants other than an oil gellant comprising at least one styrenic block copolymer, colorants, sunscreen agents, volatile solvents, waxes having melting points of 35° C. or less, emulsifying polymers, silicas, talc, clays, ceramides, and mixtures thereof. These additional ingredients can be added during the time of making the aqueous dispersion in order to either improve/modify the physical properties of the particles and/or to allow the particles to provide other benefits in addition to the benefits obtained from waxes.

The particles of the aqueous dispersion of the present invention may additionally comprise at least one colorant. The at least one colorant is preferably chosen from pigments and dyes.

"Colorant" as used herein means any ingredient that provides color to a substrate or changes/alters the color of said substrate by either depositing color onto or lightening/highlighting the color of said substrate.

In a preferred embodiment, the at least one colorant may be a pigment or a dye.

"Pigment" as used herein can refer to any type particle colorant (any color including white or black) that is insoluble in water. Pigments can be organic, inorganic, or a combination of both in nature. A mixture of pigments in the pigment composition can produce various shades of color.

Representative pigments include white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium.

Among the organic pigments, mention may be made of carbon black and lacquers such as calcium, barium, aluminum, zirconium or strontium salts.

The dye of the present invention includes, but is not limited to water-soluble or liposoluble dyes.

Among the water-soluble dyes, mention may be made of dyes that are common in the cosmetic field such as the disodium salt of ponceau, the disodium salt of alizarine green, quinoline yellow, the trisodium salt of amaranth, the disodium salt of tartrazine, the monosodium salt of rhodamine, the disodium salt of fuchsin, and xanthophyll, and mixtures thereof.

Representative dyes also include, but are not limited to, direct dyes such as halo acid dyes, azo direct dyes, methine direct dyes, carbonyl direct dyes, azine direct dyes, nitro (hetero) aryl direct dyes, especially nitrobenzene dyes, and tri (hetero) arylmethane direct dyes, tri(hetero)arylmethane dyes, porphyrin dyes, phthalocyanin direct dyes, anthraquinone dyes and the addition salts thereof; alone or as mixtures. Exemplary direct dyes that may be used include those that are nonionic, anionic, cationic, and amphoteric.

In various embodiments, the azo dyes comprise an —N═N— function in which the two nitrogen atoms are not simultaneously engaged in a ring. However, it is not excluded for one of the two nitrogen atoms of the sequence —N=N— to be engaged in a ring.

The dyes of the methine family are, for example, compounds comprising at least one sequence chosen from >C=C< and —N=C< in which the two atoms are not simultaneously engaged in a ring. However, it is pointed out that one of the nitrogen or carbon atoms of the sequences may be engaged in a ring. More particularly, the dyes of this family are derived from compounds of true methine type (comprising one or more abovementioned sequences —C=C—); of azomethine type (comprising at least one, or more, sequences —C=N—) with, for example, azacarbocyanins and their isomers, diazacarbocyanins and their isomers, and tetraazacarbocyanins; of mono- and diarylmethane type; of indoamine (or diphenylamine) type; of indophenol type; or of indoaniline type.

As regards the dyes of the carbonyl family, examples that may be mentioned include dyes chosen from acridone, benzoquinone, anthraquinone, naphthoquinone, benzanthrone, anthranthrone, pyranthrone, pyrazol-anthrone, pyrimidinoanthrone, flavanthrone, idanthrone, flavone, (iso) violanthrone, isoindolinone, benzimid-azolone, isoquinolinone, anthrapyridone, pyrazolo-quinazolone, perinone, quinacridone, quinophthalone, indigoid, thioindigo, naphthalimide, anthrapyrimidine, diketopyrrolopyrrole and coumarin dyes.

As regards the dyes of the azine family, mention may be made, for example, of azine, xanthene, thioxanthene, fluorindine, acridine, (di)oxazine, (di)thiazine and pyronin dyes.

The nitro (hetero) aromatic dyes are more particularly nitrobenzene or nitropyridine direct dyes.

As regards the dyes of porphyrin or phthalocyanin type, it is possible to use cationic or non-cationic compounds, optionally comprising one or more metals or metal ions, for instance alkali metals, alkaline-earth metals, zinc and silicon. Examples of particularly suitable synthetic direct dyes that may be mentioned include nitrobenzene dyes; azo direct dyes; methine direct dyes; azomethine direct dyes, with, more particularly, diazacarbocyanins and isomers thereof and tetraazacarbocyanins (tetraazapentamethines); quinone direct dyes, and in particular anthraquinone, naphthoquinone or benzoquinone dyes; azine direct dyes; xanthene direct dyes; triarylmethane direct dyes; indoamine direct dyes; indigoid direct dyes; phthalocyanin and porphyrin direct dyes; alone or as mixtures.

In various embodiments, direct dyes include, but are not limited to, cationic direct dyes, such as cationic mixed dyes including at least one chromophore, such as at least two chromophores. As used herein, "cationic mixed dye" means a dye whose cationic charge can form an integral part of the chromophore and/or of the linker, or alternatively a dye whose cationic charge is present via a substituent on the chromophore and/or on the linker. As used herein, "chromophore" means a radical derived from a dye, i.e. a radical of a molecule that has at least one absorption maximum in the visible region between 400 and 800 nm, this absorbance requiring no prior oxidation or any combination with other chemical species.

The at least one chromophore may be chosen from acridine, acridone, anthranthrone, anthrapyrimidine, anthraquinone, azine, azo, azomethine, benzanthrone, benzimidazole, benzimidazolone, benzindole, benzoxazole, benzopyran, benzothiazole, benzoquinone, bis-azine, bis-isoindoline, carboxanilide, coumarin, cyanins, diazine, diketopyrrolopyrrole, dioxazine, diphenylamine, diphenylmethane and dithiazine chromophores, flavonoids, fluorindines, formazans, hydrazones, hydroxy ketones, indamines, indanthrones, indigoids, pseudo-indigoids, indophenols, indoanilines, isoindolines, isoindolines, isoindolinones, isoviolanthrones, lactones, methines, naphthalimides, naphthanilides, naphtholactams, naphthoquinones, nitro dyes, oxadiazoles, oxazines, perilones, perinones, perylenes, phenazines, phenothiazines, phthalocyanin, polyenes/carotenoids, porphyrins, pyranthrones, pyrazolanthrones, pyrazolones, pyrimidinoanthrones, pyronines, quinacridones, quinolines, quinophthalones, squaranes, stilbenes, tetrazoliums, thiazines, thioindigo, thiopyronines, triarylmethanes, and xanthenes.

Other suitable dyes of the present invention include natural dyes. Suitable examples of natural dyes include, but are not limited to, mention may be made of quinone dyes (lawsone, juglone, etc.), alizarin, purpurin, carminic acid, kermesic acid, purpurogallin, proto-catechaldehyde, indigo, curcumin, spinulosin, various types of chlorophyll and chlorophyllin, orceins, hematein, hematoxylin, brazilin, brazilein, safflower dyes (such as carthamin), flavonoids (morin, apigenidin, sandalwood), anthocyans (such as apigeninidin), carotenoids, tannins, preferably lawsone, juglone, alizarin, purpurin, carminic acid, kermesic acid, purpurogallin, protocatechaldehyde, indigo, isatin, curcumin, spinulosin, apigenidin, chlorophyllin, sorghum, orceins and cochineal carmine. It is also possible to use extracts or decoctions containing these natural dyes and in particular henna-based extracts.

In a particular embodiment, the at least one colorant (c) comprises dyes chosen from direct dyes and natural dyes.

In a preferred embodiment, the colorant comprises at least one compound generally used for the temporary coloration of head hair or of nails or of skin.

In other preferred embodiments, the colorant may comprise at least one compound capable of temporarily coloring the skin, such as self-tanning agents (especially dihydroxyacetone, DHA).

Representative sunscreen agents which can additionally comprise particles of the aqueous dispersions of the present invention may be chosen from the organic and inorganic sunscreens or UV filters.

Non-limiting examples of the at least one sunscreen agent include anthranilates; salicylic derivatives; camphor derivatives; benzophenone and its derivatives; b,b diphenylacrylate and its derivatives; triazine derivatives; benzylidenecamphor and its derivatives; benzotriazole and its derivatives; benzalmalonate and its derivatives; benzimidazole and its derivatives; imidazolines; bis-benzazolyl derivatives; p aminobenzoic acid (PABA) derivatives; methylenebis(hydroxyphenylbenzotriazole) and its derivatives; benzoxazole derivatives; screening polymers and screening silicones such as those described especially in patent application WO 93/04665; dimers derived from a alkyl-styrene; 4,4-diarylbutadienes such, and mixtures thereof.

Examples of mineral photoprotective agents are chosen from pigments and even more preferably nanopigments (mean size of the primary particles: generally between 5 nm and 100 nm and preferably between 10 nm and 50 nm) of treated or untreated metal oxides such as, for example, nanopigments of titanium oxide (amorphous or crystallized in rutile and/or anatase form), of iron oxide, of zinc oxide, of zirconium oxide or of cerium oxide. The treated nanopigments may more particularly be treated titanium oxides.

The treated nanopigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminium salts of fatty acids, metal (titanium or aluminium) alkoxides, poly-ethylene, silicones, proteins (collagen or elastin), alkanolamines, silicon oxides, metal oxides, sodium hexametaphosphate, alumina or glycerol.

Mention may also be made of mixtures of metal oxides, especially of titanium dioxide and of cerium dioxide, including the silica-coated equal-weight mixture of titanium dioxide and of cerium dioxide, and also the alumina, silica and silicone-coated mixture of titanium dioxide and of zinc dioxide, or the alumina, silica and glycerol-coated mixture of titanium dioxide and of zinc dioxide.

Particularly preferred sunscreen agents of the present invention are chosen from octocrylene, terephthalylidene dicamphor derivatives, benzylidenecamphor derivatives and benzotriazole derivatives, in particular, drometrizole trisiloxane, also known under the tradename of Mexoryl XL.

The particles of the aqueous dispersions of the present disclosure can also further comprise volatile solvents. Representative examples of suitable volatile organic solvents include, but are not limited to, volatile hydrocarbon-based oils and volatile silicone oils. The volatile solvents of the present invention are those other than fragrance oils.

Suitable volatile hydrocarbon oils include, but are not limited to, those having from 8 to 16 carbon atoms and their mixtures and in particular branched C8 to C016 alkanes such as C8 to C16 isoalkanes (also known as isoparaff ins), isododecane, isodecane, isohexadecane, and for example, the oils sold under the trade names of Isopar or Permethyl, the C8 to C16 branched esters such as isohexyl or isodecyl neopentanoate and their mixtures. Preferably, the volatile hydrocarbon oils have a flash point of at least 40° C. It is also possible to use mixtures of isoparaff ins and other volatile hydrocarbon-based oils, such as petroleum distillates, Suitable volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Examples of volatile silicone oils that may be used include, but are not limited to, octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane, and their mixtures. Preferably, the volatile silicone oils have a flash point of at least 40° C.

Other suitable volatile solvents may be chosen from polar volatile solvents, including but not limited to, alcohols, volatile esters and volatile ethers. In general, they have a flash point below about 25° C.

Although not wishing to be bound by any particular theory, it is believed that the presence of the volatile solvent in the aqueous dispersion of the present disclosure helps to soften the components of the particles and make them more pliable, thereby making it easier to apply on a substrate.

Suitable additional waxes that may further comprise the particle are those waxes whose melting points are at 35° C. or less; these waxes include, but are not limited to, Hest 2T-5E-4S, Ditrimethylolpropane tetralaurate, Koster BK-34, Fluoro Polymethylalkyl dimethylsiloxane, Blend of Dilauryl Adipate and Ditetradecyl Adipate, Astrocaryum MuruMuru Seed Butter, Myrica Pubescens Wax, PEG-70 Mango Glycerides, oxypropylenated lanolin wax, hydrogenated Coco-glycerides.

Nevertheless, the waxes whose melting points are at 35° C. or less are selected such that the resulting melting point of the particle of the present disclosure is greater than 35° C.

The particles of the aqueous dispersion of the present disclosure may comprise an emulsifying polymer, i.e. an amphiphilic polymer.

Among the emulsifying polymers that are suitable for use in the invention, mention may be made of: POE-POP diblock and triblock copolymers such as those described in patent U.S. Pat. No. 6,464,990; polyoxyethylenated silicone surfactants such as those described in patent U.S. Pat. No. 6,120,778; non-crosslinked hydrophobic AMPSs such as those described in EP 1 466 588; amphiphilic acrylic polymers, such as PEMULEN TR-1 or TR-2.

Silicas, Talc, and Clays

The particles of the aqueous dispersions of the invention may further comprise sub-micron-sized to micron-sized particles of silica, talc, and/or clays, which include, but are not limited to, montmorillonite, bentonite, hectorite, attapulgite, sepiolite, laponite, smectite, kaolin, and their mixtures.

These clays can be modified with a chemical compound chosen from quaternary ammoniums, tertiary amines, amine acetates, imidazo lines, amine soaps, fatty sulphates, alkylarylsulphonates, amine oxides and their mixtures.

Mention may be made, as organophilic clays, of quaternium-18 bentonites; stearalkonium bentonites; or quaternium-18/benzalkonium bentonites.

Suitable silicas may include pyrogenic silicas obtained by high temperature hydrolysis of a volatile silicon compound in an oxyhydrogen flame, producing a finely divided silica. This process makes it possible in particular to obtain hydrophilic silicas which exhibit a large number of silanol groups at their surfaces.

It is possible to substitute silanol groups by hydrophobic groups: a hydrophobic silica is then obtained. The hydrophobic groups can be: trimethylsiloxyl groups, obtained in particular by treatment of pyrogenic silica in the presence of hexamethyldisilazane ("Silica silylate") or dimethylsilyloxyl or polydimethylsiloxane groups, obtained in particular by treatment of pyrogenic silica in the presence of polydimethylsiloxane or of dimethyldichlorosilane ("Silica dimethyl silylate").

Ceramide compounds that may be useful according to various embodiments of the disclosure include ceramides, glycoceramides, pseudoceramides, and mixtures thereof. The ceramides which may be chosen include, but are not limited to, those described by DOWNING in Arch. Dermatol, Vol. 123, 1381-1384 (1987), DOWNING in Journal of Lipid Research, Vol. 35, page 2060 (1994), or those described in French patent FR 2673179.

Further exemplary ceramides that may be used according to various embodiments of the disclosure include, but are not limited to, compounds of the general formula (I):

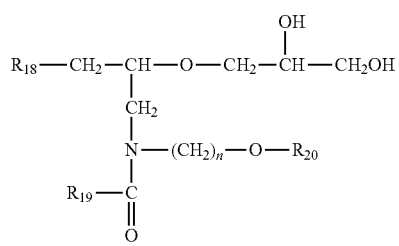

wherein, in formula (I):
  $R_{18}$ and $R_{19}$ are, independently, chosen from alkyl- or alkenyl groups with 10 to 22 carbon atoms, $R_{20}$ is chosen from methyl, ethyl, n-propyl or isopropyl groups, and n is a number ranging from 1 to 6, such as, for example, 2 or 3.

In further embodiments, ceramide compounds may be chosen from compounds of formula (II), as described in US20050191251 and US20090282623:

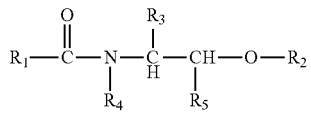

wherein, in formula (II):

$R_1$ is chosen from either a saturated or unsaturated, linear or branched $C_1$-$C_{50}$, e.g. $C_5$-$C_{50}$, hydrocarbon radical, it being possible for this radical to be substituted with one or more hydroxyl groups optionally esterified with an acid $R_7COOH$, $R_7$ being an optionally mono- or polyhydroxylated, linear or branched, saturated or unsaturated $C_1$-$C_{35}$ hydrocarbon radical, it being possible for the hydroxyl(s) of the radical $R_7$ to be esterified with an optionally mono- or polyhydroxylated, linear or branched, saturated or unsaturated $C_1$-$C_{35}$ fatty acid, or a radical R"—(NR—CO)—R', R being chosen from a hydrogen atom or a mono- or polyhydroxylated, $R_2$ being chosen from a hydrogen atom, a saccharide-type radical;

$R_3$ chosen from a hydrogen atom or a hydroxylated or nonhydroxylated, saturated or unsaturated, $C_1$-$C_{33}$ hydrocarbon radical;

$R_4$ being chosen from a hydrogen atom, a methyl or ethyl radical, an optionally hydroxylated, linear or branched, saturated or unsaturated $C_3$-$C_{50}$ hydrocarbon radical or a radical —$CH_2$—CHOH—$CH_2$—O—$R_6$ in which $R_6$ denotes a $C_{10}$-$C_{26}$ hydrocarbon radical or a radical $R_8$—O—CO—$(CH_2)p$, $R_8$ chosen from a $C_1$-$C_{20}$ hydrocarbon radical, p being an integer varying from 1 to 12; and $R_5$ denotes a hydrogen atom or an optionally mono- or polyhydroxylated, linear or branched, saturated or unsaturated $C_1$-$C_{30}$ hydrocarbon radical, with the proviso that when $R_3$ and $R_5$ denote hydrogen or when $R_3$ denotes hydrogen and $R_5$ denotes methyl, then $R_4$ does not denote a hydrogen atom, or a methyl or ethyl radical.

In yet further embodiments, ceramide compounds useful according to the disclosure may be chosen from compounds of the general formula (III):

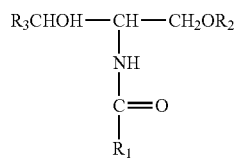

wherein, in formula (III):

$R_1$ is chosen from a linear or branched, saturated or unsaturated alkyl group, derived from $C_{14}$-$C_{30}$ fatty acids;

$R_2$ is chosen from a hydrogen atom or a (glycosyl)$_n$, (galactosyl)$_m$, or sulphogalactosyl group, in which n is an integer ranging from 1 to 4 and m is an integer ranging from 1 to 8; and $R_3$ is chosen from a $C_5$-$C_{26}$ hydrocarbon-based group, saturated or unsaturated in the alpha-position, it being possible for this group to be substituted with one or more $C_1$-$C_{14}$ alkyl groups.

Exemplary ceramides of formula (III) are N-linoleoyldihydrosphingosine, N-oleoyldihydrosphingosine, N-palmitoyldihydro-sphingosine, N-stearoyldihydrosphingosine, N-behenoyldihydrosphingosine, or mixtures thereof.

In further embodiments, ceramide compounds useful according to the disclosure may be chosen from compounds of the general formula (IV):

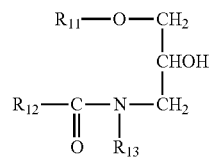

wherein, in formula (IV):

$R_{11}$ and $R_{12}$ are, independently, chosen from alkyl or alkenyl groups with 10 to 22 carbon atoms, $R_{13}$ is an alkyl or hydroxyl alkyl group with 1 to 4 carbon atoms, and n is a number ranging from 1 to 6, such as, for example, 2 or 3.

In at least one embodiment, the at least one ceramide compound is chosen from cetyl-PG-hydroxyethylpalmitamide. In a further embodiment, the at least one ceramide compound is chosen from propanediamide, N,N-dihexadecyl-N,N-bis-(2-hydroxyethyl), such as that sold commercially as Questamide H or Pseudoceramide H by the company Quest International Australia Pty. Ltd. In yet a further embodiment, the at least one ceramide compound is chosen from Cetyl-PG Hydroxylpalmatide/decyl glucoside/water, sold as SOFCARE P100H by Kao.

Surfactant Mixture

The surfactant mixture of the present disclosure comprises at least one nonionic surfactant and at least one ionic surfactant.

In general, nonionic surfactants having a Hydrophilic-Lipophilic Balance (HLB) of from at least 5, such as from about 5 to about 20, or such as from about 5 to about 15, are contemplated for use by the present invention. Nonlimiting examples of nonionic surfactants useful in the compositions of the present invention are disclosed in McCutcheon's "Detergents and Emulsifiers," North American Edition (1986), published by Allured Publishing Corporation; and McCutcheon's "Functional Materials," North American Edition (1992); both of which are incorporated by reference herein in their entirety.

Examples of nonionic surfactants useful herein include, but are not limited to, alkoxylated derivatives of the following: fatty alcohols, alkyl phenols, fatty acids, fatty acid esters and fatty acid amides, wherein the alkyl chain is in the $C_{12}$-$C_{50}$ range, preferably in the $C_{16}$-$C_{40}$ range, more preferably in the $C_{24}$ to $C_{40}$ range, and having from about 1 to about 110 alkoxy groups. The alkoxy groups are selected from the group consisting of $C_2$-$C_6$ oxides and their mixtures, with ethylene oxide, propylene oxide, and their mixtures being the preferred alkoxides. The alkyl chain may be linear, branched, saturated, or unsaturated. Of these alkoxylated non-ionic surfactants, the alkoxylated alcohols are preferred, and the ethoxylated alcohols and propoxylated alcohols are more preferred. The alkoxylated alcohols may be used alone or in mixtures thereof. The alkoxylated alcohols may also be used in mixtures with those alkoxylated materials disclosed herein-above.

Other representative examples of such ethoxylated fatty alcohols include laureth-3(a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) steareth-10 (a stearyl alcohol ethoxylate having an average degree of ethoxylation of 10), and steareth-2 (a stearyl alcohol ethoxylate having an average degree of ethoxylation of 2), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), and other derivatives and mixtures of the preceding.

Also available commercially are Brij® nonionic surfactants from Uniqema, Wilmington, Del. Typically, Brij® is the condensation products of aliphatic alcohols with from about 1 to about 54 moles of ethylene oxide, the alkyl chain of the alcohol being typically a linear chain and having from about 8 to about 22 carbon atoms, for example, Brij® 72 (i.e., Steareth-2) and Brij® 76 (i.e., Steareth-10).

Also useful herein as nonionic surfactants are alkyl glycosides, which are the condensation products of long chain alcohols, e.g. $C_8$-$C_{30}$ alcohols, with sugar or starch polymers. These compounds can be represented by the formula (S)n—O—R wherein S is a sugar moiety such as glucose, fructose, mannose, galactose, and the like; n is an integer of from about 1 to about 1000, and R is a $C_8$-$C_{30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a $C_8$-$C_{20}$ alkyl group, and n is an integer of from about 1 to about 9. Commercially available examples of these surfactants include decyl polyglucoside (available as APG® 325 CS) and lauryl polyglucoside (available as APG® 600CS and 625 CS), all the above-identified polyglucosides APG® are available from Cognis, Ambler, Pa. Also useful herein are sucrose ester surfactants such as sucrose cocoate and sucrose laurate.

Other nonionic surfactants suitable for use in the present invention are glyceryl esters and polyglyceryl esters and their derivatives, including but not limited to, glyceryl monoesters, preferably glyceryl monoesters of $C_{16}$-$C_{22}$ saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of $C_{16}$-$C_{22}$ saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof. glyceryl ester derivatives include, but are not limited to, polyethylene glycol ethers of glyceryl esters such as PEG-30 glyceryl stearate, PEG-30 glyceryl diisostearate, PEG-30 glyceryl isostearate, PEG-30 glyceryl laurate, PEG-30 glyceryl oleate, and mixtures thereof.

Also useful herein as nonionic surfactants are sorbitan esters. Preferable are sorbitan esters of $C_{16}$-$C_{22}$ saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from Uniqema, Wilmington, Del.), sorbitan monoisostearate (e.g., GRILL® 6 from Croda, Inc., Edison, N.J.), sorbitan stearates (e.g., SPAN® 60), sorbitan trioleate (e.g., SPAN® 85), sorbitan tristearate (e.g., SPAN®65), sorbitan palmitate (e.g., SPAN® 40), and sorbitan isostearate. Sorbitan palimtate and sorbitan sesquioleate are particularly preferred for use in the present disclosure.

Also suitable for use herein are alkoxylated derivatives of glyceryl esters, sorbitan esters, and alkyl polyglycosides, wherein the alkoxy groups is selected from the group consisting of $C_2$-$C_6$ oxides and their mixtures, with ethoxylated or propoxylated derivatives of these materials being the preferred. Nonlimiting examples of commercially available ethoxylated materials include TWEEN® (ethoxylated sorbitan mono-, di- and/or tri-esters of $C_{12}$ to $C_{18}$ fatty acids with an average degree of ethoxylation of from about 2 to about 20).

Preferred nonionic surfactants are those formed from a fatty alcohol, a fatty acid, or a glyceride with a $C_4$ to $C_{36}$ carbon chain, preferably a $C_{12}$ to $C_{18}$ carbon chain, more preferably a $C_{16}$ to $C_{18}$ carbon chain, derivatized to yield an HLB of at least 8. HLB is understood to mean the balance between the size and strength of the hydrophilic group and the size and strength of the lipophilic group of the surfactant. Such derivatives can be polymers such as ethoxylates, propoxylates, polyglucosides, polyglycerins, polylactates, polyglycolates, polysorbates, and others that would be apparent to one of ordinary skill in the art. Such derivatives may also be mixed polymers of the above, such as ethoxylate/propoxylate species, where the total HLB is preferably greater than or equal to 8. Preferably the nonionic surfactants contain ethoxylate in a molar content of from 10-25, more preferably from 10-20 moles.

Particularly preferred nonionic surfactants of the present disclosure are chosen from polyethylene glycol ethers of glyceryl esters, PEG-30 glyceryl stearate and sorbitan esters such as sorbitan palmitate.

Other particularly preferred nonionic surfactants are silicone- or siloxane-based emulsifying polymers having alkoxylated groups and/or side chains such as Cetyl PEG/PPG-10/1 Dimethicone (tradename Abil® EM 90); Bis-PEG/PPG-16/16 PEG/PPG-16/16 Dimethicone, commercially available in a mixture with Caprylic/Capric Triglyceride (tradename Abil® Care 85); Bis-PEG/PPG-20/5 PEG/PPG-20/5 Dimethicone and PEG/PPG-25/4 Dimethicone, commercially available in a mixture with Caprylic/Capric Triglyceride (tradename Abil® Care XL 80); Cetyl PEG/PPG-10/1 Dimethicone, commercially available in a mixture with Polyglyceryl-4 Isostearate and Hexyl Laurate (tradename Abil® WE 09); Bis-(Glyceryl/Lauryl) Glyceryl Lauryl Dimethicone, commercially available in a mixture with Caprylic/Capric Triglyceride (tradename Abil® EM 120); Bis-PEG/PPG-14/14 Dimethicone, commercially available in a mixture with dimethicone (tradename Abil EM 97 S), all commercially available from the company, Evonik Goldschmidt GmbH.

Typically, the ionic surfactants contain a lipophilic hydrocarbon group and a polar functional hydrophilic group.

The following anionic surfactants, which may be used alone or as mixtures, may be mentioned: mention may be made especially of the salts, in particular the alkali metal salts such as the sodium salts, the ammonium salts, the amine salts, the amino alcohol salts or the salts of alkaline-earth metals, for example of magnesium, of the following compounds: alkyl sulfates, alkyl ether sulfates, alkylamido ether sulfates, alkylaryl polyether sulfates, monoglyceride sulfates; alkylsulfonates, alkyl phosphates, alkylamidesulfonates, alkylarylsulfonates, a-olefin sulfonates, paraffin sulfonates; alkyl sulfosuccinates, alkyl ether sulfosuccinates, alkylamide sulfosuccinates; alkyl sulfoacetates; acylsarcosinates; and acylglutamates, the alkyl or acyl groups of all these compounds comprising from 6 to 24 carbon atoms and the aryl group preferably denoting a phenyl or benzyl group. It is also possible to use esters of C6-C24 alkyl and of polyglycoside-carboxylic acids, such as alkyl glucoside citrates, polyalkyl glycoside tartrates and polyalkyl glycoside sulfosuccinates; alkyl sulfosuccinamates, acyl isethionates and N-acyltaurates, the alkyl or acyl group of all these compounds containing from 12 to 20 carbon atoms. Among the anionic surfactants that may also be used, mention may also be made of acyl lactylates in which the acyl group contains from 8 to 20 carbon atoms. Mention may also be made of alkyl-D-galactosideuronic acids and salts thereof, and also polyoxyalkylenated (C6-C24)alkylether-carboxylic acids, polyoxyalkylenated (C6-C24)alkyl(C6-C24)arylethercarboxylic acids and polyoxyalkylenated (C6-C24)alkylamidoethercarboxylic acids and salts thereof, in particular those comprising from 2 to 50 ethylene oxide groups, and mixtures thereof.

Among the preferred anionic surfactants, mention may be made of the salts, in particular of sodium, of magnesium or of ammonium, of alkyl sulfates; of alkyl ether sulfates, for instance sodium lauryl ether sulfate, preferably containing 2 or 3 mol of ethylene oxide; of acyl glutamates, for instance, disodium stearoyl glutamate and sodium stearoyl glutamate; of alkyl ether carboxylates; and mixtures thereof, the alkyl or acyl groups generally containing from 6 to 24 carbon atoms and preferably from 8 to 16 carbon atoms.

Among the cationic surfactants, mention may be made of:
i) alkylpyridinium salts, ammonium salts of imidazoline, diquaternary ammonium salts, and ammonium salts containing at least one ester function;
ii) quaternary ammonium salts having the following general formula:

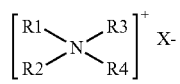

(I)

in which the radicals R1 to R4, which may be identical or different, represent a linear or branched aliphatic radical containing from 1 to 30 carbon atoms, or an aromatic radical such as aryl or alkylaryl; the aliphatic radicals may optionally comprise heteroatoms (O, N, S or halogens) and may optionally, be substituted.

The aliphatic radicals are chosen, for example, from C12-C22 alkyl, alkoxy, C2-C6 polyoxyalkylene, alkylamide, (C12-C22)alkylamido(C2-C6)alkyl, (C12-C22)alkylacetate and hydroxyalkyl radicals, containing from 1 to 30 carbon atoms. X— is an anion chosen from the group of halides, phosphates, acetates, lactates, C2-C6 alkyl sulfates and alkyl or alkylarylsulfonates.

iii) quaternary ammonium salts of imidazoline of formula:

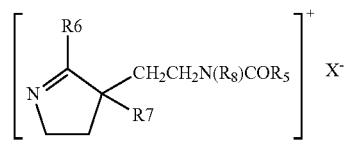

(II)

in which:
R5 represents an alkenyl or alkyl radical containing from 8 to 30 carbon atoms, for example fatty acid derivatives of tallow or of coconut,
R6 represents a hydrogen atom, a C1-C4 alkyl radical or an alkenyl or alkyl radical containing from 8 to 30 carbon atoms,
R7 represents a C1-C4 alkyl radical,
R8 represents a hydrogen atom or a C1-C4 alkyl radical,
X' is an anion chosen from the group of halides, phosphates, acetates, lactates, C2-C6 alkyl sulfates, alkylsulfonates or alkylarylsulfonates.

R5 and R6 preferably denote a mixture of alkenyl or alkyl radicals containing from 12 to 21 carbon atoms, such as, for example, fatty acid derivatives of tallow, R7 denotes methyl and R8 denotes hydrogen. Such a product is, for example, Quaternium-27 (CTFA 1997) or Quaternium-83 (CTFA 1997), which are sold under the names Rewoquat® W75, W90, W75PG and W75HPG by the company Witco,
iv) diquaternary ammonium salts of formula:

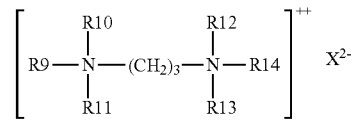

(III)

in which:
R9 denotes an aliphatic radical containing from about 16 to 30 carbon atoms,
R10, R11, R12, R13 and R14, which may be identical or different, are chosen from hydrogen and an alkyl radical containing from 1 to 4 carbon atoms, and
X— is an anion chosen from the group of halides, acetates, phosphates, nitrates, ethyl sulfates and methyl sulfates.

Such diquaternary ammonium salts in particular comprise propanetallowdiammonium dichloride;
v) quaternary ammonium salts containing at least one ester function, such as those of formula:

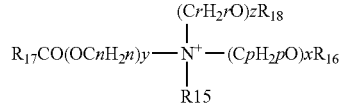

(IV)

in which:
R15 is chosen from C1-C6 alkyl radicals and C1-C6 hydroxyalkyl or dihydroxyalkyl radicals;
R16 is chosen from the radical R19-CO—, linear or branched, saturated or unsaturated C1-C22 hydrocarbon-based radicals R20, a hydrogen atom;

R18 is chosen from the radical R21-CO, linear or branched, saturated or unsaturated C1-C22 hydrocarbon-based radicals R22, a hydrogen atom;

R17, R19 and R21, which may be identical or different, are chosen from linear or branched, saturated or unsaturated C7-C21 hydrocarbon-based radicals;

r, n and p, which may be identical or different, are integers ranging from 2 to 6;

y is an integer ranging from 1 to 10;

x and z, which may be identical or different, are integers ranging from 0 to 10;

X— is a simple or complex organic or mineral anion;

with the proviso that the sum x+y+z is from 1 to 15, that when x is 0, then R16 denotes R20 and that when z is 0, then R18 denotes R22.

The alkyl radicals R15 may be linear or branched, and more particularly linear. Preferably, R15 denotes a methyl, ethyl, hydroxyethyl or dihydroxypropyl radical, and more particularly a methyl or ethyl radical.

Advantageously, the sum x+y+z is from 1 to 10.

When R16 is a hydrocarbon-based radical R20, it may contain from 12 to 22 carbon atoms, or contain from 1 to 3 carbon atoms.

When R18 is a hydrocarbon-based radical R22, it preferably contains 1 to 3 carbon atoms.

Advantageously, R17, R19 and R21, which may be identical or different, are chosen from linear or branched, saturated or unsaturated C11-C21 hydrocarbon-based radicals, and more particularly from linear or branched, saturated or unsaturated C11-C21 alkyl and alkenyl radicals.

Preferably, x and z, which may be identical or different, are equal to 0 or 1. Advantageously, y is equal to 1.

Preferably, r, n and p, which may be identical or different, are equal to 2 or 3 and even more particularly equal to 2.

The anion X— is preferably a halide (chloride, bromide or iodide) or a C1-C4 alkyl sulfate, more particularly methyl sulfate. The anion X— may also represent methanesulfonate, phosphate, nitrate, tosylate, an anion derived from an organic acid (such as acetate or lactate), or any other anion that is compatible with the ammonium containing an ester function.

The surfactants may be, for example, the salts (chloride or methyl sulfate) of diacyloxyethyldimethylammonium, of diacyloxyethylhydroxyethyldimethylammonium, of monoacyloxyethylhydroxyethyldimethylammonium, of triacyloxyethylmethylammonium, of monoacyloxyethylhydroxyethyldimethylammonium, and mixtures thereof. The acyl radicals preferably contain 14 to 18 carbon atoms and are more particularly derived from a plant oil, for instance palm oil or sunflower oil. When the compound contains several acyl radicals, these radicals may be identical or different. Such compounds are sold, for example, under the names Dehyquart® by the company Cognis, Stepanquat® by the company Stepan, Noxamium® by the company Ceca, and Rewoquat® WE 18 by the company Rewo-Goldschmidt.

vi) quaternary ammonium salts and in particular behenyltrimethylammonium chloride, dipalmitoylethylhydroxyethylmethylammonium methosulfate, cetyltrimethylammonium chloride, quaternium-83, behenylamidopropyl-2,3-dihydroxypropyldimethylammonium chloride and palmitylamidopropyltrimethylammonium chloride.

Other suitable cationic surfactants are esterquats which are quaternary ammonium compounds having fatty acid chains containing ester linkages.

Among the preferred cationic surfactants, mention may be made of compounds of formula (I) chosen from cetrimonium chloride, behentrimonium chloride, Behenyl PG-Trimonium chloride, dicetyl dimonium chloride, and mixtures, thereof.

Other preferred cationic surfactants are esterquats chosen from Dibehenoylethyl Dimonium Chloride, Dipalmitoylethyl Dimonium Chloride, Distearoylethyl Dimonium Chloride, Ditallowoyl PG-dimonium Chloride, Dipalmitoylethyl hydroxyethylmonium methosulfate, Distearoylethyl hydroxyethylmonium methosulfate, and mixtures, thereof.

Without being bound by any one theory, it is believed that the presence of an ionic surfactant, particularly, at the time of making the dispersion, reduces or minimizes the aggregation of the particles in the aqueous dispersion of the present disclosure. Thus, the surfactant mixture comprising at least one ionic surfactant acts as a dispersant to facilitate the uniform dispersion of the particles and to enhance the stabilization of the dispersion itself.

In certain embodiments of the present disclosure, the surfactant mixture contains at least one nonionic surfactant and at least one ionic surfactant comprising at least one anionic surfactant.

In other embodiments, the surfactant mixture contains at least one nonionic surfactant and at least one ionic surfactant comprising at least one cationic surfactant.

In preferred embodiments, the surfactant mixture contains at least one nonionic surfactant and at least one ionic surfactant comprising at least one anionic surfactant wherein the surfactant mixture is free of cationic surfactants.

In yet other preferred embodiments, the surfactant mixture contains at least one nonionic surfactant and at least one ionic surfactant comprising at least one cationic surfactant wherein the surfactant mixture is free of anionic surfactants.

Those skilled in the art will select the best fit between the styrenic block copolymer, wax and/or oil, and surfactant in terms of type and % to get the best dispersions. For example, silicone waxes are generally found to be more compatible with silicone based surfactants.

In certain preferred embodiments, the surfactant mixture of the present disclosure is essentially free of amphoteric surfactants. The term "essentially free of amphoteric surfactants" as used herein means "no free amphoteric surfactants" in the surfactant mixture. "No free amphoteric surfactants" herein means that amphoteric surfactants are not added as a separate component by itself to the surfactant mixture. "Free amphoteric surfactants" as used herein does not include the amphoteric surfactants that may be present as a component in a raw material or ingredient that is added during the process of making the aqueous dispersion or composition of the invention. "Free amphoteric surfactants" as used herein also does not include the amphoteric surfactants that may be added as an additional component to the composition of the invention or to the aqueous dispersion after the particles of dispersion are prepared.

Amphoteric surfactants include, but are not limited to, aliphatic secondary or tertiary amine derivatives, in which the aliphatic group is a linear or branched chain containing 8 to 22 carbon atoms and containing at least one water-soluble anionic group, such as, for example, a carboxylate, sulfonate, sulfate, phosphate or phosphonate group; mention may also be made of (C8-C20)alkylbetaines, sulfobetaines, (C8-C20)alkyl-amido-(C6-C8)-alkyl-betaines or (C8-C20)alkyl-amido-(C6-C8)-alkylsulfobetaines; and mixtures thereof.

Among the amine derivatives that may be mentioned are amphocarboxyglycinate compounds and amphocarboxypropionate compounds, in particular, disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid, (C8-C20)alkylbetaines, (C8-C20)alkylamido(C6-C8)alkylbetaines and alkylamphodiacetates.

In the cosmetic, dermatology, personal care and pharmaceutical field, the particles and/or dispersions in accordance with the present invention may be used as vehicles for at least one active substance for the preparation of (a) cosmetic and/or dermatological and/or personal care and/or pharmaceutical composition(s).

Thus, a subject of the present invention is also compositions, such as cosmetic or dermatological or personal care or pharmaceutical compositions, comprising at least some particles and/or at least one dispersion as defined above.

Process for Obtaining the Aqueous Dispersions (Dispersion Protocol)

The aqueous dispersions of the present disclosure may be obtained by means of a process comprising at least the steps as follow:

emulsifying a mixture containing an oil gellant comprising at least one styrenic block copolymer; a fatty substance selected from at least one wax having a melting point of greater than 35° C., at least one oil, and mixtures hereof; a surfactant mixture comprising a nonionic surfactant and an ionic surfactant; water, and optionally, at least one additional ingredient selected from an oil gellant other than an oil gellant comprising at least one styrenic block copolymer, colorants, sunscreen agents, volatile solvents, a wax having a melting point of 35° C. or less, fragrance dls, emulsifying polymers, silicas, talc, clays, and mixtures thereof at an emulsification temperature above the melting point of the at least one wax. If two or more waxes are used, the emulsification temperature should be higher than the melting point of the wax with the higher or highest melting point, subjecting the mixture to a process leading to the production of particles, at a temperature at least 5 to 10° C. above the emulsification temperature of the mixture used in the preceding step, and cooling the dispersion thus obtained.

It is pointed out that the combination of ingredients in the first step of the process and the execution of the second step with heating are cumulative conditions necessary for obtaining the particles according to the invention in a controlled manner, resulting in particles that are calibrated to certain properties (e.g., melting point, size, and shape). Thus, the nature of the process exerted on the styrenic block copolymer/fatty substance-surfactant-water mixture determines the properties of the particles to be obtained.

The process according to the invention may, where appropriate, also include a step consisting in diluting the continuous phase of the mixture before the cooling step.

For the purposes of the present invention, the expression "process leading to the production of particles" is intended to denote an action of shear type. This shearing action can be accomplished by mixing the styrenic block copolymer/fatty substance-surfactant-water mixture using a homogenizer/mixer at a specified speed.

Thus, in an embodiment, the particles of the aqueous dispersion of the present disclosure are obtained by a process following the steps of:

(1) heating a fatty substance selected from at least one wax having a melting point of greater than 35° C., at least one oil, and mixtures thereof in order to melt or soften the fatty substance;
(2) optionally, heating with the fatty substance in (1), at least one additional ingredient selected from an oil gellant other than an oil gellant comprising at least one sytrenic block copolymer, colorants, sunscreen agents, a wax having a melting point of 35° C. or less, emulsifying polymers, fragrance oils other than the at least one oil in (1), silicas, talc, clays, and mixtures thereof;
(3) heating an oil gellant comprising at least one styrenic block copolymer;
(4) mixing the fatty substance in (1) or in (2) with the oil gellant in (3) to form a styrenic block copolymer oil gellant/fatty substance blend;
(5) heating a surfactant mixture comprising at least one nonionic surfactant and at least one ionic surfactant and water to form a surfactant/water combination;
(6) mixing, at above room temperature, the styrenic block copolymer oil gellant/fatty substance blend with the surfactant/water combination by a shearing action to form the aqueous dispersion; and
(7) cooling the aqueous dispersion in (6);

wherein when the fatty substance comprises the at least one wax having a melting point of greater than 35° C., the fatty substance is heated to a temperature above the melting point of the at least one wax.

In one embodiment, the fatty substance in the above-described process comprises at least one wax having a melting point of greater than 35° C. and the step of heating in (1) is conducted at a temperature above the melting point of the at least one wax.

In one embodiment, heating step (3) in the above-described process is conducted at a temperature of at least about 120° C.

In one embodiment, the step of mixing in (4) in the above-described process is conducted for at least 30 minutes, or from about 30 minutes up to about 120 minutes.

In another embodiment, the step of mixing in (4) in the above-described process is conducted at a temperature (emulsification temperature) of at least 80° C., such as up to about 150° C. The emulsification temperature is preferably greater than 40° C. and preferably less than 150° C., more preferably, less than 95° C.

In an embodiment, the shearing action in step (6) in the above-described process is conducted at a speed ranging from about 3000 up to about 9000 rpM, such as at about 3000 rpm, or about 4000 rpm, or about 5000 rpm, or about 6000 rpm or about 7000 rpm, or about 8000 rpm or about 9000 rpm. In other embodiments, the shearing action is conducted as a speed greater than 9000 rpm.

In an embodiment, the shearing action in step (6) in the above-described process is conducted at above room temperature, such as from about 50° C. up to about 80° C., or such as from about 60° C. up to about 70° C.

By using different speeds of mixing, it is possible to achieve different volume-basis particle size distributions having peaks in the range of equal to or greater than 1 µm up to about 100 µm, such as from between about 20 µm up to about 70 µm, or from between about 40 µm up to about 65 µm, or from between about 45 µm up to about 65 µm, or from between equal to or greater than 1 µm up to about 20 µm. It is also possible to use other shearing processes such as those described and referred to in US2006/0292095 and US2006/0263438.

The amounts and the types of surfactants in and/or the weight ratios of the surfactants to one another the surfactant mixture and/or the amounts and/or types of styrenic block copolymers and fatty substances employed may also result in particles of different particle sizes such as those listed above.

In certain embodiments, the nonionic surfactant will be employed in an amount of from about 60% to about 95% by weight, or from about 65% to about 90% by weight, or from about 70% to about 90% by weight, including all ranges and subranges therebetween and based on the total weight of the surfactant mixture of the present disclosure.

In one embodiment, the at least one ionic surfactant will be employed in an amount of from about 5% to about 40% by weight, preferably from about 5% to 30% by weight, such as from about 5% to about 20% by weight, including all ranges and subranges therebetween and based on the total weight of the surfactant mixture of the present disclosure.

Preferably, the surfactant mixture, that is, the combined amount of the at least one nonionic surfactant and the at least one ionic surfactant will be employed in an amount of from about 1.0% to about 5% by weight, or such as from about 1.5% to about 3.5% by weight, or such as from about 1.5% to about 3% by weight, including all ranges and subranges therebetween and based on the total weight of the aqueous dispersion.

Thus, in accordance with the process above, the dispersions of the present disclosure comprise particles that are calibrated to specific properties. Moreover, these particles are preferably free of volatile solvents.

Furthermore, in accordance with the process above, other ingredients, such as active ingredients, polymers, and other additional ingredients as described above may be added during the preparation of the dispersion.

Dispersion

In accordance with the process described above, the particles are preferably obtained as a dispersion in an aqueous and/or water-soluble continuous phase. Such a dispersion may also be described as an oil-in-water emulsion or an oil-in-water dispersion.

The particles in accordance with the invention advantageously do not aggregate in the dispersion in which they are obtained, and their granulometric specificities in terms of size and distribution index are advantageously conserved therein.

The aqueous and/or water-soluble continuous phase that is suitable for use in the dispersions of the invention preferably comprises water such as demineralized water or a combination of water and a water-soluble organic solvent.

Among the water-soluble solvents that may be used in the dispersions in accordance with the invention, mention may be made especially of monoalcohols containing from 3+ carbon atoms, glycols, glycol ethers, and polyols, for instance glycerol, ethylene glycol, propylene glycol, butylene glycol, caprylyl glycol, hexylene glycol, dipropylene glycol, diethylene glycol, xylitol, sorbitol, mannitol, maltitol, and polyethylene glycol or mixtures thereof, C3 and C4 ketones, and C2-C4 aldehydes and mixtures thereof.

For the purposes of the present invention, the term "water-soluble solvent" is intended to denote a compound that is liquid at room temperature and water-miscible (miscibility in water of greater than 50% by weight at 25° C. and at atmospheric pressure).

Compositions

The aqueous dispersions of the present disclosure may be formulated into compositions of various galenic forms.

The compositions containing the aqueous dispersions of the present disclosure comprise a carrier (or solvent) which includes, but is not limited to water, volatile and non-volatile organic solvents, silicones, polyols, glycols, glycol ethers, non-silicone oils, and mixtures thereof.

In preferred embodiments, the carrier is a cosmetically, dermatologically or physiologically acceptable carrier that is non toxic, wherein the compositions can be applied onto keratinous substrates such the skin, lips, hair, scalp, lashes, brows, nails or any other cutaneous region of the body. The cosmetically, dermatologically or physiologically acceptable carrier may comprise water and/or one or more of the organic solvents, chosen from lower monoalcohols, such as those containing from about 1 to 5 carbon atoms, for example ethanol and isopropanol; glycol ethers; polyols, including glycols, such as those containing from about 2 to 8 carbon atoms, for example propylene glycol, ethylene glycol, 1,3-butylene glycol, dipropylene glycol, hexylene glycol, and glycerin; hydrocarbons and non-silicone oils, such as, for example, isododecane and mineral oil; silicones, such as dimethicones, cyclomethicones, and cyclopentasiloxane; and mixtures thereof.

When the organic solvent is a volatile solvent, the amount of the volatile organic solvent generally ranges from greater than 0 (e.g., about 0.01%) to about 99%, and in some embodiments from greater than 0 to about 55%, and in some embodiments from greater than 0 to about 2%, by weight, based on the total weight of the composition. In certain embodiments, the amount of volatile organic solvent does not exceed 55% by weight, based on the total weight of the composition. In other embodiments, the amount of volatile organic solvent does not exceed 5% by weight, based on the total weight of the composition. In yet other embodiments, the compositions of the present disclosure are essentially free of volatile organic solvents. The term "essentially free of organic solvents" as used herein means "no free organic solvent." "No organic solvent" herein means that organic solvent is not added as a separate component by itself during the process of making the composition of the invention. "Free organic solvent" as used herein does not include the organic solvent that may be present as a component in a raw material or ingredient that is added during the process of making the composition of the invention.

The carrier can be employed in an amount of from about 70% to about 99% by weight, or such as from about 75% to about 95% by weight, or such as from about 80% to about 90% by weight, including all ranges and subranges therebetween and based on the total weight of the composition.

The aqueous dispersion of the present disclosure may be present in a the compositions of the present disclosure in an amount ranging from about 1% to about 30% by weight, preferably from about 2% to about 20% by weight, more preferably from about 3% to about 15% by weight, even more preferably from about 5% to about 10% by weight, including all ranges and subranges therebetween and based on the total weight of the composition.

In some embodiments, the aqueous dispersion of the present disclosure may be present in a the compositions of the present disclosure in an amount ranging from about 0.5% to about 20% by weight, preferably from about 1% to about 10% by weight, or such as from about 1% to about 5% by weight, or such as from about 1% to about 3% by weight, including all ranges and subranges therebetween and based on the total weight of the composition.

In some embodiments, the amount of the fatty phase comprising the oil gellant/fatty substance combination in the compositions of the present disclosure ranges from less than 1% to about 40% by weight, such as from about 1% to about 40% by weight, or such as from about 5% to about 35% by weight, or such as from about 10% to about 30% by weight, including all ranges and subranges therebetween and based on the total weight of the final composition.

In at least certain exemplary embodiments, the particles of the present invention are not soluble in the carrier or solvent of the composition, and thus remain in particulate form even after evaporation of the solvent. For example, in embodiments where the composition comprises alcohol as a carrier, the particles may remain in particulate form upon evaporation of the alcohol, such as once the composition is applied to a substrate.

In one embodiment, the at least one additional ingredient that may comprise the particles of the present invention is selected from sunscreen agents such that when the aqueous dispersion is formulated or included into a composition containing the above-described carrier, a photoprotective composition is obtained. Thus, another embodiment of the present invention is a method of photoprotecting a keratinous substrate such as skin or hair or scalp, comprising applying to the substrate said photoprotective composition.

In one embodiment, the at least one additional ingredient is selected from colorants such that when the aqueous dispersion is formulated or included into a composition containing the above-described carrier, a makeup or coloring composition, such as a temporary hair color, is obtained. Thus, another embodiment of the present invention is a method of coloring or making up a keratinous substrate such as skin or hair, comprising applying to the substrate said makeup or coloring composition.

Another particular embodiment of the present invention is an aqueous dispersion comprising:
(a) particles having a volume-basis particle size distribution with peaks in the range of equal to or greater than 1 µm up to about 70 µm and wherein the particles comprise:
  (i) an oil gellant comprising at least one styrenic block copolymer; and
  (ii) a fatty substance comprising at least one fragrance oil;
(b) a surfactant mixture comprising:
  (i) at least one nonionic surfactant; and
  (ii) at least one ionic surfactant; and
(c) water.

When the particles of the present disclosure comprise a fragrance oil, the particles can aid in providing a controlled-release fragrance effect such that the fragrance effect can be imparted over a certain period of time and can therefore be a longer-lasting effect. At the same time, such particles comprising fragrance oils can provide shine to a substrate contacted with the above-described dispersion or a composition containing the above-described dispersion.

Other embodiments of the present invention are compositions containing any one of the above-described aqueous dispersions and a carrier comprising water, volatile organic solvents, non-volatile organic solvents, silicones, non-silicone oils, and mixtures thereof.

Auxiliary Agent

The aqueous dispersions and compositions comprising the aqueous dispersion of the present disclosure may additionally contain an auxiliary agent chosen from liquid lipids/oils, waxes, film forming polymers, rheology modifiers, humectants and moisturizing agents, emulsifying agents, structuring agents, propellants, surfactants, shine agents, conditioning agents, cosmetically, dermatologically and pharmaceutically active agents, vitamins, plant extracts, and mixtures thereof.

The lipids and oils may be the same as or may be other than the fatty substance comprising the particles of the aqueous dispersion.

Film-forming polymers include, but are not limited to, synthetic polymers, of free-radical type or of polycondensate type, polymers of natural origin and mixtures thereof, in particular acrylic polymers, polyurethanes, polyesters, polyamides, polyureas and cellulose-based polymers, for instance nitrocellulose.

Representative rheology modifiers include, but are not limited to, thickening agents and may be polymeric and non-polymeric. Exemplary polymeric thickening agents include various native gums. Representative non-polymeric thickening agents include oxyethylenated molecules and especially ethoxylated alkyl or acyl derivatives of polyols.

The rheology modifier(s) include polymers of natural origin and synthetic polymers, including, but not limited to, associative polymers, non-associative thickening polymers, and water-soluble thickening polymers. They may be chosen from nonionic, anionic, cationic, and amphoteric polymers, including acrylate- or acrylic-based polymers, polysaccharides, polyamino compounds, and nonionic, anionic, cationic and amphoteric amphiphilic polymers.

Suitable rheology modifiers include but are not limited to, acrylates copolymers and carbomers, as well as cellulose-based thickeners (e.g., hydroxyethylcellulose, hydroxypropylcellulose, carboxymethylcellulose, cationic cellulose ether derivatives, quaternized cellulose derivatives, etc.), guar gum and its derivatives (e.g., hydroxypropyl guar, cationic guar derivatives, etc.), gums such as gums of microbial origin (e.g., xanthan gum, scleroglucan gum, etc.), gums derived from plant exudates (e.g., gum arabic, ghatti gum, karaya gum, gum tragacanth, carrageenan gum, agar gum and carob gum), pectins, alginates, and starches, cross-linked homopolymers of acrylic acid or of acrylamidopropane-sulfonic acid.

The rheology modifiers of the present disclosure may also be used as film forming agents, depending on the amount employed.

Suitable examples of the rheology modifiers of the present disclosure may be chosen from crosslinked copolymers of (meth)acrylic acid and/or (C1-C6)alkyl esters and from acrylic associative polymers.

Examples of rheology modifiers of the present disclosure are polyacrylate-3, commercially known under the trade name of Viscophobe DB-100 and sold by The Dow Chemical Company, carbomers, commercially known under the trade name of Carbopol polymers and sold by Lubrizol Advance Materials, Inc, acrylates/C10-30 alkyl acrylate crosspolymers, commercially known the trade names of Pemulen TR-1 and Pemulen TR-2 polymers and sold by Lubrizol Advance Materials, Inc, AMP-acrylates/allyl methacrylate copolymer, commercially known under the trade name of Fixate G-100 polymer and sold by Lubrizol Advance Materials, Inc., polyvinylpyrrolidone, commercially known under the trade name of PVP and sold by International Specialty Products, and a crosslinked methacrylic acid/ethyl acrylate copolymer, also known as an acrylates copolymer in aqueous dispersion, such as the slightly cross-linked, alkali-swellable acrylate polymer known by the INCI name acrylates copolymer and sold by Lubrizol, under the tradename Carbopol® Aqua SF-1 as an aqueous dispersion comprising about 30% by weight of total solids or active material.

The rheology modifier is typically present in an amount ranging from about 0.01% to about 10% by weight, in some embodiments from about 0.1% to about 5% by weight, based on the total weight of the composition.

Suitable examples of humectants and moisturizing agents include, but are not limited to urea, hydroxyethyl urea, polyols such as glycerin, and glycosaminoglycans (GAGs). Suitable examples of glycosaminoglycans are hyaluronic acid or hyaluronan (HA), heparan sulfate (HS), heparin (HP), chondroitin, chondroitin sulfate (CS), chondroitin 4-sulfate or chondroitin sulfate A (CSA), chondroitin 6-sulfate or chondroitin sulfate C (CSC), dermatan sulfate or chondroitin sulfate B (CSB) and keratan sulfate (KS).

Representative examples of propellants include n-butane, isobutane, propane, dimethyl ether, C2-C5 halogenated hydrocarbons, e.g., 1,1-difluoroethane, difluoroethane, chlorodifluoroethane, dichlorodifluoromethane, chlorodifluoromethane, trichlorofluoromethane, hydrofluorocarbon, and mixtures thereof. The amount of the propellant generally ranges from about 1 to about 55%, and in some embodiments from about 1 to about 35%, by weight, and in some embodiments from about 1 to about 20%, by weight and in some embodiments from about 2 to about 15%, by weight based on the total weight of the composition.

The surfactants employed as auxiliary agents may be chosen from the earlier described anionic, cationic, nonionic and amphoteric surfactants.

The shine agents may be chosen from silicones, oils, ethoxylated oils, fats, esters, transesters, hydrocarbons, quats and mixtures thereof.

The aqueous dispersions of the present disclosure may additionally comprise one or more additives chosen from pearlescent agents, opacifying agents, fragrances, sequestering agents, softeners, antifoams, wetting agents, spreading agents, dispersants, plasticizers, mineral fillers, colloidal minerals, peptizers, preserving agents, and pH adjusters.

The compositions comprising the aqueous dispersions of the present disclosure may be in the form of an aqueous system, a simple or complex emulsion (oil-in-water (o/w), water-in-oil (w/o), silicone-in-water and/or water-in-silicone emulsion types) such as a cream or a milk, in the form of a gel or a cream-gel, or in the form of a lotion, a powder or a solid tube, and may optionally be packaged as an aerosol and may be in the form of a mousse or a spray. The mousse or spray may contain propellants such as those listed above.

Spray compositions, especially aerosols, typically contain at least one volatile organic compound (VOC). For essentially ecological reasons and governmental regulations in various countries, it is sought or even necessary to reduce the amount of volatile organic compounds (VOCs) present in the composition. To reduce the amount of VOC and to obtain a low-VOC aerosol device, the organic solvents, for instance ethanol and dimethyl ether, are partially replaced with water.

When the compositions of the present disclosure are emulsions, they will generally contain at least one emulsifier/surfactant chosen from amphoteric, anionic, cationic and nonionic emulsifiers or surfactants, alone or as a mixture.

In another embodiment of the invention, the subject compositions are formulated as water-in-silicone (W/Si) or silicone-in-water (Si/W) emulsions in which the continuous oily phase comprises at least one silicone oil. For water-in-silicone emulsions, the silicone oils are preferably present in a proportion of at least 5% and preferably ranging from 10% to 45% by weight based on the total weight of the emulsion. The fatty phase of the water-in-oil emulsions according to the invention can additionally comprise hydrocarbon-comprising oil(s) of up to 40% by weight with respect to the total weight of the fatty phase of the emulsion.

For the W/Si emulsions, examples of emulsifiers generally include polyether-modified silicones having a long chain of dimethyl siloxane units which carry polyethoxy-polypropoxy units in the chain and at the ends. Examples include cyclopentasiloxane PEG/PPG-18/18 dimethicone, PEG-12 Dimethicone, and PEG/PPG-19/19 Dimethicone sold by Dow Corning as Dow Corning® BY 11-030.

In various embodiments, the composition described herein have a pH ranging from about 2 to about 9, such as about 3 to about 8, or about 4 to about 7.

The aqueous dispersion and compositions of the present disclosure may be applied onto substrates chosen from keratinous substrates such as skin and hair, hard surfaces, such as wood, glass, resin, and metal, and other non-keratinous substrates such as synthetic fibers, fabric, and paper.

In other embodiments, the application of an external stimuli such as heat onto a treated substrate may be desirable or required in order to impart additional benefits to the treated substrate.

Thus, in certain embodiments, a method of coating a substrate is provided, wherein said method involves applying onto the substrate, the aqueous dispersion of the present disclosure and a carrier, and heating the substrate. Preferably, the heat applied to the substrate is at a temperature greater than the melting point of the fatty substances, such as the wax, which comprise the particles of the aqueous dispersion. If two or more waxes comprise the particles of the wax, the heat applied to the substrate should be at a temperature greater than the melting point of the wax with the highest melting point.

Heating tools and equipment/devices can be used as a means to deliver heat or an elevated temperature to the substrate. The heating tools can generate heat through electrical current or heating lamps.

Although not wishing to be bound by any particular theory, it is believed that when the heat applied to the substrate is at a temperature greater than the melting point of the fatty substances, e.g., the wax, which comprise the particles of the aqueous dispersion, the particles are activated by heat and they melt or become liquid-like; when the temperature is lowered or upon cooling the substrate, a film or coating is formed on the substrate.

The terms "film," "coat" and "coating" as used herein with respect to the aqueous dispersion or the composition containing the aqueous dispersion that is applied onto the surface of a substrate can be a continuous or a discontinuous film or coat that adheres to the substrate, and especially to keratin substrates.

The term "discontinuous" means that there breaks, gaps or interruptions in the film or coat produced when an aqueous dispersion or a composition containing the aqueous dispersion of the present disclosure is applied onto a substrate.

Although not wishing to be bound by theory, it is believed that when the aqueous dispersion or composition containing the dispersion is spread on the surface of the substrate, the particles in the aqueous dispersion form linkages of particles on the surface of the substrate such that a continuous or discontinuous film or coat is formed on the surface of the substrate.

Thus, in particularly preferred embodiments, the particles in the compositions containing the aqueous dispersion of the present disclosure are heat-activated particles.

The term "heat-activated" means that the particles of the aqueous dispersion of the invention can melt or soften when heat is used as a stimulus.

The substrate may be heated or exposed to heat before or after treating the substrate with the aqueous dispersion or the composition containing the aqueous dispersion of the present disclosure. The substrate, such as keratinous fibers or textile fibers, may also be molded or shaped or positioned as desired while being heated or exposed to heat. It was surprising and unexpectedly discovered that heat-activating the particles of the aqueous dispersion of the present invention allowed the compositions containing these dispersions to provide additional benefits to a substrate which has been coated with the composition.

It was surprisingly and unexpectedly discovered that when the particles of the aqueous dispersion of the present disclosure have a volume-basis particle size distribution with peaks in the range of equal to or greater than 1 µm up to about 70 µm, compositions containing the aqueous dispersion adhered well to the substrate coated with said composition, particularly when a heating element or tool was applied onto the substrate which has been coated with the said composition. Although not wishing to be bound by any particular theory, it is believed that when the particles of the aqueous dispersion of the present disclosure have a volume-basis particle size distribution with peaks in the range of equal to or greater than 1 µm up to about 100 µm and are heat-activated, the particles do not spread out too much on the substrate when melted, thereby maintaining the above-described linkages between the particles. As a result, the coating or film on the substrate was not sticky or tacky or brittle and left the substrate with a natural feel.

Without wishing to be bound to any particular theory, it is believed that particles having a volume-basis particle size distribution with peaks in the range of about 20 up to about 70 µm are more effective for creating inter-fiber linkages, thereby holding the fibers in a desired configuration. Additionally, particles in this size range lead to linkages of such small size that it is difficult to feel the film or coating on the hair.

Furthermore, it was surprisingly and unexpectedly discovered that when the particles of the aqueous dispersion of the present disclosure have a volume-basis particle size distribution with peaks in the range of equal to or greater than 1 µm up to about 20 µm, compositions containing the aqueous dispersion provided a coating or film to a substrate that had different properties or that had a different feel to the touch For example, when such compositions are in the form of a mascara, the mascara can impart definition to eyelashes and provide properties of comfort, lash separation and/or lengthening, no or minimal clumping of product on the lashes and improved adhesion of product to the lashes, particularly when a heating element or tool is applied onto lashes which have been coated with the mascara product.

Although not wishing to be bound by any particular theory, it is believed that when the particles of the aqueous dispersion of the present disclosure have a volume-basis particle size distribution with peaks in the range of equal to or greater than 1 µm up to about 20 µm, greater coverage of the substrate is obtained compared to that produced by particles whose volume basis particle size distribution peaks are in the range of 20-70 µm. The greater coverage imparts an impression of increased fiber diameter (volumizing/bodifying). It is also believed that the increased surface area of such particles relative to the larger particles can provide compositions containing such particles with oil control capability by placing more oil control actives in contact with sebum.

The compositions containing the aqueous dispersion of the present disclosure may especially constitute cosmetic, personal care, dermatological, pharmaceutical products such as hair styling, hair straightening/relaxing, hair curling/perming/waving, hair care and hair/skin cleansing products such as scalp treatments, shampoos, conditioners and body washes, suncare and skincare/skin treatment products such as moisturizers, and makeup products such as lipsticks, mascaras, foundation, and eye shadow.

In at least certain exemplary embodiments, the compositions are in the form of hair styling compositions, in any form, such as, for example, a gel, a cream, a foam, a lotion, an emulsion, or a liquid that may be sprayed onto or otherwise applied to the hair. In various embodiments, the composition may be provided in the form of a gel, a mousse, or a spray. In at least certain embodiments, the composition may be applied to the hair by first applying to the hands, and then contacting the hair with the hands; in other embodiments, the composition may be applied directly onto the hair, such as by spraying. The compositions may, in various embodiments, be applied to the hair as a leave-on treatment.

In various embodiments, the application of an external stimuli, such as heat, may be desirable as part of the hair styling process. By way of example only, before, during, or after the composition is applied to wet or dry hair, the hair may be further treated with an external stimuli, for example with heat ranging from about 25° C. to about 250° C. In at least certain embodiments, the hair may also be shaped or positioned as desired while exposed to external stimuli, such as while heated or exposed to heat.

Professional and consumer heating tools can be used as a means to deliver heat or an elevated temperature to the hair. Depending upon the desired style or shape imparted to the hair, these tools include, but are not limited to, heaters, blow dryers, flat irons, hot combs, hot curler sets, steam pods, heated crimpers, heated lash curlers, heated wands/brushes, and hood driers or their combinations thereof.

As described, compositions according to the disclosure may impart a film on a substrate, such as on the hair or on the hand during or after application to the hair. A film formed by the composition may, surprisingly, be clean-feeling and not sticky, as with traditional hair care and styling products. Also surprisingly, the composition may impart a film on the hair that leaves the hair relatively natural and clean-feeling, yet has a flexible coating, leaving little to no residue, allows the hair to be bouncy and springy with little to no frizz or flaking, may impart relatively high definition with individualized curls, style control, volume, and shine, and/or may allow for relatively long-lasting hold and style memory. Furthermore, in at least certain embodiments according to the disclosure, the compositions are not sticky or tacky. A user of hair compositions according to various embodiments described herein may thus feel that the composition is not perceptible or is "invisible," yet still effectively style and/or hold the hair. Additionally, the compositions may have effective hair styling and/or hold properties, even in conditions of high, or relatively high, humidity. In at least certain embodiments according to the disclosure, the compositions may be quick-drying, which may allow drying and/or styling time to be reduced, as well as further improve ease of styling and curl retention.

Furthermore, as described, compositions prepared according to various embodiments may provide for varying degrees of hold to be imparted to a hair style. By way of non-limiting example only, in order to obtain a spiky look to hair of a very short length, a high level of styling hold may be desirable. Or, as a further non-limiting example, in order to obtain a flowing look or to maintain hair curls for hair of medium length or longer length, a light to medium level of style hold may be desirable. By altering the weight amounts of the components comprising the particles of the invention and/or by employing particles of volume-basis particle size distributions with peaks in varying ranges (e.g., from equal to or greater than 1 µm up to about 100 µm, or from about 1 to about 20 µm), it is possible to formulate compositions having high levels of style hold, medium to high levels of style hold, medium levels of style hold, or light to medium levels of style hold.

In at least certain embodiments, a film formed by the compositions described herein may be clear and/or stable. In such embodiments, phase separation and dramatic aggregation are minimized.

In addition, hair styled or treated with compositions according to the disclosure may, in at least certain exemplary embodiments, be hydrophobic, and/or may appear less frizzy and/or may be less prone to breakage, relative to hair subjected to the same conditions but not having been styled or treated with a composition according to the disclosure It should be noted, however, that compositions and films, as well as hair to which the composition or film has been applied, according to the disclosure may not have one or more of the herein-referenced properties, yet are intended to be within the scope of the disclosure.

Also disclosed herein are methods for styling the hair, said methods comprising applying a composition according to the disclosure to the hair, either before, during, or after styling the hair. One or more steps of treating the hair with an external stimulus, such as heat, before, during, or after the composition has been applied to the hair are also contemplated.

Thus, in some embodiments, a method of shaping hair is provided, wherein said method includes a step of applying onto the hair, a composition containing the aqueous dispersion of the present disclosure, and a cosmetically acceptable carrier and a step of applying heat to the hair. Said method may additionally include a step of shaping hair using a means for shaping hair.

The term "shaping hair" as used herein can also mean changing the configuration of hair.

The above-described method allows one to shape/re-shape or re-position the hair on the head, such as to straighten the hair, curl the hair, redefine hair curl, or volumize the hair, and to repeat the steps of said method as many times as desired and without needing to re-apply the composition and/or re-wet the hair.

In particularly preferred embodiments, a means for shaping hair is used. Said means for may be part of the heating tool or may be a separate device or tool such as a brush or comb or curling device. The means for shaping hair may also comprise passing the fingers or the hand through the hair.

The steps of the above-described method for shaping hair may be conducted in any order. For example, the composition containing the aqueous dispersion may first be applied onto hair, followed by applying heat to hair, then followed by shaping the hair using a means for shaping the hair. In another example, heat is applied to the hair first, followed by the step of applying the composition onto the hair, then followed by the step of shaping the hair using a means for shaping the hair. In yet another example, the hair is shaped first, using a means for shaping the hair, followed by applying the composition onto the hair and then applying heat to the hair. In other examples, the hair may be shaped first using a means for shaping the hair, followed by applying heat to the hair and then applying the composition onto the hair and allowing the shape of the hair to set in place as the temperature reaches room temperature.

The compositions containing the aqueous dispersion of the present disclosure may also be in the form of a skin care or treatment composition for greasy or oily hair and skin (including the scalp). In particular, such compositions can reduce or minimize greasy/oil feel or appearance on the skin, scalp or hair.

The compositions containing the aqueous dispersion of the present disclosure may be used to protect the color of artificially colored hair by making the color more fade resistant or wash resistant (i.e., the color stays longer on the hair).

The compositions containing the aqueous dispersion of the present disclosure may also be in the form of household and industrial products.

The compositions of the present invention can be provided in a plethora of galenic forms, including but not limited to creams, liquid, gel, cream-gel, lotion, foam, serum, paste, semi-solid, solid stick, stick-gel, or a powder, and may be in the form of a mousse or a spray, and may optionally be packaged as an aerosol, prepared according to the usual methods.

It is to be understood that both the foregoing description and the following Examples are exemplary and explanatory only, and are not to be interpreted as restrictive of the disclosure. Moreover, it should be understood that various features and/or characteristics of differing embodiments herein may be combined with one another. It is therefore to be understood that numerous modifications may be made to the illustrative embodiments and that other arrangements may be devised without departing from the scope of the disclosure. Other embodiments will be apparent to those skilled in the art from consideration of the disclosure and practice of the various exemplary embodiments disclosed herein.

Unless otherwise indicated, all numbers used in the specification and claims are to be understood as being modified in all instances by the term "about," whether or not so stated. The term "about" as it modifies numbers herein is meant to indicate a difference of 10% or less from the stated number, such as 9% or less, such as 8% or less, such as 7% or less, such as 6% or less, such as 5% or less, such as 4% or less, such as 3% or less, such as 2% or less, or such as 1% or less, in various exemplary embodiments. Thus, by way of example only, in one embodiment where "about" indicates a difference of 10% or less, the phrase "about 20%" is intended to encompass a range from 18%-22%. In another exemplary embodiment where "about" indicates a difference of 5% or less, the phrase "about 20%" is intended to encompass a range from 19%-21%. All such numbers within each specified range are hereby explicitly intended to be included in the disclosure.

It should also be understood that the precise numerical values used in the specification and claims form additional embodiments of the disclosure, and are intended to include any ranges which can be narrowed to any two end points disclosed within the exemplary ranges and values provided, as well as the specific end points themselves. Efforts have been made to ensure the accuracy of the numerical values disclosed herein. Any measured numerical value, however, can inherently contain certain errors resulting from the standard deviation found in its respective measuring technique.

It should be understood that compositions according to various embodiments of the disclosure form a film when applied to a substrate. However, the various properties of the film described herein are intended to include any film provided by compositions according to the disclosure, regardless of whether the film is attached or bonded to the substrate or not.

The following examples of dispersions and of compositions are intended to illustrate the invention without limiting the scope as a result. The percentages are given on a weight basis.

EXAMPLES

Example I

Based on the Dispersion Protocol described above, the aqueous dispersion and compositions containing the aqueous dispersion of the invention were prepared/manufactured as follow:

A. Aqueous Surfactant Solution:
1. A surfactant mixture was prepared by adding gram amounts of nonionic surfactant(s) and ionic surfactant(s) in a container.
2. Deionized water was added in an amount such that the final weight of the aqueous dispersion (including the weight of the wax) is 100 grams.
3. The surfactant solution was heated to a temperature within the range of about 80° C. to about 85C.° in a water bath.

B. Block copolymer/fatty substance blend preparation: Fatty substances were melted and heated to a temperature appropriate for blending with the polymer (120° C. generally for Kraton SBC materials). The polymer was then added to the melted/molten fatty substance and the mixture was mixed while maintaining the temperature until a homogenous mixture was formed (30-120 minutes). The mixture is then cooled to the emulsification temperature (80-85° C.).

C. Emulsification Process
1. While the aqueous surfactant solution was still at an elevated temperature (above room temperature, such as from about 65° C. to about 70° C.), the solution was mixed using a homogenizer/mixer (e.g., Silverson homogenizer) at a speed ranging from about 3000 to about 9000 rpm.
2. The heated blend (still at a temperature above room temperature) was added to the surfactant solution close to the mixing head of the homogenizer while mixing.
3. Once all the heated blend was added, mixing was continued for at least 5 minutes.
4. The homogenizer blade was removed and the emulsion (aqueous dispersion) was mixed and cooled slightly towards room temperature to form the particles of polymer/wax and/or oil. The dispersion was then transferred into another container or when a composition containing the aqueous dispersion is to be made, then other ingredients comprising the composition are combined at this stage and an aliquout of the aqueous dispersion is added to the composition.
5. The dispersion or composition was stored at room temperature.
6. The protocol above is followed for preparing other aqueous dispersions of the present invention using different sytrenic block copolymers and/or fatty substances (waxes and oils) and/or surfactants at different levels.
7. The particle sizes of the particles comprising the dispersion were determined by measuring the particle size distribution ("PSD") based on volume using laser diffraction methods a using a Shimadzu SALD-7001 laser diffraction particle size analyzer and quartz cuvettes having a refractive index of 1.2.

TABLE 1

Examples of aqueous dispersions prepared according to the Dispersion Protocol above

| Ingredient/ INCI Name | Commercial Name | Supplier | Aqueous Dispersion I % weight of ingredient | Aqueous Dispersion II % weight of ingredient | Aqueous Dispersion III % weight of ingredient |
| --- | --- | --- | --- | --- | --- |
| PEG-30 glyceryl stearate (nonionic surfactant) | Tagat S | Evonik Goldschmidt | 2.70 | 2.5 | 1.35 |
| Disodium stearoyl glutamate (anionic surfactant) | Amisoft HS 21 P | Ajinmoto | 0.30 | 0.5 | 0.15 |
| Beeswax* | White Beeswax SP 453P | Strahl & Pitsch | 27.60 | 27.60 | 27.60 |
| Hydrogenated Styrene/ Butadiene Copolymer* | G1657 MS | Kraton Polymer | 2.40 | 2.40 | 2.40 |
| Water | | | Q.S. 100 | Q.S. 100 | Q.S. 100 |

*The combination of beeswax and gellant is an 8% Kraton G1657 MS/92% Beeswax blend at 30% by weight, based on the total weight of the dispersion.

The particles in the aqueous dispersions above had peaks in their volume-basis particle size distribution ("PSD") in the range of equal to or greater than 1 μm up to about 100 μm.

Example II

Examples of Formulations Containing the Aqueous Dispersion

Formulas below were individually prepared from the aqueous dispersion of Example 1 by adding an aliquot of Aqueous dispersion I to the rest of the ingredients in the exemplified Formulas.

Formula 1—Styling Lotion

| Ingredient/INCI Name | % weight of ingredient |
| --- | --- |
| HYDROXYPROPYL GUAR | 0.60 |
| HYDROXYETHYLCELLULOSE | 0.50 |
| PHENOXYETHANOL | 0.90 |
| CAPRYLYL GLYCOL | 0.50 |
| ETHYLHEXYLGLYCERIN | 0.10 |

-continued

| Ingredient/INCI Name | % weight of ingredient |
|---|---|
| DIMETHICONE (and) DIMETHICONOL | 2.55 |
| ISOPROPYL MYRISTATE | 1.00 |
| 8% Kraton G1657 MS/ 92% Beeswax dispersion of EX 1 | 8.33 |
| WATER | Q.S. 100 |

Formula 2—Pump Spray

| Ingredient/INCI Name | % weight of ingredient |
|---|---|
| ACRYLATES COPOLYMER CARBOPOL AQUA SF-1 POLYMER (Lubrizol)/30% active | 2.00 |
| TRIETHANOLAMINE | 0.2 |
| PEG-14 DIMETHICONE ABIL B 8842 (Evonik Goldschmidt) | 0.50 |
| PHENOXYETHANOL | 0.90 |
| CAPRYLYL GLYCOL | 0.50 |
| ETHYLHEXYLGLYCERIN | 0.10 |
| 8% Kraton G1657 MS/ 92% Beeswax dispersion of EX 1 | 8.33 |
| WATER | Q.S. 100 |

Formula 3 (pump foam)

| Ingredient/INCI Name | % weight of ingredient |
|---|---|
| DISODIUM EDTA | 0.10 |
| METHYLPARABEN | 0.25 |
| PHENOXYETHANOL | 0.50 |
| DECYLGLUCOSIDE | 1.00 |
| OLETH-20 | 1.50 |
| DIMETHICONE PEG-7 COCOATE | 0.3 |
| POLYQUATERNIUM-11 | 3.00 |
| POLYQUATERNIUM-22 | 1.50 |
| 8% Kraton G1657 MS/ 92% Beeswax dispersion of EX 1 | 8.33 |
| WATER | Q.S. 100 |

Formula 4 (aerosol foam—mousse)

| Ingredient/INCI Name | % weight of ingredient |
|---|---|
| Isobutane/Propane | 6 |
| HYDROXYPROPYL GUAR | 0.2 |
| ACRYLATES/C10-30 ALKYL ACRYLATE CROSSPOLYMER CARBOPOL ULTREZ 20 POLYMER (Lubrizol) | 0.50 |
| PHENOXYETHANOL | 0.80 |
| CAPRYLYL GLYCOL | 0.90 |
| METHYLISOTHIAZOLINONE | 0.08 |
| PEG-14 DIMETHICONE ABIL B 8842 (Evonik Goldschmidt) | 0.50 |
| DECYL GLUCOSIDE PLANTACARE 2000 UP (Cognis (BASF)) | 0.50 |
| TRIETHANOLAMINE | 0.20 |
| 8% Kraton G1657 MS/92% Beeswax dispersion of EX 1 | 8.33 |
| WATER | Q.S. 100 |

Example III

Testing on Hair

The aqueous dispersion was applied onto hair swatches. It was observed that the hair was neither sticky or tacky.

Formula 1 above as tested on the hair of human models of Caucasian and African ethnicities and with medium to long hair. Stylists washed the models' hair, then heat styled the hair using their preferred methods.

The stylists found that the use of the formula made styling hair easier, noting in particular the superior performance on hair near the root that had not been chemically straightened. They also found the formula to be very easy to apply and formula left hair feeling clean and natural with a natural level of movement, provided frizz control, excellent smoothing and straightening with heat and facilitated or speeded up the blow-drying process. In addition, the stylist found that the hair treated or contacted with the formula demonstrated abundantly more shine These tests demonstrated effective shaping of the hair without leaving the hair coated by materials which impart an unpleasant feel and glue hair unnaturally in place.

In a second study, human volunteers of Caucasian and Hispanic ethnicities tested Formula 1 on their hair according to their normal hair care regimen. The volunteers were selected according to hair type and usual styling routines (i.e. use of blow dryer, flat iron, etc.). The volunteers found that the formula made styling the hair easier, the baseline requirement for a styling product. Additionally, this styling ease persisted several days. They also found the formula to leave the hair feeling natural or uncoated and having a natural movement. Imposed styles were durable throughout the day. Additionally, the accumulation of detectable sebum at the scalp was reduced sufficiently such that the volunteers were able to comfortably delay their subsequent shampooing by a day or more as desired.

These findings demonstrated that the styling effects imparted by the composition of the invention were durable, indicating that the dispersion particles formed linkages on the hair such that the particles remained on the hair, thereby allowing the styling ease to persist for subsequent days beyond the initial styling event (application of the formula on hair). Furthermore, the formula on the hair left the hair feeling uncoated and moving naturally. Also, the components of the formula gave an oil control effect, thereby delaying the need for washing the hair.

It was also observed that after treating the hair with the formulas and heating the treated hair using a blow dryer, the hair was easily configured into a desired shape. Upon cooling, it was observed that the formulas did not give a sticky or tacky feel to the hair. Moreover, upon re-heating the hair with the blow-dryer or other suitable devices such as flat iron and curlers, the hair could be re-positioned/re-shaped to a different configuration without having to reapply the formulas onto the hair.

Example IV

Comparative Data

The properties of a blend material obtained from the combination of a styrenic block copolymer such as Kraton G1657 M with a wax were compared to the properties obtained by using wax alone. As the amount of the styrenic block copolymer in the blend material was increased, the modulus of films the blend material on the surface of hair and the tackiness of the blend material were measured.

Tack Measurements

Instrument: Texture Technologies TA.XT Plus Texture Analyzer

Samples were melt-formed discs of wax blends approximately 0.75 mm thick. The metal ball probe was used for all testing. The standard adhesive test was used with the following modifications: Post-test speed: 0.5 mm/s; Applied force: 250 g for data in FIG. 1, 100 g for data in FIG. 2

Modulus

Instrument: TA Q800 DMA

Samples were cut from thin (approximately 0.75 mm thick), melt-formed discs of wax blends. Strips had approximate dimensions (L×W×T) of 15 mm×5.5 mm×0.75 mm. Precise dimensions were measured using calipers.

The standard strain sweep measurement was used to measure the complex modulus of strips of wax blends at ranges of 0.5 μm to 50 μm displacement. The resulting data allowed identification of strain ranges of predominantly linear behavior. The reported modulus for each sample comes from this linear range. Measurements were repeated in triplicate. Reported values are the mean; reported error bars are standard deviations of these measurements.

TABLE 1

Wax alone and Wax/polymer blend

| % polymer (Kraton G1657 MS) | Modulus (MPa) | Tack (g) |
|---|---|---|
| 0 (beeswax only) | 183.90 | 121.74 |
| 3.75 | 304.73 | 43.88 |
| 8 | 324.93 | 39.28 |
| 15 | 331.33 | 42.46 |

The results in the table above show significant difference in the modulus and tack values as measured from the wax alone compared to those from the wax/polymer blend. The results are also represented by a chart in FIG. 1.

The results also show an increase in the modulus when the polymer was combined with the wax and that the modulus increased with increasing amounts of the polymer. At the same time, the tack value decreased when the polymer was combined with the wax and the tack decreased with increasing amounts of the polymer. These results indicate that the incorporation of the polymer increased the stiffness of the blend material while simultaneously reducing the tackiness of the blend material. The increased stiffness indicates that the stronger linkages between the particles of the aqueous dispersion can be achieved such that when the dispersion is included in a final composition, improved and durable shaping effects are obtained when the composition is applied to a substrate such as hair. At the same time, the reduced tackiness of the blend material indicates that the final composition can impart a clean and natural feel to the substrate.

On the other hand, the comparatively lower modulus of beeswax alone indicates that the linkages between the wax and the hair are less able to maintain the shape of the fiber. Additionally, the tackiness of the wax translates to a less natural feel on the hair, i.e., the wax on the surface of the hair can be readily felt since hair that has not been contacted with any product that is left on the hair.has essentially no tack.

Example V

Oil Sebum Study

The tackiness of a wax and the tackiness of a blend material comprising wax and 8% styrenic block copolymer were measured as a function of added synthetic oil sebum. The test was conducted on the hair of volunteers in a salon.

TABLE 2

| % Sebum* | 100% Beeswax/ 0% Polymer Tack (g) | 92% Beeswax/ 8% Polymer Tack (g) |
|---|---|---|
| 0.0% | 11.50 | 8.50 |
| 3.8% | 11.34 | 11.46 |
| 7.4% | 18.00 | 11.18 |
| 13.8% | 27.94 | 23.82 |
| 24.2% | 38.72 | 29.78 |

*sebum added to beeswax alone and to the beeswax/polymer blend

Figure 2:
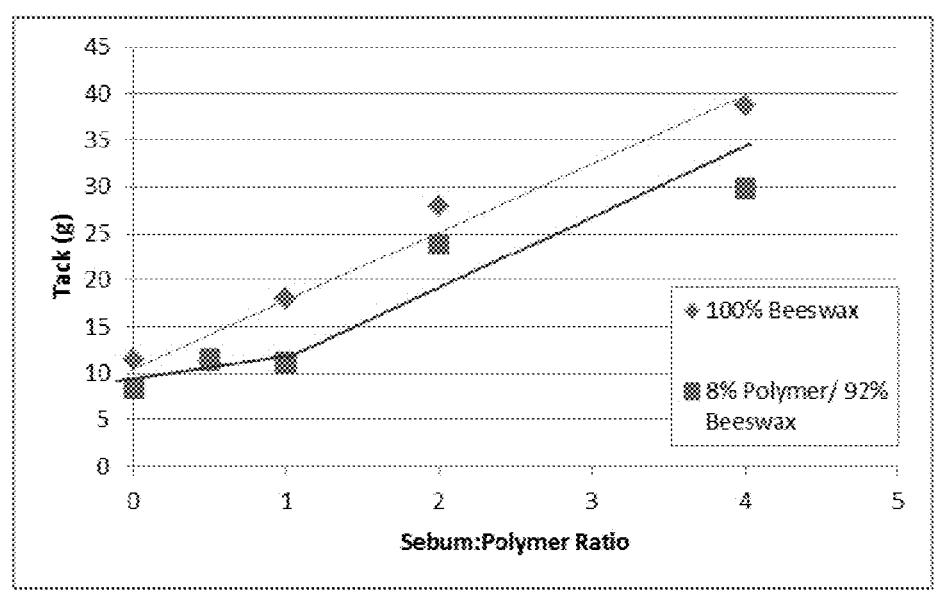
FIG. 2 represents a chart showing the effect of sebum on the tack properties of a wax-styrenic block copolymer mixture and a wax.

The results in the table above are also represented by a chart in FIG. 2. The results indicate that incorporation of the block copolymer can delay the onset of unclean feeling in part by mitigating the effects of sebum on key physical properties. When no polymer was present, tackiness increased significantly with only a small amount of oil sebum. With the polymer was present, tackiness increased slowly with increasing sebum content. When the level of sebum was comparable to that of the polymer, tackiness increased at a rate comparable to that of the wax (no polymer present). These data indicate that the presence of the polymer delays the onset of unclean feeling on hair produced by the natural accumulation of sebum.

It is to be understood that the foregoing describes preferred embodiments of the invention and that modifications may be made therein without departing from the spirit or scope of the invention as set forth in the claims.

What is claimed is:

1. An aqueous dispersion comprising:
   a) particles having a volume-basis particle size distribution with peaks in the range of equal to or greater than 1 μm up to about 100 μm, wherein at least one of the particles comprises:
      (i) an oil gellant comprising at least one styrenic block copolymer; and
      (ii) a fatty substance selected from at least one wax having a melting point of greater than 35° C., at least one oil, and mixtures thereof;
   b) a surfactant mixture comprising:
      (i) at least one nonionic surfactant; and
      (ii) at least one ionic surfactant; and
   c) water.

2. The aqueous dispersion of claim 1, wherein the at least one styrenic block copolymer is selected from a styrene-ethylene/butylene diblock copolymer, a styrene-ethylene/propylene diblock copolymer, a styrene-ethylene/butylene-styrene triblock copolymer, or mixtures thereof.

3. The aqueous dispersion of claim 2, wherein the at least one styrenic block copolymer is selected from a styrene-ethylene/butylene diblock copolymer, a styrene-ethylene/butylene-styrene triblock copolymer, or mixtures thereof.

4. The aqueous dispersion of claim 3, wherein the least one styrenic block copolymer comprises a styrene-ethylene/butylene diblock copolymer and a styrene ethylene/butylene-styrene triblock copolymer.

5. The aqueous dispersion of claim 2, wherein the fatty substance is selected from at least one wax having a melting point of greater than 35° C.

6. The aqueous dispersion of claim 5, wherein the weight ratio of the at least one wax having a melting point of greater than 35° C. to the at least one styrenic block copolymer ranges from about 100:1 to about 1:100.

7. The aqueous dispersion of claim 5, wherein the particles have a volume-basis particle size distribution with peaks in the range of about 20 μm up to about 70 μm.

8. The aqueous dispersion of claim 5, wherein the least one wax having a melting point of greater than 35° C. is selected from beeswax, hydrogenated myristyl olive esters, hydrogenated stearyl olive esters, VP/eicosene copolymer, ditrimethyloylpropane tetrastearate, silsesquioxane resin wax, or mixtures thereof.

9. The aqueous dispersion of claim 8, wherein the at least one wax having a melting point of greater than 35° C. is present in an amount of from 10% to about 60% by weight, based on the total weight of the aqueous dispersion and the least one styrenic block copolymer is present in an amount of from about 0.1% to about 15% by weight, based on the total weight of the aqueous dispersion.

10. The aqueous dispersion of claim 2, wherein the fatty substance is selected from at least one oil.

11. The aqueous dispersion of claim 10, wherein the weight ratio of the at least one oil to the at least one styrenic block copolymer ranges from about 100:1 to about 1:100.

12. The aqueous dispersion of claim 10, wherein the weight ratio of the at least one oil to the at least one styrenic block copolymer ranges from about 5:1 to about 1000:1 and wherein the at least one oil is present in an amount of from about 85% to about 99.9% by weight, based on the total weight of the styrenic block copolymer and the at least one oil.

13. The aqueous dispersion of claim 10, wherein the particles have a volume-basis particle size distribution with peaks in the range of about 20 μm up to about 70 μm.

14. The aqueous dispersion of claim 10, wherein the least one oil is selected from $C_6$-$C_{16}$ alkanes, non-silicone oils of plant, mineral or synthetic origin, liquid fatty alcohols, liquid fatty acids, liquid esters of a fatty acid, liquid esters of a fatty alcohol, silicone oils, fragrance oils, or mixtures thereof.

15. The aqueous dispersion of claim 2, wherein the fatty substance comprises at least one wax having a melting point of greater than 35° C. and at least one oil.

16. The aqueous dispersion of claim 15, wherein the at least one wax having a melting point of greater than 35° C., the at least one oil, and the at least one styrenic block copolymer are each present in an amount of from about 0.1% to about 99.8% by weight, all weights being based on the total weight of the styrenic block copolymer, the wax and the oil.

17. The aqueous dispersion of claim 16, wherein the amount of the at least one wax having a melting point of greater than 35° C. is equal to or greater than the total amount of the at least one oil and the amount of the at least one styrenic block copolymer.

18. The aqueous dispersion of claim 16, wherein the particles have a volume-basis particle size distribution with peaks in the range of about 20 μm up to about 70 μm.

19. The aqueous dispersion of claim 16, wherein the least one wax having a melting point of greater than 35° C. is selected from beeswax, hydrogenated myristyl olive esters, hydrogenated stearyl olive esters, VP/eicosene copolymer, ditrimethyloylpropane tetrastearate, silsesquioxane resin wax, or mixtures thereof.

20. The aqueous dispersion of claim 19, wherein the least one oil is selected from $C_6$-$C_{16}$ alkanes, non-silicone oils of plant, mineral or synthetic origin, liquid fatty alcohols, liquid fatty acids, liquid esters of a fatty acid, liquid esters of a fatty alcohol, silicone oils, fragrance oils, or mixtures thereof.

21. The aqueous dispersion of claim 2, wherein the at least one nonionic surfactant is selected from polyethylene glycol ethers of glyceryl esters, sorbitan esters, silicone-based emulsifying polymers having alkoxylated groups and/or side chains, or mixtures thereof.

22. The aqueous dispersion of claim 21, wherein the at least one ionic surfactant is present in an amount of from about 5% to about 30% by weight, based on the total weight of the surfactant mixture.

23. The aqueous dispersion of claim 22, wherein the at least one ionic surfactant comprises at least one cationic surfactant selected from cetrimonium chloride, behentrimonium chloride, dipalmitoylethyl hydroxyethylmonium methosulfate, distearoylethyl hydroxyethylmonium methosulfate, or mixtures thereof.

24. The aqueous dispersion of claim 22, wherein the at least one ionic surfactant comprises at least one anionic surfactant selected from acyl glutamates, alkyl sulfates and their salts, alkyl ether sulfates and their salts, acyl glutamates, alkyl ether carboxylates, or mixtures thereof.

25. The aqueous dispersion of claim 1, wherein the particles optionally further comprise at least one additional ingredient selected from an oil gellant other than a)(i), colorants, sunscreen agents, a wax having a melting point of 35° C. or less, emulsifying polymers, fragrance oils other than the at least one oil in a)(ii), silicas, talc, clays, or mixtures thereof.

26. The aqueous dispersion of claim 25, wherein the particles are obtained by a process comprising:
    (1) heating the fatty substance;
    (2) optionally, if present, heating the at least one optional additional ingredient with the fatty substance in (1);
    (3) heating the oil gellant comprising at least one styrenic block copolymer;
    (4) mixing the fatty substance in (1) or in (2) with the oil gellant in (3) to form a styrenic block copolymer oil gellant/fatty substance blend;
    (5) heating the surfactant mixture comprising at least one nonionic surfactant and at least one ionic surfactant and the water to form a surfactant/water combination;
    (6) mixing the styrenic block copolymer oil gellant/fatty substance blend with the surfactant/water combination by a shearing action to form the aqueous dispersion; and
    (7) cooling the aqueous dispersion in (6);
    wherein when the fatty substance comprises the at least one wax having a melting point of greater than 35° C., the fatty substance is heated to a temperature above the melting point of the at least one wax having a melting point of greater than 35° C.

27. The aqueous dispersion of claim 26, wherein the step of heating in (3) is conducted at a temperature above the melting point of the at least one wax having a melting point of greater than 35° C.

28. The aqueous dispersion of claim 27, wherein the shearing action is conducted at a speed ranging from about 3000 up to about 9000 rpm.

29. The aqueous dispersion of claim 28, wherein the particles have a volume-basis particle size distribution with peaks in the range of about 20 μm up to about 70 μm.

30. A composition comprising:
    A. an aqueous dispersion containing:
        a) particles having a volume-basis particle size distribution with peaks in the range of equal to or greater than 1 μm up to about 70 μm, wherein at least one of the particles comprises:

(i) an oil gellant comprising at least one styrenic block copolymer; and
(ii) a fatty substance selected from at least one wax having a melting point of greater than 35° C., at least one oil, or mixtures thereof
b) a surfactant mixture comprising:
(i) at least one nonionic surfactant selected from polyethylene glycol ethers of glyceryl esters, sorbitan esters, silicone-based emulsifying polymers having alkoxylated groups and/or side chains, or mixtures thereof; and
(ii) at least one ionic surfactant; and
c) water;
all weights being based on the total weight of the aqueous dispersion;
B. a carrier comprising water, volatile organic solvents, non-volatile organic solvents, silicones, non-silicone oils, or mixtures thereof; and
C. optionally, at least one auxiliary ingredient selected from liquid lipids/oils, waxes, film forming polymers, rheology modifiers, humectants and moisturizing agents, emulsifying agents, structuring agents, propellants, surfactants, shine agents, conditioning agents, cosmetically, dermatologically and pharmaceutically active agents, vitamins, plant extracts, or mixtures thereof.

31. The composition of claim 30, wherein the at least one styrenic block copolymer is selected from a styrene-ethylene/butylene diblock copolymer, a styrene-ethylene/propylene diblock copolymer, a styrene-ethylene/butylene-styrene triblock copolymer, or mixtures thereof.

32. The composition of claim 31, wherein the at least one styrenic block copolymer is selected from a styrene-ethylene/butylene diblock copolymer, a styrene-ethylene/butylene-styrene triblock copolymer, or mixtures thereof.

33. The composition of claim 32, wherein the least one styrenic block copolymer comprises a styrene-ethylene/butylene diblock copolymer and a styrene-ethylene/butylene-styrene triblock copolymer.

34. The composition of claim 31, wherein the fatty substance is selected from at least one wax having a melting point of greater than 35° C.

35. The composition of claim 34, wherein the weight ratio of the at least one wax having a melting point of greater than 35° C. to the at least one styrenic block copolymer ranges from about 100:1 to about 1:100.

36. The composition of claim 35, wherein the particles have a volume-basis particle size distribution with peaks in the range of about 20 μm up to about 70 μm.

37. The composition of claim 34, wherein the least one wax having a melting point of greater than 35° C. is selected from beeswax, hydrogenated myristyl olive esters, hydrogenated stearyl olive esters, VP/eicosene copolymer, ditrimethyloylpropane tetrastearate, silsesquioxane resin wax, or mixtures thereof.

38. The composition of claim 37, wherein the at least one wax having a melting point of greater than 35° C. is present in an amount of from 20% to about 40% by weight, based on the total weight of the aqueous dispersion, and wherein the least one styrenic block copolymer is present in an amount of from about 0.1% to about 15% by weight, based on the total weight of the aqueous dispersion.

39. The composition of claim 31, wherein the fatty substance is selected from at least one oil.

40. The composition of claim 39, wherein the weight ratio of the at least one oil to the at least one styrenic block copolymer ranges from about 100:1 to about 1:100.

41. The composition of claim 39, wherein the weight ratio of the at least one oil to the at least one styrenic block copolymer ranges from about 5:1 to about 1000:1 and wherein the at least one oil is present in an amount of from about 85% to about 99.9% by weight, based on the total weight of the styrenic block copolymer and the at least one oil.

42. The composition of claim 39, wherein the particles have a volume-basis particle size distribution with peaks in the range of about 20 μm up to about 70 μm.

43. The composition of claim 39, wherein the least one oil is selected from $C_6$-$C_{16}$ alkanes, non-silicone oils of plant, mineral or synthetic origin, liquid fatty alcohols, liquid fatty acids, liquid esters of a fatty acid, liquid esters of a fatty alcohol, silicone oils, fragrance oils, or mixtures thereof.

44. The composition of claim 31, wherein the fatty substance comprises at least one wax having a melting point of greater than 35° C. and at least one oil.

45. The composition of claim 44, wherein the at least one wax having a melting point of greater than 35° C., the at least one oil, and the at least one styrenic block copolymer are each present in an amount of from about 0.1% to about 99.8% by weight, all weights being based on the total weight of the styrenic block copolymer, the wax and the oil.

46. The composition of claim 45, wherein the amount of the at least one wax having a melting point of greater than 35° C. is equal to or greater than the total amount of the at least one oil and the amount of the at least one styrenic block copolymer.

47. The composition of claim 46, wherein the particles have a volume-basis particle size distribution with peaks in the range of about 20 μm up to about 70 μm.

48. The composition of claim 44, wherein the least one wax is selected from beeswax, hydrogenated myristyl olive esters, hydrogenated stearyl olive esters, VP/eicosene copolymer, ditrimethyloylpropane tetrastearate, silsesquioxane resin wax, or mixtures thereof.

49. The composition of claim 48, wherein the least one oil is selected from $C_6$-$C_{16}$ alkanes, non-silicone oils of plant, mineral or synthetic origin, liquid fatty alcohols, liquid fatty acids, liquid esters of a fatty acid, liquid esters of a fatty alcohol, silicone oils, fragrance oils, or mixtures thereof.

50. The composition of claim 30, wherein the at least one nonionic surfactant is selected from polyethylene glycol ethers of glyceryl esters, sorbitan esters, silicone-based emulsifying polymers having alkoxylated groups and/or side chains, or mixtures thereof.

51. The composition of claim 50, wherein the at least one nonionic surfactant is selected from PEG-30 glyceryl stearate, sorbitan palmitate, Cetyl PEG/PPG-10/1 Dimethicone, Bis-PEG/PPG-16/16 PEG/PPG-16/16 Dimethicone, Bis-PEG/PPG-20/5 PEG/PPG-20/5 Dimethicone, PEG/PPG-25/4 Dimethicone, Bis-(Glyceryl/Lauryl) Glyceryl Lauryl Dimethicone, Bis-PEG/PPG-14/14 Dimethicone, or mixtures thereof.

52. The composition of claim 50, wherein the ionic surfactant is present in an amount of from about 5% to about 30% by weight, based on the total weight of the surfactant mixture.

53. The composition of claim 52, wherein the at least one ionic surfactant comprises at least one cationic surfactant selected from cetrimonium chloride, behentrimonium chloride, dipalmitoylethyl hydroxyethylmonium methosulfate, distearoylethyl hydroxyethylmonium methosulfate, or mixtures thereof.

54. The composition of claim 52, wherein the at least one ionic surfactant comprises at least one anionic surfactant selected from acyl glutamates, alkyl sulfates and their salts, alkyl ether sulfates and their salts, acyl glutamates, alkyl ether carboxylates, or mixtures thereof.

55. The composition of claim 54, wherein the at least one anionic surfactant is selected from disodium stearoyl glutamate, sodium stearoyl glutamate, or mixtures thereof.

56. The composition of claim 30, further comprising an oil gellant other than a)(i) that is selected from semi-crystalline polymers, a glutamide-based compound, a polyamide, or mixtures thereof.

57. The composition of claim 30, wherein the aqueous dispersion is present in an amount of from about 1% to about 30% by weight, based on the total weight of the composition.

58. The composition of claim 30, wherein the particles of the aqueous dispersion are heat-activated.

59. The composition of claim 30, wherein the composition is a cosmetic or dermatological or personal care or pharmaceutical composition and wherein the composition includes a carrier comprising water, volatile organic solvents, non-volatile organic solvents, silicones, non-silicone oils, or mixtures thereof.

60. The composition of claim 59, wherein the composition further comprises at least one auxiliary agent selected from liquid lipids/oils, film forming polymers, rheology modifiers, humectants and moisturizing agents, emulsifying agents, structuring agents, propellants, surfactants, shine agents, conditioning agents, cosmetically, dermatologically and pharmaceutically active agents, vitamins, plant extracts, or mixtures thereof.

61. The composition of claim 30, wherein the particles optionally further comprise at least one additional ingredient selected from an oil gellant other than a)(i), colorants, sunscreen agents, a wax having a melting point of 35° C. or less, emulsifying polymers, fragrance oils other than the at least one oil in a)(ii), silicas, talc, clays, or mixtures thereof.

62. The composition of claim 61, wherein the particles of the aqueous dispersion are obtained by a process comprising:
(1) heating the fatty substance;
(2) optionally, if present, heating the at least one optional additional ingredient with the fatty substance in (1);
(3) heating the oil gellant comprising at least one styrenic block copolymer;
(4) mixing the fatty substance in (1) or in (2) with the oil gellant in (3) to form a styrenic block copolymer oil gellant/fatty substance blend;
(5) heating the surfactant mixture comprising at least one nonionic surfactant and at least one ionic surfactant and the water to form a surfactant/water combination;
(6) mixing the styrenic block copolymer oil gellant/fatty substance blend with the surfactant/water combination by a shearing action to form the aqueous dispersion; and
(7) cooling the aqueous dispersion in (6);
wherein when the fatty substance comprises the at least one wax having a melting point of greater than 35° C., the fatty substance is heated to a temperature above the melting point of the at least one wax.

63. A composition for shaping hair comprising:
A. an aqueous dispersion containing:
a) particles having a volume-basis particle size distribution with peaks in the range of 20 μm up to about 70 μm, wherein at least one of the particles comprises:
(i) from about 0.1% to about 15% by weight of an oil gellant comprising at least one styrenic block copolymer selected from a styrene-ethylene/butylene diblock copolymer, a styrene-ethylene/butylene-styrene triblock copolymer, or mixtures thereof; and
(ii) from about 10% to about 60% by weight of a fatty substance selected from at least one wax having a melting point of greater than 35° C. selected from beeswax, hydrogenated myristyl olive esters, hydrogenated stearyl olive esters, VP/eicosene copolymer, ditrimethyloylpropane tetrastearate, and C30-45 alkyldimethylsilyl propylsilsesquioxane, or mixtures thereof;
b) from about 1% to about 5% by weight of a surfactant mixture comprising:
(i) at least one nonionic surfactant selected from PEG-30 glyceryl stearate, sorbitan palmitate, Cetyl PEG/PPG-10/1 Dimethicone, Bis-PEG/PPG-16/16 PEG/PPG-16/16 Dimethicone, Bis-PEG/PPG-20/5 PEG/PPG-20/5 Dimethicone, PEG/PPG-25/4 Dimethicone, Bis-(Glyceryl/Lauryl) Glyceryl Lauryl Dimethicone, Bis-PEG/PPG-14/14 Dimethicone, or mixtures thereof; and
(ii) at least one ionic surfactant; and
c) water;
all weights being based on the total weight of the aqueous dispersion;
B. a carrier comprising water, volatile organic solvents, non-volatile organic solvents, silicones, non-silicone oils, or mixtures thereof; and
C. optionally, at least one auxiliary ingredient selected from liquid lipids/oils, waxes, film forming polymers, rheology modifiers, humectants and moisturizing agents, emulsifying agents, structuring agents, propellants, surfactants, shine agents, conditioning agents, cosmetically, dermatologically and pharmaceutically active agents, vitamins, plant extracts, or mixtures thereof.

64. The composition of claim 63, wherein the at least one ionic surfactant is an anionic surfactant selected from dipalmitoylethyl hydroxyethylmonium methosulfate, distearoylethyl hydroxyethylmonium methosulfate, disodium stearoyl glutamate and sodium stearoyl glutamate, or mixtures thereof.

65. The composition of claim 63, wherein the at least one ionic surfactant is a cationic surfactant selected from cetrimonium chloride, behentrimonium chloride, or mixtures thereof.

66. The composition of claim 63, wherein the particles optionally further comprise at least one additional ingredient selected from an oil gellant other than a)(i), colorants, sunscreen agents, a wax having a melting point of 35° C. or less, emulsifying polymers, fragrance oils, silicas, talc, clays, or mixtures thereof.

67. A method of shaping hair comprising: (i) applying the composition of claim 60 onto hair; (ii) applying heat to the hair; and (iii) optionally, using a means for shaping the hair.

68. A method of making up or caring for a keratinous substrate, comprising applying the composition of claim 60 onto the substrate.

69. A method of coating a substrate comprising applying the composition of claim 30 onto the substrate and optionally, applying heat to the substrate.

70. A method of shaping hair, the method comprising:
I. applying onto the hair, a composition containing:
   A. an aqueous dispersion comprising:
      a) particles having a volume-basis particle size distribution with peaks in the range of 20 82 m up to about 70 μm, wherein at least one of the particles comprises:
         (i) from about 0.1% to about 15% by weight of an oil gellant comprising at least one styrenic block copolymer; and
         (ii) a fatty substance selected from at least one wax having a melting point of greater than 35° C., at least one oil, or mixtures thereof;
      b) from about 1% to about 5% by weight of a surfactant mixture comprising:
         (i) at least one nonionic surfactant selected from polyethylene glycol ethers of glyceryl esters, sorbitan esters, silicone-based emulsifying polymers having alkoxylated groups and/or side chains, or mixtures thereof; and
         (ii) at least one ionic surfactant; and
      c) water;
   all weights being based on the total weight of the aqueous dispersion;
   B. a carrier comprising water, volatile organic solvents, non-volatile organic solvents, silicones, non-silicone oils, or mixtures thereof; and
   C. optionally, at least one auxiliary ingredient selected from liquid lipids/oils, waxes, film forming polymers, rheology modifiers, humectants and moisturizing agents, emulsifying agents, structuring agents, propellants, surfactants, shine agents, conditioning agents, cosmetically, dermatologically and pharmaceutically active agents, vitamins, plant extracts, or mixtures thereof; and
II. applying heat to the hair; and
III. optionally, using a means for shaping the hair.

71. The method of claim 70, wherein the fatty substance is selected from the least one wax having a melting point of greater than 35° C. and the ionic surfactant is an anionic surfactant.

72. The method of claim 70, wherein the particles further comprise at least one additional ingredient selected from an oil gellant other than a)(i), colorants, sunscreen agents, a wax having a melting point of 35° C. or less, emulsifying polymers, fragrance oils other than the at least one oil in a)(ii), silicas, talc, clays, or mixtures thereof.

* * * * *

UNITED STATES PATENT AND TRADEMARK OFFICE
CERTIFICATE OF CORRECTION

PATENT NO. : 10,561,596 B2
APPLICATION NO. : 14/251373
DATED : February 18, 2020
INVENTOR(S) : Jean Thierry Simonnet et al.

It is certified that error appears in the above-identified patent and that said Letters Patent is hereby corrected as shown below:

In the Claims

Column 67, Line 5, Claim 70: please change "20 82 m" to -- 20 μm --.

Signed and Sealed this
Twenty-fourth Day of May, 2022

Katherine Kelly Vidal
*Director of the United States Patent and Trademark Office*